US007306796B2

(12) United States Patent
Afar et al.

(10) Patent No.: US 7,306,796 B2
(45) Date of Patent: Dec. 11, 2007

(54) 13-TRANSMEMBRANE PROTEIN EXPRESSED IN PROSTATE CANCER

(75) Inventors: Daniel E. Afar, Pacific Palisades, CA (US); Rene S. Hubert, Los Angeles, CA (US); Kahan Leong, Playa del Rey, CA (US); Arthur B. Raitano, Los Angeles, CA (US); Douglas C. Saffran, Los Angeles, CA (US)

(73) Assignee: Agensys, Inc., Santa Monica, CA (US)

( * ) Notice: Subject to any disclaimer, the term of this patent is extended or adjusted under 35 U.S.C. 154(b) by 644 days.

(21) Appl. No.: 10/284,660

(22) Filed: Oct. 30, 2002

(65) Prior Publication Data

US 2003/0157521 A1 Aug. 21, 2003

Related U.S. Application Data

(63) Continuation of application No. 09/547,789, filed on Apr. 12, 2000, now Pat. No. 6,943,235.

(60) Provisional application No. 60/128,858, filed on Apr. 12, 1999.

(51) Int. Cl.
*A61K 39/395* (2006.01)

(52) U.S. Cl. .................................................. 424/130.1

(58) Field of Classification Search ..................... None
See application file for complete search history.

(56) References Cited

U.S. PATENT DOCUMENTS 6,312,922 B1 11/2001 Edwards et al.
6,913,919 B2 7/2005 Botstein et al.
6,930,170 B2 8/2005 Desnoyers et al.
6,943,235 B1 9/2005 Afar et al.
6,953,836 B2 10/2005 Desnoyers et al.
6,956,108 B2 10/2005 Desnoyers et al.
6,972,185 B2 12/2005 Desnoyers et al.
7,018,811 B2 3/2006 Botstein et al.
7,019,116 B2 3/2006 Desnoyers et al.
7,029,873 B2 4/2006 Desnoyers et al.
7,034,106 B2 4/2006 Desnoyers et al.
7,034,122 B2 4/2006 Desnoyers et al.
7,034,136 B2 4/2006 Goddard et al.
2002/0022248 A1 2/2002 Xu et al.
2002/0103125 A1 8/2002 Ashkenazi et al. ........... 514/12
2002/0119130 A1 8/2002 Eaton et al. ............... 424/94.1
2002/0123463 A1 9/2002 Ashkenazi et al. ........... 514/12
2002/0127576 A1 9/2002 Ashkenazi et al. ............ 435/6
2002/0132252 A1 9/2002 Ashkenazi et al. ............ 435/6
2002/0142961 A1 10/2002 Ashkenazi et al. ........... 514/12
2002/0160384 A1 10/2002 Ashkenazi et al. ............ 435/6
2002/0177164 A1 11/2002 Ashkenazi et al. .......... 435/7.1
2002/0182638 A1 12/2002 Eaton et al. ................. 435/7.1
2002/0183493 A1 12/2002 Eaton et al. ............. 530/388.1
2002/0183494 A1 12/2002 Eaton et al. ............. 530/388.1
2002/0192763 A1 12/2002 Xu et al. ................... 435/69.7
2002/0193299 A1 12/2002 Ashkenazi et al. ........... 514/12
2002/0193300 A1 12/2002 Ashkenazi et al. ........... 514/12
2002/0197615 A1 12/2002 Ashkenazi et al. ............ 435/6
2002/0198148 A1 12/2002 Ashkenazi et al. ........... 514/12
2003/0003531 A1 1/2003 Ashkenazi et al. ........ 435/69.1
2003/0008297 A1 1/2003 Ashkenazi et al. ............ 435/6
2003/0009012 A1 1/2003 Eaton et al. ............. 530/388.1
2003/0009013 A1 1/2003 Eaton et al. ............. 530/388.1
2003/0013855 A1 1/2003 Eaton et al. ............. 530/388.1
2003/0017476 A1 1/2003 Ashkenazi et al. ............ 435/6
2003/0017981 A1 1/2003 Ashkenazi et al. ........... 514/12
2003/0017982 A1 1/2003 Ashkenazi et al. ........... 514/12
2003/0018168 A1 1/2003 Eaton et al. ................ 530/350
2003/0018172 A1 1/2003 Eaton et al. ........... 530/388.15
2003/0018173 A1 1/2003 Eaton et al. ........... 530/388.15
2003/0018183 A1 1/2003 Eaton et al. ............... 536/23.5
2003/0022187 A1 1/2003 Ashkenazi et al. ............ 435/6
2003/0023042 A1 1/2003 Eaton et al. ............. 530/388.1
2003/0027162 A1 2/2003 Ashkenazi et al. ............ 435/6
2003/0027163 A1 2/2003 Ashkenazi et al. ............ 435/6
2003/0027212 A1 2/2003 Eaton et al. ................. 435/7.1
2003/0027754 A1 2/2003 Ashkenazi et al. ........... 514/12
2003/0027985 A1 2/2003 Ashkenazi et al. ......... 530/350
2003/0027986 A1 2/2003 Eaton et al. ................ 530/350
2003/0027992 A1 2/2003 Eaton et al. ............. 530/388.1
2003/0027993 A1 2/2003 Eaton et al. ............. 530/388.1
2003/0032023 A1 2/2003 Ashkenazi et al. ............ 435/6

(Continued)

FOREIGN PATENT DOCUMENTS

EP 1033401 A2 9/2000

(Continued)

OTHER PUBLICATIONS

Gura, 1997, Science 278:1041-1042.*
McClean and Hill, 1993, Eur J of Cancer 29A:2243-2248.*
Fu et al., 1996, EMBO Journal 15:4392-4401.*
Brennan et al., 1989, Journal of Autoimmunity 2 (suppl.):177-186.*
Zimmer, 1991, Cell Motility and the Cytoskeleton 20:325-337.*
Eriksson et al., 1992, Diabetologia 35:143-147).*
White et al., 2001, Ann. Rev. Med. 52:125-145.*
Bowie et al., Science 247:1306-1310.*
Busken, C et al, Digestive Disease Week Abstracts and Itinerary Planner, 2003, abstract No:850.*
Freshney (Culture of Animal Cells, A Manual of Basic Technique, Alan R. Liss, Inc., 1983, New York, p. 4).*

(Continued)

*Primary Examiner*—Karen A. Canella
*Assistant Examiner*—Catherine Joyce
(74) *Attorney, Agent, or Firm*—Morrison & Foerster LLP

(57) ABSTRACT

A novel prostate tumor associated gene (designated 24P4C12) and its encoded protein is described. 24P4C12 is highly expressed in prostate tissue xenografts, providing evidence that it is turned on in at least some prostate cancers. 24P4C12 provides a diagnostic and/or therapeutic target for prostate and other cancers.

8 Claims, 18 Drawing Sheets

U.S. PATENT DOCUMENTS

| | | | | |
|---|---|---|---|---|
| 2003/0036634 | A1 | 2/2003 | Eaton et al. | 530/350 |
| 2003/0040473 | A1 | 2/2003 | Ashkenazi et al. | 514/12 |
| 2003/0044806 | A1 | 3/2003 | Ashkenazi et al. | 435/6 |
| 2003/0045463 | A1 | 3/2003 | Ashkenazi et al. | 514/12 |
| 2003/0045684 | A1 | 3/2003 | Eaton et al. | 530/350 |
| 2003/0049638 | A1 | 3/2003 | Ashkenazi et al. | 435/6 |
| 2003/0049681 | A1 | 3/2003 | Ashkenazi et al. | 435/7.1 |
| 2003/0049682 | A1 | 3/2003 | Ashkenazi et al. | 435/7.1 |
| 2003/0049735 | A1 | 3/2003 | Eaton et al. | 435/69.1 |
| 2003/0050462 | A1 | 3/2003 | Eaton et al. | 536/23.2 |
| 2003/0050465 | A1 | 3/2003 | Eaton et al. | 536/23.2 |
| 2003/0054359 | A1 | 3/2003 | Ashkenazi et al. | 435/6 |
| 2003/0054403 | A1 | 3/2003 | Ashkenazi et al. | 435/7.1 |
| 2003/0054404 | A1 | 3/2003 | Ashkenazi et al. | 435/7.1 |
| 2003/0054987 | A1 | 3/2003 | Ashkenazi et al. | 514/12 |
| 2003/0059780 | A1 | 3/2003 | Ashkenazi et al. | 435/6 |
| 2003/0059782 | A1 | 3/2003 | Ashkenazi et al. | 435/6 |
| 2003/0059783 | A1 | 3/2003 | Ashkenazi et al. | 435/6 |
| 2003/0059831 | A1 | 3/2003 | Ashkenazi et al. | 435/7.1 |
| 2003/0059832 | A1 | 3/2003 | Ashkenazi et al. | 435/7.1 |
| 2003/0059833 | A1 | 3/2003 | Ashkenazi et al. | 435/7.1 |
| 2003/0060407 | A1 | 3/2003 | Ashkenazi et al. | 514/12 |
| 2003/0060600 | A1 | 3/2003 | Eaton et al. | 530/350 |
| 2003/0060601 | A1 | 3/2003 | Eaton et al. | 530/350 |
| 2003/0060602 | A1 | 3/2003 | Eaton et al. | 530/350 |
| 2003/0064375 | A1 | 4/2003 | Ashkenazi et al. | 435/6 |
| 2003/0065143 | A1 | 4/2003 | Eaton et al. | 530/350 |
| 2003/0065161 | A1 | 4/2003 | Eaton et al. | 536/23.5 |
| 2003/0068623 | A1 | 4/2003 | Ashkenazi et al. | 435/6 |
| 2003/0068647 | A1 | 4/2003 | Ashkenazi et al. | 435/7.1 |
| 2003/0069394 | A1 | 4/2003 | Eaton et al. | 530/350 |
| 2003/0069403 | A1 | 4/2003 | Ashkenazi et al. | 536/23.1 |
| 2003/0073090 | A1 | 4/2003 | Ashkenazi et al. | 435/6 |
| 2003/0073623 | A1 | 4/2003 | Drmanac et al. | 514/12 |
| 2003/0078387 | A1 | 4/2003 | Eaton et al. | 530/388.15 |
| 2003/0082546 | A1 | 5/2003 | Ashkenazi et al. | 435/6 |
| 2003/0083461 | A1 | 5/2003 | Ashkenazi et al. | 530/350 |
| 2003/0083473 | A1 | 5/2003 | Eaton et al. | 530/388.15 |
| 2003/0087304 | A1 | 5/2003 | Ashkenazi et al. | 435/7.1 |
| 2003/0087305 | A1 | 5/2003 | Ashkenazi et al. | 435/7.1 |
| 2003/0099974 | A1 | 5/2003 | Lillie et al. | 435/6 |
| 2003/0147904 | A1 | 8/2003 | Afar et al. | |

FOREIGN PATENT DOCUMENTS

| | | | |
|---|---|---|---|
| EP | 1074617 | A2 | 2/2001 |
| WO | WO 99/06548 | | 2/1999 |
| WO | WO 99/06549 | | 2/1999 |
| WO | WO 99/06550 | | 2/1999 |
| WO | WO9906548 | A2 | 2/1999 |
| WO | WO9906550 | A2 | 2/1999 |
| WO | WO9940189 | A2 | 8/1999 |
| WO | WO 99/63088 | | 12/1999 |
| WO | WO9963088 | A2 | 12/1999 |
| WO | WO 99/04149 | | 1/2000 |
| WO | WO0004149 | A2 | 1/2000 |
| WO | WO0061746 | A1 | 10/2000 |
| WO | WO0073454 | A1 | 12/2000 |
| WO | WO0077021 | A1 | 12/2000 |
| WO | WO0116318 | A2 | 3/2001 |
| WO | WO0125272 | A2 | 4/2001 |
| WO | WO0134802 | A2 | 5/2001 |
| WO | WO0146258 | A2 | 6/2001 |
| WO | WO0151628 | A2 | 7/2001 |
| WO | WO0151633 | A2 | 7/2001 |
| WO | WO0153836 | A2 | 7/2001 |
| WO | WO0157270 | A2 | 8/2001 |
| WO | WO0157271 | A2 | 8/2001 |
| WO | WO0157272 | A2 | 8/2001 |
| WO | WO0157273 | | 8/2001 |
| WO | WO0157274 | A2 | 8/2001 |
| WO | WO0157275 | A2 | 8/2001 |
| WO | WO0157276 | A2 | 8/2001 |
| WO | WO0157277 | A2 | 8/2001 |
| WO | WO0157278 | A2 | 8/2001 |
| WO | WO0160860 | A2 | 8/2001 |
| WO | WO0173027 | A2 | 10/2001 |
| WO | WO0173032 | A2 | 10/2001 |
| WO | WO0175067 | A2 | 10/2001 |
| WO | WO0186003 | A2 | 11/2001 |
| WO | WO0190304 | A2 | 11/2001 |
| WO | WO0196388 | A2 | 12/2001 |
| WO | WO0196390 | A2 | 12/2001 |
| WO | WO0212328 | A2 | 2/2002 |
| WO | WO0258534 | | 8/2002 |
| WO | WO0274961 | | 9/2002 |
| WO | WO0283876 | | 10/2002 |
| WO | WO0289747 | | 11/2002 |
| WO | WO0297031 | | 12/2002 |

OTHER PUBLICATIONS

Dermer (Bio/Technology, 1994, 12:320).*

Drexler et al (Leukemia and Lumphoma, 1993, 9:1-25).*

Zellner et al (Clin. Can. Res., 1998, 4:1797-17802).*

Hsu (in Tissue Culture Methods and Applications, Kruse and Patterson, Eds, 1973, Academic Press, NY, see abstract, p. 764).*

International Search Report for PCT/US02/38264, mailed on Oct. 20, 2004, 3 pages.

Huang, G.M. et al., "Prostate cancer expression profiling by cDNA sequencing analysis," EMBL Database entry AI557659, Accession No. AI557659, Mar. 25, 1999, EP002144281, & Huang, G.M. et al., Genomics, vol. 59, No. 2, Jul. 1999, pp. 178-186.

NCI-CGAP, "National Cancer Institute, Cancer Genome Anatomy Project (CGAP)", Oct. 7, 1997, EMBL Database Entry AA612666, Accession No. AA612666, XP002144282.

Rowen, L. et al., "Sequence of the human major histocompatibility complex class III region", Mar. 29, 1999, EMBL Database Entry AF134726, Accession No. AF134726, XP002144283.

Rowen, L. et al., "Sequence of the human major histocompatibility complex class III region", Nov. 1, 1999, EMBL Database Entry Q9Y332, XP002144284.

Reiter, Robert E. et al., Prostate stem cell antigen: A cell surface marker overexpressed in prostate cancer:, Proc. Natl. Acad. Sci., Feb. 1998, vol. 95, pp. 1735-1740, XP-002078363.

Rowen, L., Mar. 24, 1999, NCBI Accession No. AAD21813.

Inoko, Hidetoshi, Mar. 30, 2000, NCBI Accession No. AP000502.

Simpson, A.J.G., Mar. 16, 2000, dbEST Id 4011587, GenBank Acc. AW579065.

Simpson, A. J. G., Mar. 23, 2000, dbEST Id 40366492 GenBank Acc. AW603383.

Simpson, A. J. G., Mar. 23, 2000, dbEST Id 4035408, GenBank Acc. AW602142.

Strausberg, Robert, Sep. 6, 1999, dbEST Id 3075200, GenBank Acc. AI951815.

Strausberg, Robert, Mar. 9, 2000, dbEST Id 3079479, GenBank Acc. AI956094.

Strausberg, Robert, Jun. 21, 1999, dbEST ID 2655196, GenBank Acc. AI745450.

Strausberg, Robert, Mar. 7, 2000, dbEST Id 2893738, GenBank Acc. AI813886.

Simpson, A.J.G., Feb. 4, 2000, dbEST Id 3787048, GenBank Acc. AW393065.

Huang, Guyang Matthew, Aug. 9, 1999, dbEST Id 2373824, GenBank Acc. AI557660.

Strausberg, Robert, Aug. 14, 1997, dbEST Id 1112901, GenBank Acc. AA468365.

Wilson, R. K., Jun. 10, 1999, dbEST Id 2629269, GenBank Acc. AI721101.

Strausberg, Robert, Aug. 21, 1997, dbEST Id 1178186, GenBank Acc. AA533783.

Strausberg, Robert, Feb. 16, 1999, dbEST Id 2101871, GenBank Acc. AI318311.

Strausberg, Robert, Oct. 30, 1999, dbEST Id 3291479, GenBank Acc. AW139432.
Strausberg, Robert, Feb. 24, 2000, dbEST Id 3880006, GenBank Acc. AW469133.
Strausberg, Robert, Mar. 7, 2000, dbEST Id 2947457, GenBank Acc. AI858987.
Strausberg, Robert, May 13, 1999, dbEST Id 2376359, GenBank Acc. AI560195.
Strausberg, Robert, Mar. 7, 2000, dbEST Id 2946846, GenBank Acc. AI858299.
Strausberg, Robert, May 14, 1999, dbEST Id 2390443, GenBank Acc. AI572115.
Strausberg, Robert, May 14, 1999, dbEST Id2381301, GenBank Acc. AI565097.
Takeda, Jun, Sep. 9, 1997, dbEST Id 1241269, GenBank Acc. C75094.
Wilson, R. K., Jul. 7, 1995, dbEST Id 285541, GenBank Acc. H25030.
Kerlavage, A. R, Apr. 21, 1997, dbEST Id 1008183, GenBank Acc. AA 366876.
Strausberg, Robert, Dec. 14, 1999, dbEST Id 2443929, GenBank Acc. AI625125.
Wilson, R. K., Apr. 20, 1995, dbEST Id 194186, GenBank Acc. R24141.
Strausberg, Robert, Mar. 8, 2000, dbEST Id 3055029, GenBank Acc. AI932443.
Ezzell, Journal of NIH Research (1995) 7:46-49.
Spitler, Cancer Biotherapy (1995) 10:1-3.
Dulcert et al., Accession No. AAY12282, 1999.
McClean and Hill, Eur. J. Cancer (1993) 29A:2243-2248.
Fu et al., EMBO Journal (1996) 15:4392-4401.
Brennan et al., Journal of Autoimmunity (1989) 2(suppl.):177-186.
Zimmer, Cell Motility and the Cytoskeleton (1991) 20:325-337.
Ericksson et al., Diabetologia (1992) 35:143-147.
Craft et al., Cancer Res. (1999) 59:5030-5036.
Kilty and Amara, Curr. Opin. Biotechnology (1992) 3:675-682.
Klein et al., Nature Med. (1997) 3:402-408.
Morton and Myszka, Methods in Enzymology (1998) 295:268.
Muller et al., MCB (1991) 11:1785.
Pemberton et al., J. of Histochemistry and Cytochemistry (1997) 45:1697-1706.
Storrie et al., Methods Enzymol. (1990) 182:203-225.
Welch et al., Int. J. Cancer (1989) 43:449-457.
Welford, Opt. Quant. Elect. (1991) 23:1.
Alberts et al., Molecular Biology of the Cell, 3rd edition (1994) p. 465.
Lewin, Genes VI, Oxford University Press, Inc. New York (1997) Chapter 29.
Mallampalli et al., Biochem. J. (1996) 318:333-341.
Boehringer Mannheim Biochemicals, 1994 Catalog, p. 93.
Benedict et al., J. Exp. Medicine (2001) 193(1):89-99.
Hirashima et al., Int. Arch. Allergy Immunol. (2000) Suppl. 1:6-9.
Jiang et al., JBC (2003) 278(7):4763-4769.
Paul, W.E., ed., Fundamental Immunology, Raven Press (1984) pp. 615-617.

* cited by examiner

FIG. 1A

```
            11          20          29          38          47          56
GCC ATG GGG GGA AAG CAG CGG GAC GAG GAT GAC GAG GCC TAC GGG AAG CCA GTC
--- --- --- --- --- --- --- --- --- --- --- --- --- --- --- --- --- ---
     M   G   G   K   Q   R   D   E   D   D   E   A   Y   G   K   P   V

            65          74          83          92         101         110
AAA TAC GAC CCC TCC TTT CGA GGC CCC ATC AAG AAC AGA AGC TGC ACA GAT GTC
--- --- --- --- --- --- --- --- --- --- --- --- --- --- --- --- --- ---
 K   Y   D   P   S   F   R   G   P   I   K   N   R   S   C   T   D   V

           119         128         137         146         155         164
ATC TGC TGC GTC CTC TTC CTG CTC TTC ATT CTA GGT TAC ATC GTG GTG GGG ATT
--- --- --- --- --- --- --- --- --- --- --- --- --- --- --- --- --- ---
 I   C   C   V   L   F   L   L   F   I   L   G   Y   I   V   V   G   I

           173         182         191         200         209         218
GTG GCC TGG TTG TAT GGA GAC CCC CGG CAA GTC CTC TAC CCC AGG AAC TCT ACT
--- --- --- --- --- --- --- --- --- --- --- --- --- --- --- --- --- ---
 V   A   W   L   Y   G   D   P   R   Q   V   L   Y   P   R   N   S   T

           227         236         245         254         263         272
GGG GCC TAC TGT GGC ATG GGG GAG AAC AAA GAT AAG CCG TAT CTC CTG TAC TTC
--- --- --- --- --- --- --- --- --- --- --- --- --- --- --- --- --- ---
 G   A   Y   C   G   M   G   E   N   K   D   K   P   Y   L   L   Y   F

           281         290         299         308         317         326
AAC ATC TTC AGC TGC ATC CTG TCC AGC AAC ATC ATC TCA GTT GCT GAG AAC GGC
--- --- --- --- --- --- --- --- --- --- --- --- --- --- --- --- --- ---
 N   I   F   S   C   I   L   S   S   N   I   I   S   V   A   E   N   G

           335         344         353         362         371         380
CTA CAG TGC CCC ACA CCC CAG GTG TGT GTG TCC TCC TGC CCG GAG GAC CCA TGG
--- --- --- --- --- --- --- --- --- --- --- --- --- --- --- --- --- ---
 L   Q   C   P   T   P   Q   V   C   V   S   S   C   P   E   D   P   W

           389         398         407         416         425         434
ACT GTG GGA AAA AAC GAG TTC TCA CAG ACT GTT GGG GAA GTC TTC TAT ACA AAA
--- --- --- --- --- --- --- --- --- --- --- --- --- --- --- --- --- ---
 T   V   G   K   N   E   F   S   Q   T   V   G   E   V   F   Y   T   K

           443         452         461         470         479         488
AAC AGG AAC TTT TGT CTG CCA GGG GTA CCC TGG AAT ATG ACG GTG ATC ACA AGC
--- --- --- --- --- --- --- --- --- --- --- --- --- --- --- --- --- ---
 N   R   N   F   C   L   P   G   V   P   W   N   M   T   V   I   T   S

           497         506         515         524         533         542
CTG CAA CAG GAA CTC TGC CCC AGT TTC CTC CTC CCC TCT GCT CCA GCT CTG GGG
--- --- --- --- --- --- --- --- --- --- --- --- --- --- --- --- --- ---
 L   Q   Q   E   L   C   P   S   F   L   L   P   S   A   P   A   L   G

           551         560         569         578         587         596
CGC TGC TTT CCA TGG ACC AAC GTT ACT CCA CCG GCG CTC CCA GGG ATC ACC AAT
--- --- --- --- --- --- --- --- --- --- --- --- --- --- --- --- --- ---
 R   C   F   P   W   T   N   V   T   P   P   A   L   P   G   I   T   N
```

Figure 1B:
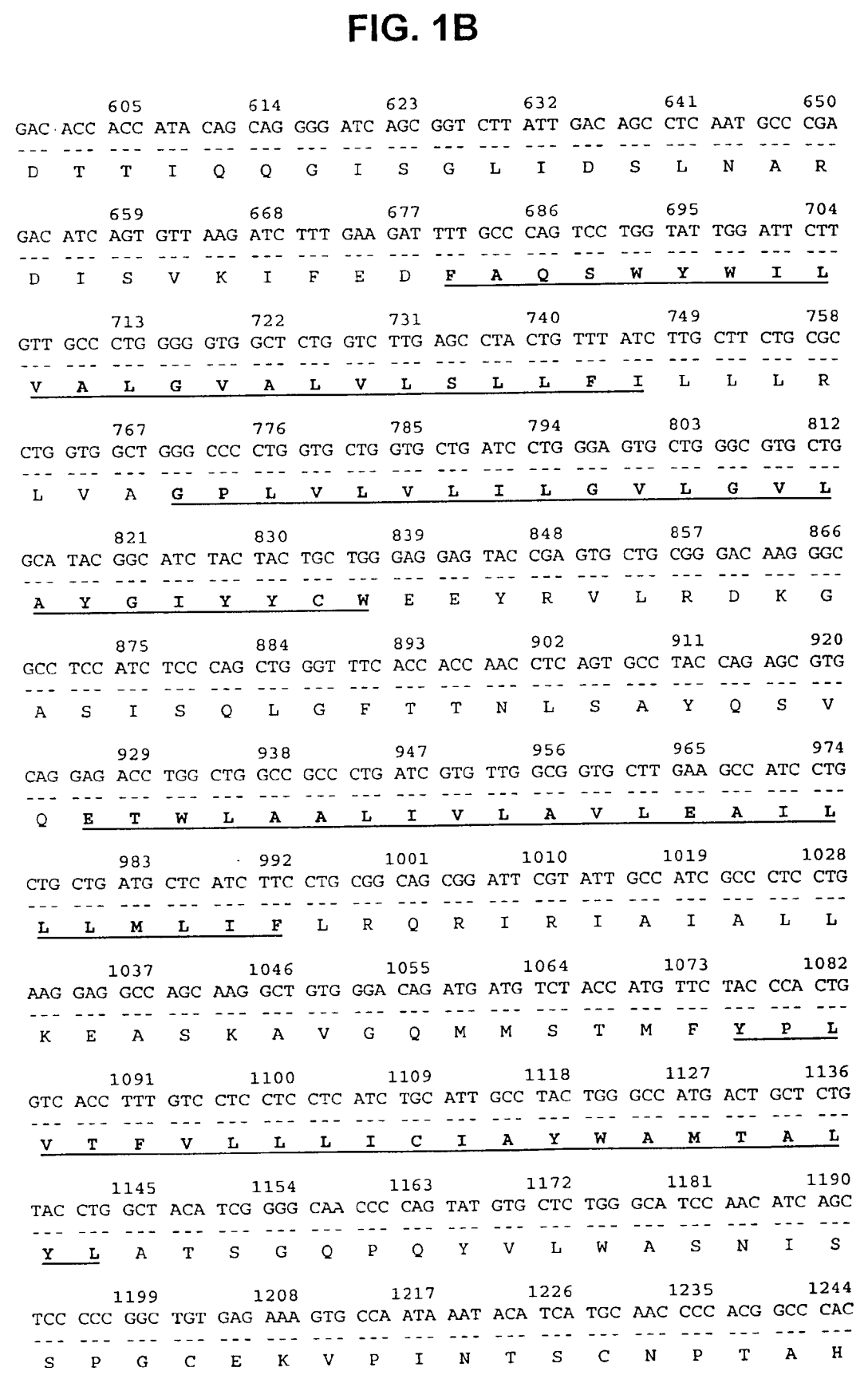

FIG. 1B 605 614 623 632 641 650
GAC ACC ACC ATA CAG CAG GGG ATC AGC GGT CTT ATT GAC AGC CTC AAT GCC CGA
D T T I Q Q G I S G L I D S L N A R 659 668 677 686 695 704
GAC ATC AGT GTT AAG ATC TTT GAA GAT TTT GCC CAG TCC TGG TAT TGG ATT CTT
D I S V K I F E D F A Q S W Y W I L 713 722 731 740 749 758
GTT GCC CTG GGG GTG GCT CTG GTC TTG AGC CTA CTG TTT ATC TTG CTT CTG CGC
V A L G V A L V L S L L F I L L L R 767 776 785 794 803 812
CTG GTG GCT GGG CCC CTG GTG CTG GTG CTG ATC CTG GGA GTG CTG GGC GTG CTG
L V A G P L V L V L I L G V L G V L 821 830 839 848 857 866
GCA TAC GGC ATC TAC TAC TGC TGG GAG GAG TAC CGA GTG CTG CGG GAC AAG GGC
A Y G I Y Y C W E E Y R V L R D K G 875 884 893 902 911 920
GCC TCC ATC TCC CAG CTG GGT TTC ACC ACC AAC CTC AGT GCC TAC CAG AGC GTG
A S I S Q L G F T T N L S A Y Q S V 929 938 947 956 965 974
CAG GAG ACC TGG CTG GCC GCC CTG ATC GTG TTG GCG GTG CTT GAA GCC ATC CTG
Q E T W L A A L I V L A V L E A I L 983 992 1001 1010 1019 1028
CTG CTG ATG CTC ATC TTC CTG CGG CAG CGG ATT CGT ATT GCC ATC GCC CTC CTG
L L M L I F L R Q R I R I A I A L L 1037 1046 1055 1064 1073 1082
AAG GAG GCC AGC AAG GCT GTG GGA CAG ATG ATG TCT ACC ATG TTC TAC CCA CTG
K E A S K A V G Q M M S T M F Y P L 1091 1100 1109 1118 1127 1136
GTC ACC TTT GTC CTC CTC CTC ATC TGC ATT GCC TAC TGG GCC ATG ACT GCT CTG
V T F V L L L I C I A Y W A M T A L 1145 1154 1163 1172 1181 1190
TAC CTG GCT ACA TCG GGG CAA CCC CAG TAT GTG CTC TGG GCA TCC AAC ATC AGC
Y L A T S G Q P Q Y V L W A S N I S 1199 1208 1217 1226 1235 1244
TCC CCC GGC TGT GAG AAA GTG CCA ATA AAT ACA TCA TGC AAC CCC ACG GCC CAC
S P G C E K V P I N T S C N P T A H

FIG. 1C

```
     1253        1262        1271        1280        1289        1298
CTT GTG AAC TCC TCG TGC CCA GGG CTG ATG TGC GTC TTC CAG GGC TAC TCA TCC
 L   V   N   S   S   C   P   G   L   M   C   V   F   Q   G   Y   S   S

     1307        1316        1325        1334        1343        1352
AAA GGC CTA ATC CAA CGT TCT GTC TTC AAT CTG CAA ATC TAT GGG GTC CTG GGG
 K   G   L   I   Q   R   S   V   F   N   L   Q   I   Y   G   V   L   G

     1361        1370        1379        1388        1397        1406
CTC TTC TGG ACC CTT AAC TGG GTA CTG GCC CTG GGC CAA TGC GTC CTC GCT GGA
 L   F   W   T   L   N   W   V   L   A   L   G   Q   C   V   L   A   G

     1415        1424        1433        1442        1451        1460
GCC TTT GCC TCC TTC TAC TGG GCC TTC CAC AAG CCC CAG GAC ATC CCT ACC TTC
 A   F   A   S   F   Y   W   A   F   H   K   P   Q   D   I   P   T   F

     1469        1478        1487        1496        1505        1514
CCC TTA ATC TCT GCC TTC ATC CGC ACA CTC CGT TAC CAC ACT GGG TCA TTG GCA
 P   L   I   S   A   F   I   R   T   L   R   Y   H   T   G   S   L   A

     1523        1532        1541        1550        1559        1568
TTT GGA GCC CTC ATC CTG ACC CTT GTG CAG ATA GCC CGG GTC ATC TTG GAG TAT
 F   G   A   L   I   L   T   L   V   Q   I   A   R   V   I   L   E   Y

     1577        1586        1595        1604        1613        1622
ATT GAC CAC AAG CTC AGA GGA GTG CAG AAC CCT GTA GCC CGC TGC ATC ATG TGC
 I   D   H   K   L   R   G   V   Q   N   P   V   A   R   C   I   M   C

     1631        1640        1649        1658        1667        1676
TGT TTC AAG TGC TGC CTC TGG TGT CTG GAA AAA TTT ATC AAG TTC CTA AAC CGC
 C   F   K   C   C   L   W   C   L   E   K   F   I   K   F   L   N   R

     1685        1694        1703        1712        1721        1730
AAT GCA TAC ATC ATG ATC GCC ATC TAC GGG AAG AAT TTC TGT GTC TCA GCC AAA
 N   A   Y   I   M   I   A   I   Y   G   K   N   F   C   V   S   A   K

     1739        1748        1757        1766        1775        1784
AAT GCG TTC ATG CTA CTC ATG CGA AAC ATT GTC AGG GTG GTC GTC CTG GAC AAA
 N   A   F   M   L   L   M   R   N   I   V   R   V   V   V   L   D   K

     1793        1802        1811        1820        1829        1838
GTC ACA GAC CTG CTG CTG TTC TTT GGG AAG CTG CTG GTG GTC GGA GGC GTG GGG
 V   T   D   L   L   L   F   F   G   K   L   L   V   V   G   G   V   G

     1847        1856        1865        1874        1883        1892
GTC CTG TCC TTC TTT TTT TTC TCC GGT CGC ATC CCG GGG CTG GGT AAA GAC TTT
 V   L   S   F   F   F   F   S   G   R   I   P   G   L   G   K   D   F
```

FIG. 1D

```
     1901        1910        1919        1928        1937        1946
AAG AGC CCC CAC CTC AAC TAT TAC TGG CTG CCC ATC ATG ACC TCC ATC CTG GGG
--- --- --- --- --- --- --- --- --- --- --- --- --- --- --- --- --- ---
 K   S   P   H   L   N   Y   Y   W   L   P   I   M   T   S   I   L   G

     1955        1964        1973        1982        1991        2000
GCC TAT GTC ATC GCC AGC GGC TTC TTC AGC GTT TTC GGC ATG TGT GTG GAC ACG
--- --- --- --- --- --- --- --- --- --- --- --- --- --- --- --- --- ---
 A   Y   V   I   A   S   G   F   F   S   V   F   G   M   C   V   D   T

     2009        2018        2027        2036        2045        2054
CTC TTC CTC TGC TTC CTG GAA GAC CTG GAG CGG AAC AAC GGC TCC CTG GAC CGG
--- --- --- --- --- --- --- --- --- --- --- --- --- --- --- --- --- ---
 L   F   L   C   F   L   E   D   L   E   R   N   N   G   S   L   D   R

     2063        2072        2081        2090        2099        2108
CCC TAC TAC ATG TCC AAG AGC CTT CTA AAG ATT CTG GGC AAG AAG AAC GAG GCG
--- --- --- --- --- --- --- --- --- --- --- --- --- --- --- --- --- ---
 P   Y   Y   M   S   K   S   L   L   K   I   L   G   K   K   N   E   A

     2117        2126        2135        2144        2153        2162
CCC CCG GAC AAC AAG AAG AGG AAG AAG TGA CAG CTC CGG CCC TGA TCC AGG ACT
--- --- --- --- --- --- --- --- --- --- --- --- --- --- --- --- --- ---
 P   P   D   N   K   K   R   K   K   *

     2171        2180        2189        2198        2207        2216
GCA CCC CAC CCC CAC CGT CCA GCC ATC CAA CCT CAC TTC GCC TTA CAG GTC TCC
--- --- --- --- --- --- --- --- --- --- --- --- --- --- --- --- --- ---
     2225        2234        2243        2252        2261        2270
ATT TTG TGG TAA AAA AAG GTT TTA GGC CAG GCG CCG TGG CTC ACG CCT GTA ATC
--- --- --- --- --- --- --- --- --- --- --- --- --- --- --- --- --- ---
     2279        2288        2297        2306        2315        2324
CAA CAC TTT GAG AGG CTG AGG CGG GCG GAT CAC CTG AGT CAG GAG TTC GAG ACC
--- --- --- --- --- --- --- --- --- --- --- --- --- --- --- --- --- ---
     2333        2342        2351        2360        2369        2378
AGC CTG GCC AAC ATG GTG AAA CCT CCG TCT CTA TTA AAA ATA CAA AAA TTA GCC
--- --- --- --- --- --- --- --- --- --- --- --- --- --- --- --- --- ---
     2387        2396        2405        2414        2423        2432
GAG AGT GGT GGC ATG CAC CTG TCA TCC CAG CTA CTC GGG AGG CTG AGG CAG GAG
--- --- --- --- --- --- --- --- --- --- --- --- --- --- --- --- --- ---
     2441        2450        2459        2468        2477        2486
AAT CGC TTG AAC CCG GGA GGC AGA GGT TGC AGT GAG CCG AGA TCG CGC CAC TGC
--- --- --- --- --- --- --- --- --- --- --- --- --- --- --- --- --- ---
     2495        2504        2513        2522        2531        2540
ACT CCA ACC TGG GTG ACA GAC TCT GTC TCC AAA ACA AAA CAA ACA AAC AAA AAG
--- --- --- --- --- --- --- --- --- --- --- --- --- --- --- --- --- ---
     2549        2558        2567        2576        2585
ATT TTA TTA AAG ATA TTT TGT TAA CTC AGT AAA AAA AAA AAA AAA AA 3'
--- --- --- --- --- --- --- --- --- --- --- --- --- --- --- --
```

FIG. 1E

```
9            18                27                36                45                54
5'  GAT CAG GGC GGC CAG CCA GGT CTC CTG CAC GCT CTG GTA GGC ACT GAG GTT GGT
    --- --- --- --- --- --- --- --- --- --- --- --- --- --- --- --- --- ---
     D   Q   G   G   Q   P   G   L   L   H   A   L   V   G   T   E   V   G

                 63                72                81                90                99               108
    GGT GAA ACC CAG CTG GGA GAT GGA GGC GCC CTC GTC CCG CAG CAC TCG GTA CTC
    --- --- --- --- --- --- --- --- --- --- --- --- --- --- --- --- --- ---
     G   E   T   Q   L   G   D   G   G   A   L   V   P   Q   H   S   V   L

                117               126               135               144               153
    CTC CCA GCA GTA GTA GAT GCC ATA TGC CAG CAC GCC CAG CAC TCC CAG GAT C 3'
    --- --- --- --- --- --- --- --- --- --- --- --- --- --- --- --- --- -
     L   P   A   V   V   D   A   I   C   Q   H   A   Q   H   S   Q   D
```

FIG. 4A

```
24P4C12    5 QRDEDDEAYGKPVKYDPSFRGPIKNRSCTDVICCVLFLLFILGYIVVGIVAWLYGDPRQV
mNG22      3 RKQNENEAHGNSAKYDPSFRGPIKNRGCTDIICCVLFLIFILGYIIVGLVAWVYGDPRQV
                   ** *   ************* *** ******* ****** ** *** *******

24P4C12   65 LYPRNSTGAYCGMGENKDKPYLLYFNIFSCILSSNIISVAENGLQCPTPQVCVSSCPEDP
mNG22     63 LYPRNSTGAYCGVGDNKDKPYVLYFDILSCAAAINIISIAENGLQCPTPQVCVSSCPLAP
             ************ * ****** *** * **    **** ******************  *

24P4C12  125 WTVGKNEFSQTVGEVFYTKNRNFCLPGVPWNMTVITSLQQELCPSFLLPSAPALGRCFPW
mNG22    123 WAVEVFQFSKTVGEV-YGERRNFCLPAVSPDMIVEESLQKGLCPRFLLPSTPALGRCFPL
             * *    ** ***** *   ****** *   * *  ***  *** ***** ********

24P4C12  185 TNVTPPALPGIT-NDTTIQQGISGLIDSLNARDISVKIFEDFAQSWYWILVALGVALVLS
mNG22    182 PNINFTLPEDLRINNTTVSNGISGLLDSINARDVSVKIFEDFAQSWYWILVALGVALALS
              *           * **   ***** ** **** *********************** **

24P4C12  244 LLFILLLRLVAGPLVLVLILGVLGVLAYGIYYCWEEYRVLRDKGASISQLGFTTNLSAYQ
mNG22    242 LLFILLLRLVAAPLVLLLIVGVLAVLAYGIYHCWQQYQVFRDKGASITQLGFTTNFSAYQ
             *********** **** ** *** ******* **  * * ******* ******* ****

24P4C12  304 SVQETWLAALIVLAVLEAILLLMLIFLRQRIRIAIALLKEASKAVGQMMSTMFYPLVTFV
mNG22    302 SVKETWLAALIVLAVLEGILLLMLIFLRQRIRIAIALLKEASRAVGQMMSTMFYPLVTFV
             ** ************** ************************ *****************

24P4C12  364 LLLICIAYWAMTALYLATSGQPQYVLWASNISSPGCEKVPINTSCNPTAHLVNSSCPGLM
mNG22    362 LLVICIGYWAVTALYLATSGQPQYIYWASNTSTPGCENVPVNMTCDPMAPL-NSSCPNLK
             ** *** *** *************  **** * **** ** *  * * * * ***** *

24P4C12  424 CVFQGYSSKGLIQRSVFNLQIYGVLGLFWTLNWVLALGQCVLAGAFASFYWAFHKPQDIP
mNG22    421 CVFKGYSTTGLAQRSLFNLQIYGVLGLFWTVNWVLALGQCVLAGAFASFYWAFHKPRDIP
             *** ***  ** *** ************** ************************* ***

24P4C12  484 TFPLISAFIRTLRYHTGSLAFGALILTLVQIARVILEYIDHKLRGVQNPVARCIMCCFKC
mNG22    481 TFPLSSAFIRTLRYHTGSLAFGALILSLVQIARVILEYIDHKLRGSQNPVARCIICCFKC
             **** ********************* ****************** ******** *****

24P4C12  544 CLWCLEKFIKFLNRNAYIMIAIYGKNFCVSAKNAFMLLMRNIVRVVVLDKVTDLLLFFGK
mNG22    541 CLWCLEKFIKFLNRNAYIMIAIYGKNFCVSAKNAFMLLMRNVLRVVVLDKVTDLLLFFGK
             *****************************************  *****************
```

FIG. 4B

```
24P4C12    604 LLVVGGVGVLSFFFFSGRIPGLGKDFKSPHLNYYWLPIMTSILGAYVIASGFFSVFGMCV

mNG22      601 LLVVGGVGVLSFFFFSGRIKGLGKDFENPNLNYYWLPIMTSIMGAYVIASGFFSVFGMCV
               ******************* ******  * ************ *****************

24P4C12    664 DTLFLCFLEDLERNNGSLDRPYYMSKSLLKILGKKNEAPPDNKKRKK

mNG22      661 DTLFLCFLEDLERNDGSQERPYYMPKALLKILGKKNEAPTGGKTRKK
               ************** **  ***** * ************    * ***
```

β-actin

FIG. 7A

```
            10          19          28          37          46          55
5'  GCC CGC CCG GGC TGG GGT CGC GCT GGC TCG GAC TCC GCT CCC CGC CCC GCC GCG

            64          73          82          91         100         109
    GCC ATG GAG GAC GAG CGG AAA AAC GGA GCC TAC GGA ACG CCA CAG AAG TAT GAT
         M   E   D   E   R   K   N   G   A   Y   G   T   P   Q   K   Y   D

           118         127         136         145         154         163
    CCC ACT TTC AAA GGA CCC ATT TAC AAT AGG GGC TGC ACG GAT ATC ATA TGC TGT
     P   T   F   K   G   P   I   Y   N   R   G   C   T   D   I   I   C   C

           172         181         190         199         208         217
    GTG TTC CTG CTC CTG GCC ATT GTG GGC TAC GTG GCT GTA GGC ATC ATA GCC TGG
     V   F   L   L   L   A   I   V   G   Y   V   A   V   G   I   I   A   W

           226         235         244         253         262         271
    ACT CAT GGA GAC CCT CGA AAG GTG ATC TAC CCC ACT GAT AGC CGG GGC GAG TTC
     T   H   G   D   P   R   K   V   I   Y   P   T   D   S   R   G   E   F

           280         289         298         307         316         325
    TGC GGG CAG AAG GGC ACA AAA AAC GAG AAC AAA CCC TAT CTG TTT TAT TTC AAC
     C   G   Q   K   G   T   K   N   E   N   K   P   Y   L   F   Y   F   N

           334         343         352         361         370         379
    ATT GTG AAA TGT GCC AGC CCC CTG GTT CTG CTG GAA TTC CAA TGT CCC ACT CCC
     I   V   K   C   A   S   P   L   V   L   L   E   F   Q   C   P   T   P

           388         397         406         415         424         433
    CAG ATC TGC GTG GAA AAA TGC CCC GAC CGC TAC CTC ACG TAC CTG AAT GCT CGC
     Q   I   C   V   E   K   C   P   D   R   Y   L   T   Y   L   N   A   R

           442         451         460         469         478         487
    AGC TCC CGG GAC TTT GAG TAC TAT AAG CAG TTC TGT GTT CCT GGC TTC AAG AAC
     S   S   R   D   F   E   Y   Y   K   Q   F   C   V   P   G   F   K   N

           496         505         514         523         532         541
    AAT AAA GGA GTG GCT GAG GTG CTT CGA GAT GGT GAC TGC CCT GCT GTC CTC ATC
     N   K   G   V   A   E   V   L   R   D   G   D   C   P   A   V   L   I

           550         559         568         577         586         595
    CCC AGC AAA CCC TTG GCC CGG AGA TGC TTC CCC GCT ATC CAC GCC TAC AAG GGT
     P   S   K   P   L   A   R   R   C   F   P   A   I   H   A   Y   K   G

           604         613         622         631         640         649
    GTC CTG ATG GTG GGC AAT GAG ACG ACC TAT GAG GAT GGG CAT GGC TCC CGG AAA
     V   L   M   V   G   N   E   T   T   Y   E   D   G   H   G   S   R   K
```

FIG. 7B

```
        658         667         676         685         694         703
AAC ATC ACA GAC CTG GTG GAG GGC GCC AAG AAA GCC AAT GGA GTC CTA GAG GCG
 N   I   T   D   L   V   E   G   A   K   K   A   N   G   V   L   E   A

        712         721         730         739         748         757
CGG CAA CTC GCC ATG CGC ATA TTT GAA GAT TAC ACC GTC TCT TGG TAC TGG ATT
 R   Q   L   A   M   R   I   F   E   D   Y   T   V   S   W   Y   W   I

        766         775         784         793         802         811
ATC ATA GGC CTG GTC ATT GCC ATG GCG ATG AGC CTC CTG TTC ATC ATC CTG CTT
 I   I   G   L   V   I   A   M   A   M   S   L   L   F   I   I   L   L

        820         829         838         847         856         865
CGC TTC CTG GCT GGT ATT ATG GTC TGG GTG ATG ATC ATC ATG GTG ATT CTG GTG
 R   F   L   A   G   I   M   V   W   V   M   I   I   M   V   I   L   V

        874         883         892         901         910         919
CTG GGC TAC GGA ATA TTT CAC TGC TAC ATG GAG TAC TCC CGA CTG CGT GGT GAG
 L   G   Y   G   I   F   H   C   Y   M   E   Y   S   R   L   R   G   E

        928         937         946         955         964         973
GCC GGC TCT GAT GTC TCT TTG GTG GAC CTC GGC TTT CAG ACG GAT TTC CGG GTG
 A   G   S   D   V   S   L   V   D   L   G   F   Q   T   D   F   R   V

        982         991        1000        1009        1018        1027
TAC CTG CAC TTA CGG CAG ACC TGG TTG GCC TTT ATG ATC ATT CTG AGT ATC CTT
 Y   L   H   L   R   Q   T   W   L   A   F   M   I   I   L   S   I   L

       1036        1045        1054        1063        1072        1081
GAA GTC ATT ATC ATC TTG CTG CTC ATC TTT CTC CGG AAG AGA ATT CTC ATC GCG
 E   V   I   I   I   L   L   L   I   F   L   R   K   R   I   L   I   A

       1090        1099        1108        1117        1126        1135
ATT GCA CTC ATC AAA GAA GCC AGC AGG GCT GTG GGA TAC GTC ATG TGC TCC TTG
 I   A   L   I   K   E   A   S   R   A   V   G   Y   V   M   C   S   L

       1144        1153        1162        1171        1180        1189
CTC TAC CCA CTG GTC ACC TTC TTC TTG CTG TGC CTC TGC ATC GCC TAC TGG GCC
 L   Y   P   L   V   T   F   F   L   L   C   L   C   I   A   Y   W   A

       1198        1207        1216        1225        1234        1243
AGC ACT GCT GTC TTC CTG TCC ACT TCC AAC GAA GCG GTC TAT AAG ATC TTT GAT
 S   T   A   V   F   L   S   T   S   N   E   A   V   Y   K   I   F   D

       1252        1261        1270        1279        1288        1297
GAC AGC CCC TGC CCA TTT ACT GCG AAA ACC TGC AAC CCA GAG ACC TTC CCC TCC
 D   S   P   C   P   F   T   A   K   T   C   N   P   E   T   F   P   S
```

FIG. 7C

```
      1306        1315        1324        1333        1342        1351
TCC CAT GAG TCC CGC CAA TGC CCC AAT GCC CGT TGC CAG TTC GTC TTC TAC GGT
--- --- --- --- --- --- --- --- --- --- --- --- --- --- --- --- --- ---
 S   H   E   S   R   Q   C   P   N   A   R   C   Q   F   V   F   Y   G

      1360        1369        1378        1387        1396        1405
GGT GAG TCG GGC TAC CAC CGG GCC CTG CTG GGC CTG CAG ATC TTC AAT GCC TTC
--- --- --- --- --- --- --- --- --- --- --- --- --- --- --- --- --- ---
 G   E   S   G   Y   H   R   A   L   L   G   L   Q   I   F   N   A   F

      1414        1423        1432        1441        1450        1459
ATG TTC TTC TGG TTG GCC AAC TTC GTG CTG GCG CTG GGC CAG GTC ACG CTG GCC
--- --- --- --- --- --- --- --- --- --- --- --- --- --- --- --- --- ---
 M   F   F   W   L   A   N   F   V   L   A   L   G   Q   V   T   L   A

      1468        1477        1486        1495        1504        1513
GGG GCC TTT GCC TCC TAC TAC TGG GCC CTG CGC AAG CCG GAC GAC CTG CCG GCC
--- --- --- --- --- --- --- --- --- --- --- --- --- --- --- --- --- ---
 G   A   F   A   S   Y   Y   W   A   L   R   K   P   D   D   L   P   A

      1522        1531        1540        1549        1558        1567
TTC CCG CTC TTC TCT GCC TTT GGC CGG GCG CTC AGG TAC CAC ACA GGC TCC CTG
--- --- --- --- --- --- --- --- --- --- --- --- --- --- --- --- --- ---
 F   P   L   F   S   A   F   G   R   A   L   R   Y   H   T   G   S   L

      1576        1585        1594        1603        1612        1621
GCC TTT GGC GCG CTC ATC CTG GCC ATT GTG CAG ATC ATC CGT GTG ATA CTC GAG
--- --- --- --- --- --- --- --- --- --- --- --- --- --- --- --- --- ---
 A   F   G   A   L   I   L   A   I   V   Q   I   I   R   V   I   L   E

      1630        1639        1648        1657        1666        1675
TAC CTG GAT CAG CGG CTG AAA GCT GCA GAG AAC AAG TTT GCC AAG TGC CTC ATG
--- --- --- --- --- --- --- --- --- --- --- --- --- --- --- --- --- ---
 Y   L   D   Q   R   L   K   A   A   E   N   K   F   A   K   C   L   M

      1684        1693        1702        1711        1720        1729
ACC TGT CTC AAA TGC TGC TTC TGG TGC CTG GAG AAG TTC ATC AAA TTC CTT AAT
--- --- --- --- --- --- --- --- --- --- --- --- --- --- --- --- --- ---
 T   C   L   K   C   C   F   W   C   L   E   K   F   I   K   F   L   N

      1738        1747        1756        1765        1774        1783
AGG AAT GCC TAC ATC ATG ATT GCC ATC TAC GGC ACC AAT TTC TGC ACC TCG GCC
--- --- --- --- --- --- --- --- --- --- --- --- --- --- --- --- --- ---
 R   N   A   Y   I   M   I   A   I   Y   G   T   N   F   C   T   S   A

      1792        1801        1810        1819        1828        1837
AGG AAT GCC TTC TTC CTG CTC ATG AGA AAC ATC ATC AGA GTG GCT GTC CTG GAT
--- --- --- --- --- --- --- --- --- --- --- --- --- --- --- --- --- ---
 R   N   A   F   F   L   L   M   R   N   I   I   R   V   A   V   L   D

      1846        1855        1864        1873        1882        1891
AAA GTT ACT GAC TTC CTC TTC CTG TTG GGC AAA CTT CTG ATC GTT GGT AGT GTG
--- --- --- --- --- --- --- --- --- --- --- --- --- --- --- --- --- ---
 K   V   T   D   F   L   F   L   L   G   K   L   L   I   V   G   S   V

      1900        1909        1918        1927        1936        1945
GGG ATC CTG GCT TTC TTC TTC TTC ACC CAC CGT ATC AGG ATC GTG CAG GAT ACA
--- --- --- --- --- --- --- --- --- --- --- --- --- --- --- --- --- ---
 G   I   L   A   F   F   F   F   T   H   R   I   R   I   V   Q   D   T
```

FIG. 7D

```
     1954        1963        1972        1981        1990        1999
GCA CCA CCC CTC AAT TAT TAC TGG GTT CCT ATA CTG ACG GTG ATC GTT GGC TCC
--- --- --- --- --- --- --- --- --- --- --- --- --- --- --- --- --- ---
 A   P   P   L   N   Y   Y   W   V   P   I   L   T   V   I   V   G   S

     2008        2017        2026        2035        2044        2053
TAC TTG ATT GCA CAC GGT TTC TTC AGC GTC TAT GGC ATG TGT GTG GAC ACG CTG
--- --- --- --- --- --- --- --- --- --- --- --- --- --- --- --- --- ---
 Y   L   I   A   H   G   F   F   S   V   Y   G   M   C   V   D   T   L

     2062        2071        2080        2089        2098        2107
TTC CTC TGC TTC TTG GAG GAC CTG GAG AGG AAT GAC GGC TCG GCC GAG AGG CCT
--- --- --- --- --- --- --- --- --- --- --- --- --- --- --- --- --- ---
 F   L   C   F   L   E   D   L   E   R   N   D   G   S   A   E   R   P

     2116        2125        2134        2143        2152        2161
TAC TTC ATG TCT TCC ACC CTC AAG AAA CTC TTG AAC AAG ACC AAC AAG AAG GCA
--- --- --- --- --- --- --- --- --- --- --- --- --- --- --- --- --- ---
 Y   F   M   S   S   T   L   K   K   L   L   N   K   T   N   K   K   A

     2170        2179        2188        2197        2206        2215
GCG GAG TCC TGA AGG CCC CGT GCT CCC CAC CTC TCA AGG AGT CTC ATG CCG CAG
--- --- --- --- --- --- --- --- --- --- --- --- --- --- --- --- --- ---
 A   E   S   *

     2224        2233        2242        2251        2260        2269
GGT GCT CAG TAG CTG GGT CTG TTC CCC CAG CCC CTT GGG CTC ACC TGA AGT CCT
--- --- --- --- --- --- --- --- --- --- --- --- --- --- --- --- --- ---
     2278        2287        2296        2305        2314        2323
ATC ACT GCC GCT CTG CCC CTC CCC ATG AGC CAG ATC CCA CCA GTT TCT GGA CGT
--- --- --- --- --- --- --- --- --- --- --- --- --- --- --- --- --- ---
     2332        2341        2350        2359        2368        2377
GGA GAG TCT GGG GCA TCT CCT TCT TAT GCC AAG GGG CGC TTG GAG TTT TCA TGG
--- --- --- --- --- --- --- --- --- --- --- --- --- --- --- --- --- ---
     2386        2395        2404        2413        2422        2431
CTG CCC CTC CAG ACT GCG AGA AAC AAG TAA AAA CCC ATT GGG GCC TCT TGA TGT
--- --- --- --- --- --- --- --- --- --- --- --- --- --- --- --- --- ---
     2440        2449        2458        2467        2476        2485
CTG GGA TGG CAC GTG GCC CGA CCT CCA CAA GCT CCC TCA TGC TTC CTG TCC CCC
--- --- --- --- --- --- --- --- --- --- --- --- --- --- --- --- --- ---
     2494        2503        2512        2521        2530        2539
GCT TAC ACG ACA ACG GGC CAG ACC ACG GGA AGG ACG GTG TTT GTG TCT GAG GGA
--- --- --- --- --- --- --- --- --- --- --- --- --- --- --- --- --- ---
     2548        2557        2566        2575        2584        2593
GCT GCT GGC CAC AGT GAA CAC CCA CGT TTA TTC CTG CCT GCT CCG GCC AGG ACT
--- --- --- --- --- --- --- --- --- --- --- --- --- --- --- --- --- ---
     2602        2611        2620        2629        2638        2647
GAA CCC CTT CTC CAC ACC TGA ACA GTT GGC TCA AGG GCC ACC AGA AGC ATT TCT
--- --- --- --- --- --- --- --- --- --- --- --- --- --- --- --- --- ---
     2656        2665        2674        2683        2692        2701
TTA TTA TTA TTA TTT TTT AAC CTG GAC ATG CAT TAA AGG GTC TAT TAG CTT TCA
--- --- --- --- --- --- --- --- --- --- --- --- --- --- --- --- --- ---
     2710        2719        2728        2737
AAA AAA AAA AAA AAA AAA AAA AAA AAA AAA AAA AAA A 3'
--- --- --- --- --- --- --- --- --- --- --- --- -
```

FIG. 8

```
Score =  589 bits (1502), Expect = e-167
Identities = 317/707 (44%), Positives = 408/707 (56%), Gaps = 34/707 (4%)

24P4C12 12   AYGKPVKYDPSFRGPIKNRSCTDVICCVLFLLFILGYIVVGIVAWLYGDPRQVLYPRNST 71
             AYG P KYDP+F+GPI NR CTD+ICCV  LL I+GY+ VGI+AW +GDPR+V+YP +S
H38087  9    AYGTPQKYDPTFKGPIYNRGCTDIICCVFLLLAIVGYVAVGIIAWTHGDPRKVIYPTDSR 68

24P4C12 72   GAYCGMG--ENKDKPYLLYFNIFSCILSSNIISVAENGLQCPTPQVCVSSCPEDPWTVGK 129
             G +CG    +N++KPYL YFNI  C     ++       QCPTPQ+CV  CP D +
H38087  69   GEFCGQKGTKNENKPYLFYFNIVKCASPLVLLE-----FQCPTPQICVEKCP-DRYLTYL 122

24P4C12 130  NEFSQTVGEVFYTKNRNFCLPGVPWNMTVITSLQQELCPSFLLPSAPALGRCFPWTNVTP 189
             N  S    E +    + FC+PG   N  V   L+   CP+ L+PS P   RCFP  +
H38087  123  NARSSRDFEYY----KQFCVPGFKNNKGVAEVLRDGDCPAVLIPSKPLARRCFPAIHAYK 178

24P4C12 190  PALPGITNDTTIQQG------ISGLIDS-------LNARDISVKIFEDFAQSWYWIXXXX 236
               L  + N+TT + G      I+ L++        L AR ++++IFED+  SWYWI
H38087  179  GVLM-VGNETTYEDGHGSRKNITDLVEGAKKANGVLEARQLAMRIFEDYTVSWYWIIIGL 237

24P4C12 237  XXXXXXXXXXXXXXXXXXXXXXXXXXXXXXXXXXXXXXYCWEEYRVLRDKGAS---ISQL 293
                                                   +C+ EY  LR +  S   +  L
H38087  238  VIAMAMSLLFIILLRFLAGIMVWVMIIMVILVLGYGIFHCYMEYSRLRGEAGSDVSLVDL 297

24P4C12 294  GFTTNLSAYQSVQETWXXXXXXXXXXXXXXXXXXXXXRQRIRIAIALLKEASKAVGQMMS 353
             GF T+   Y  +++TW                     R+RI IAIAL+KEAS+AVG +M
H38087  298  GFQTDFRVYLHLRQTWLAFMIILSILEVIIILLLIFLRKRILIAIALIKEASRAVGYVMC 357

24P4C12 354  TMFYPLVTFVLLLICIAYWAMTALYLATSGQPQYVLWASNISSPGCEKVPINTSCNPTAH 413
             ++ YPLVTF LL +CIAYWA TA++L+TS +  Y ++  +   P   K   N    P++H
H38087  358  SLLYPLVTFFLLCLCIAYWASTAVFLSTSNEAVYKIFDDS-PCPFTAKT-CNPETFPSSH 415

24P4C12 414  LVNSSCPGLMCVFQGYSSKGLIQRSVFNLQIYGVLGLFWTLNWVLALGQCVLAGAFASFY 473
               +  CP   C F  Y  +    R++  LQI+     FW  N+VLALGQ  LAGAFAS+Y
H38087  416  -ESRQCPNARCQFVFYGGESGYHRALLGLQIFNAFMFFWLANFVLALGQVTLAGAFASYY 474

24P4C12 474  WAFHKPQDIPTFPLISAFIRTLRYHTGSLAFGALILTLVQIARVILEYIDHKLRGVQNPV 533
             WA  KP D+P FPL SAF R LRYHTGSLAFGALIL +VQI RVILEY+D +L+  +N
H38087  475  WALRKPDDLPAFPLFSAFGRALRYHTGSLAFGALILAIVQIIRVILEYLDQRLKAAENKF 534

24P4C12 534  ARCIMCCFKCCLWCLEKFIKFLNRNAYIMIAIYGKNFCVSAKNAFMLLMRNIXXXXXXXX 593
             A+C+M C KCC WCLEKFIKFLNRNAYIMIAIYG NFC SA+NAF LLMRNI
H38087  535  AKCLMTCLKCCFWCLEKFIKFLNRNAYIMIAIYGTNFCTSARNAFFLLMRNIIRVAVLDK 594

24P4C12 594  XXXXXXXXXXXXXXXXXXXXXXXXXXXRIPGLGKDFKSPHLNYYWLPIMTSILGAYVIAS 653
                                        RI  + +D  +P LNYYW+PI+T I+G+Y+IA
H38087  595  VTDFLFLLGKLLIVGSVGILAFFFFTHRI-RIVQD-TAPPLNYYWVPILTVIVGSYLIAH 652

24P4C12 654  GFFSVFGMCVDTLFLCFLEDLERNNGSLDRPYYMSKSLLKILGKKNE 700
             GFFSV+GMCVDTLFLCFLEDLERN+GS +RPY+MS +L K+L K N+
H38087  653  GFFSVYGMCVDTLFLCFLEDLERNDGSAERPYFMSSTLKKLLNKTNK 699
```

13-TRANSMEMBRANE PROTEIN EXPRESSED IN PROSTATE CANCER

CROSS-REFERENCE TO RELATED APPLICATIONS

This application is a continuation of U.S. Ser. No. 09/547,789, filed Apr. 12, 2000, and now U.S. Pat. No. 6,943,235, which claims the benefit of U.S. provisional application No. 60/128,858, filed Apr. 12, 1999. The contents of these applications are incorporated herein by reference.

FIELD OF THE INVENTION

The invention described herein relates to a novel gene and its encoded protein, termed 24P4C12, and to diagnostic and therapeutic methods and compositions useful in the management of various cancers that express 24P4C12, particularly prostate cancers.

BACKGROUND OF THE INVENTION

Cancer is the second leading cause of human death next to coronary disease. Worldwide, millions of people die from cancer every year. In the United States alone, cancer causes the death of well over a half-million people annually, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Many cancer patients experience a recurrence.

Worldwide, prostate cancer is the fourth most prevalent cancer in men. In North America and Northern Europe, it is by far the most common male cancer and is the second leading cause of cancer death in men. In the United States alone, well over 40,000 men die annually of this disease—second only to lung cancer. Despite the magnitude of these figures, there is still no effective treatment for metastatic prostate cancer. Surgical prostatectomy, radiation therapy, hormone ablation therapy, and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the management of this disease. Although the serum PSA assay has been a very useful tool, its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic disease progression, including the transition from androgen dependence to androgen independence and the development of metastatic lesions (Klein et al., 1997, Nat. Med. 3:402). More recently identified prostate cancer markers include PCTA-1 (Su et al., 1996, Proc. Natl. Acad. Sci. USA 93: 7252), prostate stem cell antigen (PSCA) (Reiter et al., 1998, Proc. Natl. Acad. Sci. USA 95: 1735), and STEAP (Hubert et al., 1999, Proc. Natl. Acad. Sci. USA 96: 14523).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

SUMMARY OF THE INVENTION

The present invention relates to a novel family of genes and proteins, characterized by multiple transmembrane regions and expression in prostate cancer. More particularly, the invention provides a novel gene and protein, termed 24P4C12. The 24P4C12 gene encodes a 710 amino acid protein containing 13 transmembrane domains and bearing homology to murine and *C. elegans* genes containing 12 transmembrane domains. The nucleotide and encoded amino acid sequences of the entire coding and partial non-coding regions of the human 24P4C12 gene are shown in FIGS. 1A-1D (SEQ ID NOS: 1, 2). RT-PCR and Northern blot analyses show expression of 24P4C12 in normal colon, prostate, kidney and lung, and in prostate cancer xenografts. The transmembrane nature of the 24P4C12 protein, combined with its expression in prostate cancer, suggest that 24P4C12 is a target for prostate cancer therapy using, for example, antibodies and other small molecules capable of binding to and modulating the 24P4C12 protein in vivo. In addition, because of its location on the cell surface of prostate cancer cells, antibodies and other agents capable of detecting 24P4C12 protein can be useful in prostate cancer imaging methods. Various other molecular detection assays using, for example, polynucleotide probes and primers capable of detecting 24P4C12 transcription products, may also find use in diagnosing, monitoring, prognosing, and staging prostate cancer and potentially other cancers.

The invention provides polynucleotides corresponding or complementary to the 24P4C12 gene, mRNA, or fragments thereof, including cDNAs, RNAs, oligonucleotide probes, and primers. The invention further provides methods for detecting the presence of 24P4C12 polynucleotides in various biological samples. Molecular diagnostic assays for prostate cells using 24P4C12 polynucleotides are also provided. Such assays may provide diagnostic and/or prognostic information concerning the presence and degree of prostate cancer. The invention further provides means for isolating cDNAs and the gene encoding 24P4C12, as well as those encoding mutated and other forms of 24P4C12. Recombinant DNA molecules containing 24P4C12 polynucleotides, cells transformed or transduced with such molecules, and host-vector systems for the expression of 24P4C12 gene products are also provided. The invention further provides 24P4C12 proteins and polypeptide fragments thereof. The invention further provides antibodies that bind to 24P4C12 proteins and polypeptide fragments thereof, including polyclonal and monoclonal antibodies, murine and other mammalian antibodies, chimeric antibodies, humanized and fully human antibodies, and antibodies labeled with a detectable marker.

The invention further provides methods for detecting the presence and status of 24P4C12 polynucleotides and proteins in various biological samples, as well as methods for identifying cells that express 24P4C12. A typical embodiment of this invention provides methods for monitoring 24P4C12 gene products in a tissue sample having or suspected of having some form of growth disregulation such as cancer.

The invention further provides various therapeutic compositions and strategies for treating cancers that express 24P4C12 such as cancer of the prostate, including therapies aimed at inhibiting the transcription, translation, processing or function of 24P4C12 as well as cancer vaccines.

In addition, the invention provides a novel gene and protein related to 24P4C12, termed H38087. The H38087 gene encodes a 704 amino acid protein containing 11 potential transmembrane domains. The nucleotide and encoded amino acid sequences of the entire coding and partial non-coding regions of the human H38087 gene are shown in FIGS. 7A-7D (SEQ ID NOS: 6, 7). The 58 base pairs of 5' untranslated region are very GC rich (87%), indicating that this gene may contain translational regulatory elements. The amino acid sequences of 24P4C12 and H38087 are 44% identical and 56% homologous over the entire sequence (FIG. 8). Expression analysis shows that H38087 is ubiquitously expressed (FIG. 9), with highest expression levels detected in testis. Expression is also observed in each of the various LAPC xenografts examined. H38087 could serve as a control for testing 24P4C12-specific therapeutics, or provide a diagnostic and/or therapeutic target. A therapeutic that selectively affects 24P4C12, but not H38087, may be less toxic to normal cells. Therefore, H38087 protein may be useful as a pre-clinical testing tool for therapeutic modalities directed towards 24P4C12. H38087 protein expression, however, may be less ubiquitous than its RNA expression, suggesting H38087 as a target for diagnostic and therapeutic strategies.

The invention additionally provides a method for identifying a 24P4C12 specific binding agent. The method comprises contacting a candidate agent that binds 24P4C12 with H38087, and determining whether the candidate agent binds H38087. A lack of binding of the candidate agent to H38087 being indicative of 24P4C12 specificity. Such binding can be detected using conventional binding assays known in the art, including representative assays described herein.

BRIEF DESCRIPTION OF THE FIGURES

FIGS. 1A-1D. Nucleotide (SEQ ID NO: 1) and deduced amino acid (SEQ ID NO: 2) sequences of entire coding region (and part of the 3' non-coding region) of the 24P4C12 gene. This sequence was generated from the overlapping sequences of three cDNA clones, designated 24P4C12-GTE9, 24P4C12-GTE5 and 24P4C12-GTE4 (Example 2). Thirteen potential transmembrane domains are underlined in bold. A Kozak sequence and putative start methionine are indicated in bold.

FIG. 1E. Nucleotide (SEQ ID NO: 3) and ORF amino acid (SEQ ID NO: 4) sequences of the initially isolated SSH fragment of the 24P4C12 gene.

FIGS. 4A-4B. Amino acid sequence alignment of the 24P4C12 gene product and murine NG22 (SEQ ID NO: 5).

FIGS. 7A-7D. The cDNA (SEQ ID NO: 6) and amino acid (SEQ ID NO: 7) sequence of H38087 (clone GTB6). A GC rich (87% GC content) region in the 5' untranslated (UTR) region is shown prior to the potential Kozak sequence and start methionine, which are indicated in bold. The potential transmembrane domains are underlined in bold.

FIG. 8. Homology alignment of 24P4C12 with H38087 using the BLAST function (NCBI).

DETAILED DESCRIPTION OF THE INVENTION

Figure 2A:
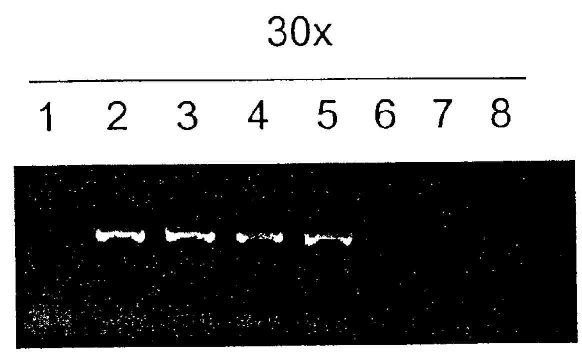
FIG. 2A. RT-PCR analysis of 24P4C12 gene expression in prostate cancer xenografts, normal prostate, and other tissues and cell lines, showing approximately equal levels of expression in normal prostate and the LAPC prostate cancer xenografts. Lanes represent the following tissues: (1) brain; (2) prostate; (3) LAPC-4 AD; (4) LAPC-4 AI; (5) LAPC-9 AD; (6) HeLa; (7) murine cDNA; and (8) negative control.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

As used herein, the terms "metastatic prostate cancer" and "metastatic disease" mean prostate cancers that have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is the preferred treatment modality. Patients with metastatic prostate cancer eventually develop an androgen-refractory state within 12 to 18 months of treatment initiation, and approximately half of these patients die within 6 months thereafter. The most common site for prostate cancer metastasis is bone. Prostate cancer bone metastases are, on balance, characteristically osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA.

As used herein, the term "polypeptide" means a polymer of at least 10 amino acids. Throughout the specification, standard three letter or single letter designations for amino acids are used.

As used herein, the terms "hybridize", "hybridizing", "hybridizes" and the like, used in the context of polynucleotides, are meant to refer to conventional hybridization conditions, preferably such as hybridization in 50% formamide/6×SSC/0.1% SDS/100 μg/ml ssDNA, in which temperatures for hybridization are above 37 degrees C. and temperatures for washing in 0.1×SSC/0.1% SDS are above 55 degrees C., and most preferably to stringent hybridization conditions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In the context of amino acid sequence comparisons, the term "identity" is used to express the percentage of amino acid residues at the same relative positions that are the same. Also in this context, the term "homology" is used to express the percentage of amino acid residues at the same relative positions that are either identical or are similar, using the conserved amino acid criteria of BLAST analysis, as is generally understood in the art. For example, % identity values may be generated by WU-BLAST-2 (Altschul et al., Methods in Enzymology, 266: 460-480 (1996): http://blast.wustl/edu/blast/README.html). Further details regarding amino acid substitutions, which are considered conservative under such criteria, are provided below.

Additional definitions are provided throughout the subsections that follow.

The present invention relates to a novel family of genes and proteins, characterized by multiple transmembrane regions and expression in prostate cancer. More particularly, the invention provides novel genes and proteins, designated 24P4C12 and H38087. The invention is based, in part, on the identification of the 24P4C12 and H38087 genes and on the characterization of the 24P4C12 and H38087 gene expression patterns in prostate cancer, normal prostate, and other normal human tissues. As described more fully in the examples that follow, the expression pattern of the 24P4C12 and H38087 genes was analyzed by: (1) differential expression analysis by RT-PCR using target cDNAs prepared from a panel of tissues and cell lines including normal prostate, and the LAPC-4 AD and AI, and LAPC-9 AD xenografts, (2) tissue specificity analysis by RT-PCR using cDNAs prepared from 16 normal human tissues, and (3) northern blot analysis of normal prostate and prostate cancer xenograft samples. This combined expression analysis was designed to provide information on differential expression between AD and AI tissue, clinical prostate cancer and normal prostate, and tissue specificity. In addition, initial biological characterization of the 24P4C12 and H38087 gene products was undertaken by comparative sequence analysis.

Nucleotide probes corresponding to all or part of the 24P4C12 and H38087 cDNAs and gene sequences disclosed herein are provided and may be used to isolate or identify other cDNAs encoding all or part of the 24P4C12 and H38087 gene sequences. The invention further provided primers capable of specifically amplifying the 24P4C12 and H38087 genes or their RNA transcripts, and for differentiating between 24P4C12 and H38087 molecules. The invention further provides isolated polynucleotides containing coding sequences of the 24P4C12 and H38087 gene product(s). Such polynucleotides may be used to express 24P4C12 and H38087 encoded proteins and peptides having a number of further uses. 24P4C12 and H38087 gene probes and primers may also be used to detect the presence or absence of 24P4C12 and H38087 mRNA in various biological samples, for detecting prostate cancer cells and other cells expressing 24P4C12 and H38087, and in molecular diagnostic and prognostic assays for prostate cancer. Polynucleotides corresponding or complementary to the 24P4C12 gene may be useful in methods for treating prostate cancer, such as, for example, in modulating or inhibiting 24P4C12 biological activity.

The invention also provides 24P4C12 and H38087 proteins and polypeptides that may be used, for example, to generate antibodies. Antibodies capable of specifically binding to and identifying 24P4C12 and H38087 proteins or polypeptides may be used to detect the expression of 24P4C12 and H38087, determine their subcellular location, detect and image prostate cancer cells and prostate tumors, and modulate or inhibit 24P4C12 and H38087 biological activity. These and other aspects of the invention are described in greater detail in the subsections that follow.

Structure and Expression of 24P4C12

As is further described in the Examples that follow, the 24P4C12 genes and proteins have been characterized using a number of analytical approaches. For example, analyses of nucleotide coding and amino acid sequences were conducted in order to identify potentially related molecules, as well as recognizable structural domains, topological features, and other elements within the 24P4C12 mRNA and protein structures. Northern blot analyses of 24P4C12 mRNA expression was conducted in order to establish the range of normal and cancerous tissues expressing 24P4C12 message.

The nucleotide (SEQ ID NO: 1) and deduced amino acid (SEQ ID NO: 2) sequences of an approximately 3 kb 24P4C12 combined cDNA sequence are provided in FIGS. 1A-1D. This 2587 nucleotide sequence encodes a protein of 710 amino acids, which contains 13 putative transmembrane domains (underlined in FIGS. 1A-1D, and numbered therein as 105-173, 261-329, 439-506, 678-746, 768-836, 924-992, 1074-1142, 1245-1313, 1344-1412, 1506-1575, 1694-1763, 1803-1871, and 1935-2000). Comparative sequence analysis identified two known genes with significant homology to the 24P4C12 cDNA sequence, the recently identified murine NG22 gene and the *C. elegans* gene designated CEESB82F. Both of these genes encode proteins containing 12 transmembrane domains. The murine NG22 gene (FIGS. 4A-4B; SEQ ID NO: 5) was recently identified as one of many ORFs within a genomic BAC clone that encompasses the MHC class III in the mouse genome.

Figure 2B:
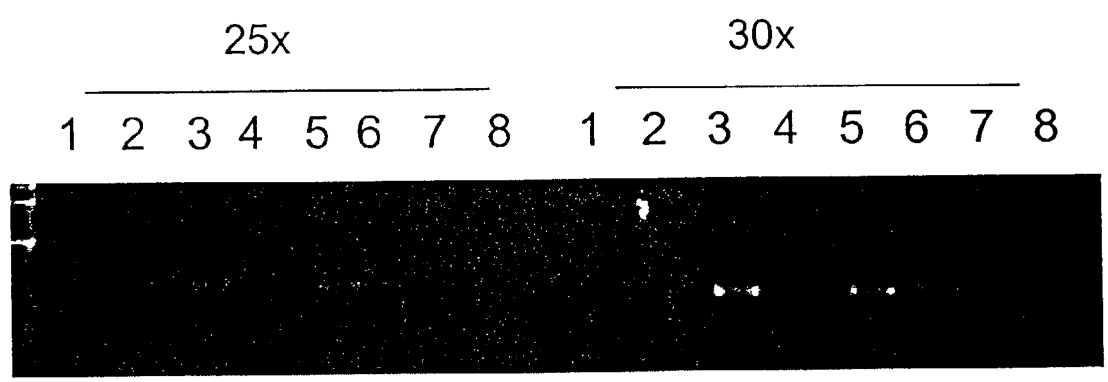
FIG. 2B. RT-PCR analysis of 24P4C12 gene expression in various tissues, showing detectable expression only in normal kidney and lung after 25 cycles of PCR amplification. Lower level expression is detectable in a variety of other tissues after 30 cycles of amplification. Lanes represent the following tissues: (1) brain; (2) heart; (3) kidney; (4) liver; (5) lung; (6) pancreas; (7) placenta; and (8) skeletal muscle.
Figure 2C:
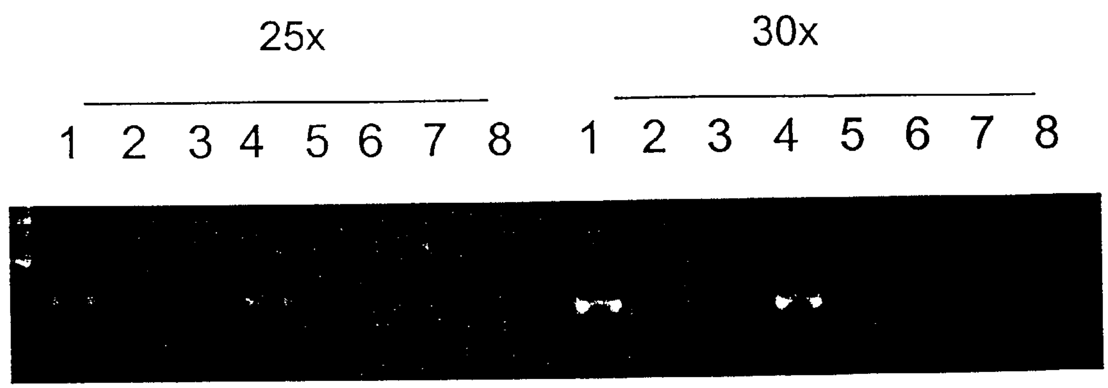
FIG. 2C. RT-PCR analysis of 24P4C12 gene expression in various tissues, showing detectable expression only in normal colon and prostate after 25 cycles of PCR amplification. Lower level expression is detectable in a variety of other tissues after 30 cycles of amplification. Lanes represent the following tissues: (1) colon; (2) ovary; (3) leukocytes; (4) prostate; (5) small intestine; (6) spleen; (7) testis; and (8) thymus.
Figure 3A:
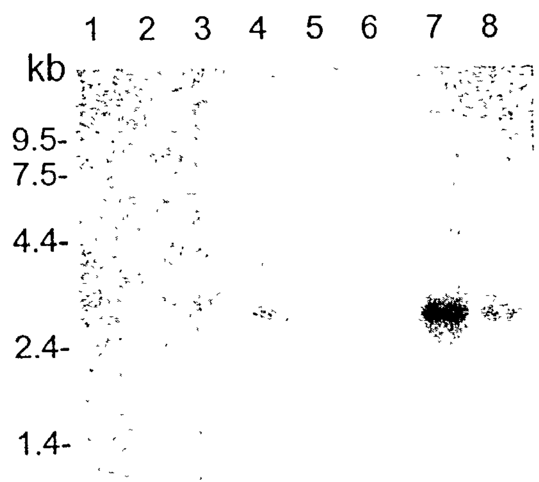
FIG. 3A. Northern blot analysis of 24P4C12 expression across a panel of normal human tissues, showing expression of an approximately 3 kb transcript in kidney. Lanes represent the following tissues: (1) heart; (2) brain; (3) placenta; (4) lung; (5) liver; (6) skeletal muscle; (7) kidney; and (8) pancreas.
Figure 3B:
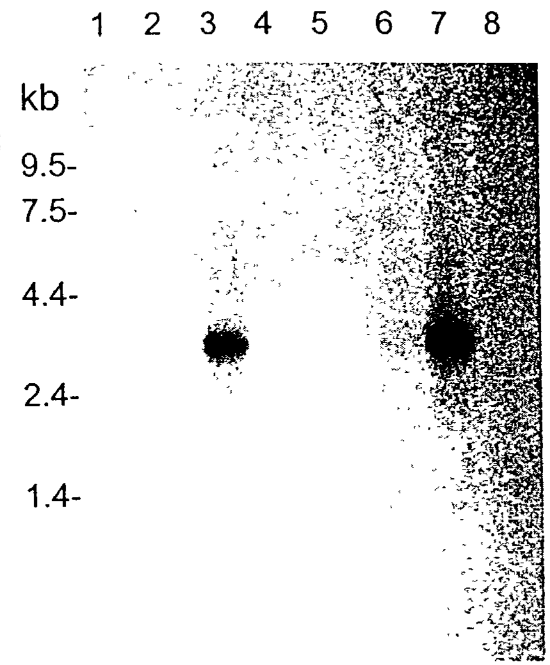
FIG. 3B. Northern blot analysis of 24P4C12 expression across a panel of normal human tissues, showing expression of an approximately 3 kb transcript in prostate and colon. Lanes represent the following tissues: (1) spleen; (2) thymus; (3) prostate; (4) testis; (5) ovary; (6) small intestine; (7) colon; and (8) leukocytes.
Figure 3C:
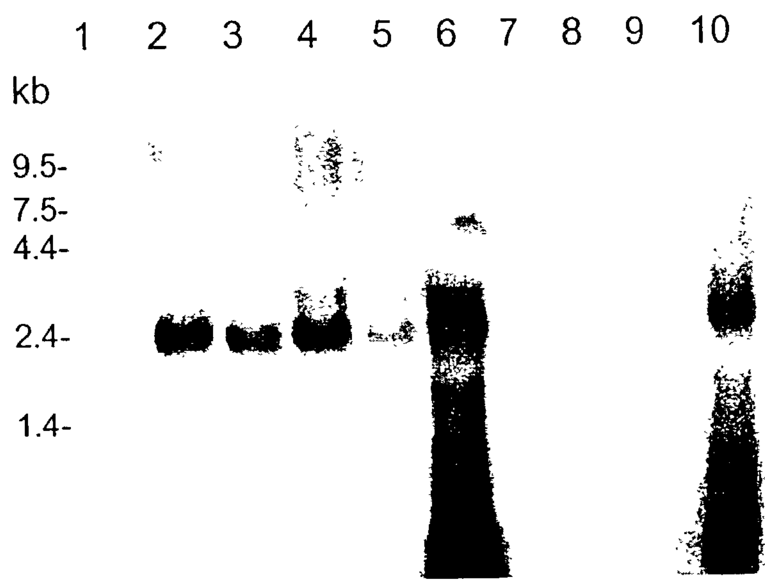
FIG. 3C. Northern blot analysis of 24P4C12 expression in prostate cancer xenografts and prostate cancer cell lines. Lanes represent the following tissues: (1) PrEC; (2) LAPC-4 AD; (3) LAPC-4 AI; (4) LAPC-9 AD; (5) LAPC-9 AI; (6) LNCaP; (7) PC-3; (8) DU145; (9) TsuPr1; and (10) LAPC-4 CL.
Figure 5:
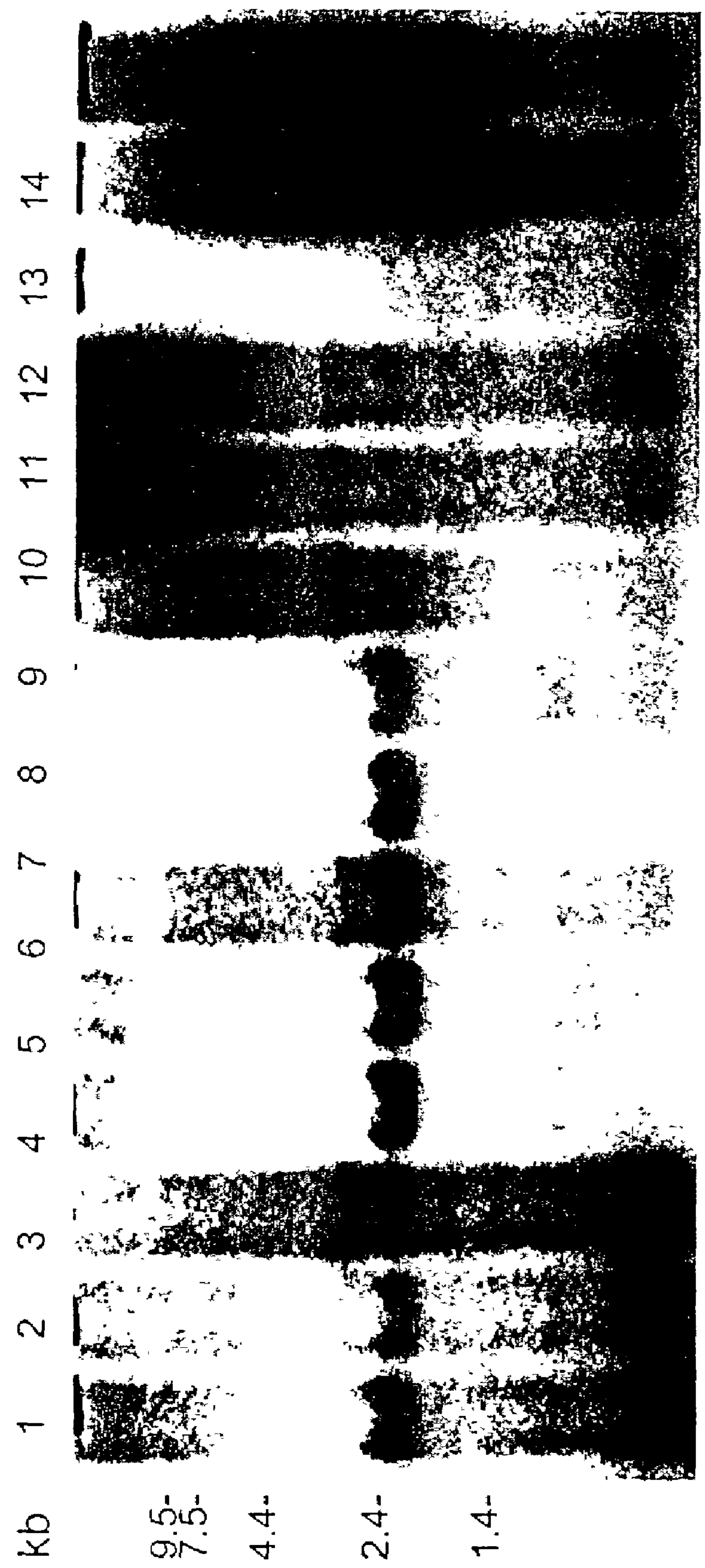
FIG. 5. Expression of 24P4C12 in LAPC xenografts. RNA was extracted from the LAPC xenograft that were grown subcutaneously (sc) or intra-tibially (it) within the mouse bone. Northern blots with 10 μg of total RNA/lane were probed with the 24P4C12 SSH fragment. Size standards in kilobases (kb) are indicated on the side. Lanes represent the following tissues: (1) LAPC-4 AD sc; (2) LAPC-4 AD sc; (3) LAPC-4 AD sc; (4) LAPC-4 AD it; (5) LAPC-4 AD it; (6) LAPC-4 AD it; (7) LAPC-4 AD $^{2}$; (8) LAPC-9 AD sc; (9) LAPC-9 AD sc; (10) LAPC-9 AD it; (11) LAPC-9 AD it; (12) LAPC-9 AD it; (13) LAPC-3 AI sc; and (14) LAPC-3 AI sc.
Figures 6A, 6B:
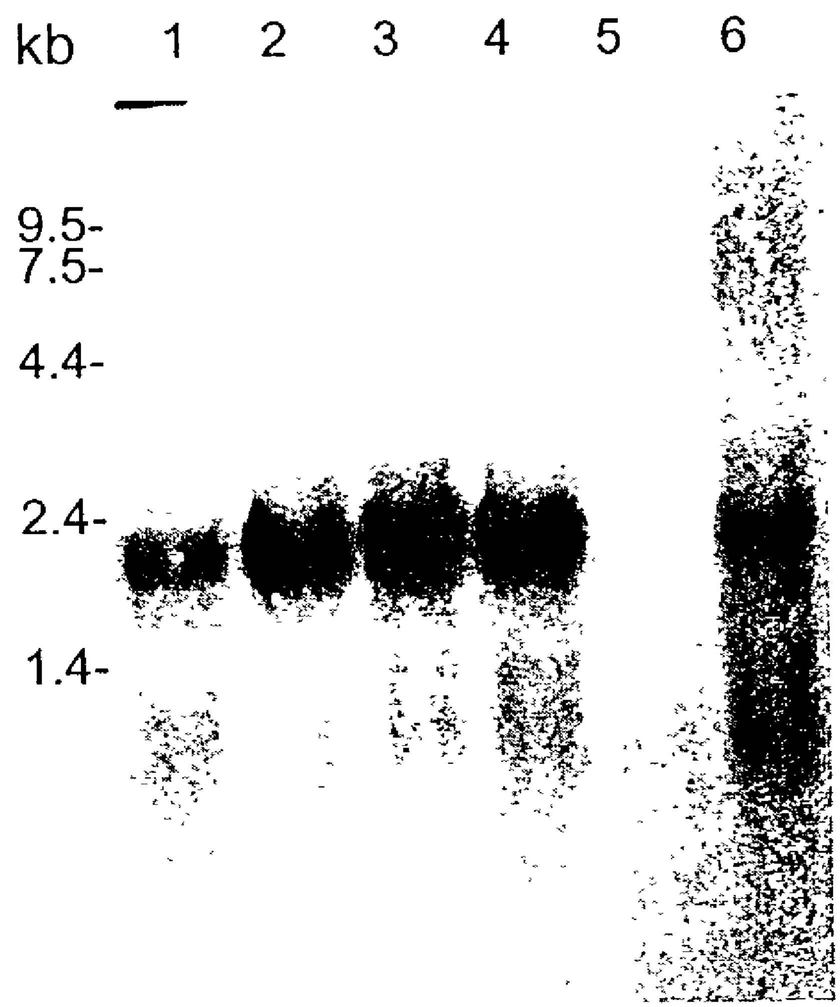
FIG. 6A. Expression of 24P4C12 in prostate cancer patient samples. RNA was extracted from the prostate tumors and their normal adjacent tissue derived from prostate cancer patients. Northern blots with 10 μg of total RNA/lane were probed with the 24P4C12 SSH fragment. Size standards in kilobases (kb) are indicated on the side. Lanes represent the following tissues: (1) Patient 1, normal adjacent tissue; (2) Patient 1, Gleason 7 tumor; (3) Patient 2, normal adjacent tumor; (4) Patient 2, Gleason 9 tumor; (5) Patient 3, normal adjacent tissue; (6) Patient 3, Gleason 7 tumor.
FIG. 6B. Expression of 24P4C12 in prostate cancer patient samples as described for FIG. 6A was compared to β-actin. Lanes represent the following tissues: (1) Patient 1, normal adjacent tissue; (2) Patient 1, Gleason 7 tumor; (3) Patient 2, normal adjacent tumor; (4) Patient 2, Gleason 9 tumor; (5) Patient 3, normal adjacent tissue; (6) Patient 3, Gleason 7 tumor.

Northern blot analysis using an 24P4C12 SSH fragment probe performed on 16 normal tissues showed expression primarily in prostate and colon, with lower expression detected in kidney, and significantly lower expression detected in pancreas, lung and placenta (FIGS. 2A-2C, 3A-3B). To analyze 24P4C12 expression in cancer tissues northern blotting was performed on RNA derived from the LAPC xenografts, and several prostate and non-prostate cancer cell lines. The results show high expression levels of 24P4C12 in LAPC-4 AD, LAPC-4 AI, LAPC-9 AD, LNCaP and LAPC-4 cell line (FIGS. 2A, 3C, 5). Very high levels are detected in LAPC-3 AI (FIG. 5). Lower levels are detected in LAPC-9 AI (FIG. 3C). More detailed analysis of the xenografts shows that 24P4C12 is highly expressed in the xenografts even when grown within the tibia of mice (FIG. 5). Northern analysis also shows that 24P4C12 is expressed in the normal prostate and prostate tumor tissues derived from prostate cancer patients (FIG. 6A). These results suggest that 24P4C12 is a prostate gene that is highly expressed in prostate cancer and may have a utility as a drug or antibody target in prostate cancer.

Structure and Expression of H38087

H38087 was identified as a family member of 24P4C12 by searching the dBEST database with the 24P4C12 amino acid sequence using the tblastn tool in NCBI. ESTs that encode protein fragments of homologous proteins were identified. One of these, H38087, was cloned from a testis library. The cDNA (clone GTB6) is 2738 bp in size (SEQ ID NO: 6) and encodes a 704 amino acid protein (SEQ ID NO: 7) with 11 putative transmembrane domains (underlined in FIGS. 7A-7D, and numbered therein as 152-220, 311-379, 743-811, 830-895, 995-1060, 1133-1201, 1394-1459, 1556-1624, 1655-1723, 1859-1924, and 19880-2056). The 58 base pairs of 5' untranslated region are very GC rich (87%), indicating that this gene may contain translational regulatory elements. The amino acid sequences of 24P4C12 and H38087 are 44% identical and 56% homologous over the entire sequence (FIG. 8).

Expression analysis shows that H38087 is ubiquitously expressed (FIG. 9), with highest expression levels detected in testis. Expression is also seen in all the LAPC xenografts. Because H38087 is ubiquitously expressed, it could serve as a control for testing 24P4C12-specific therapeutics. A 24P4C12-specific therapeutic that affects H38087 function could be toxic to normal cells. However, a therapeutic that selectively affects 24P4C12, but not H38087, may be less toxic to normal cells. Therefore, H38087 protein is useful as a pre-clinical testing tool for therapeutic modalities directed towards 24P4C12.

Polynucleotides

One aspect of the invention provides polynucleotides corresponding or complementary to all or part of a 24P4C12 gene, mRNA, and/or coding sequence, preferably in isolated form, including polynucleotides encoding a 24P4C12 protein and fragments thereof, DNA, RNA, DNA/RNA hybrid, and related molecules, polynucleotides or oligonucleotides complementary to a 24P4C12 gene or mRNA sequence or a part thereof, and polynucleotides or oligonucleotides that hybridize to a 24P4C12 gene, mRNA, or to a 24P4C12 encoding polynucleotide (collectively, "24P4C12 polynucleotides"). As used herein, the 24P4C12 gene and protein is meant to include the 24P4C12 genes and proteins specifically described herein and the genes and proteins corresponding to other 24P4C12 proteins and structurally similar variants of the foregoing. Such other 24P4C12 proteins and variants will generally have coding sequences that are highly homologous to the 24P4C12 coding sequence, and preferably will share at least about 50% amino acid identity and at least about 60% amino acid homology (using BLAST criteria), more preferably sharing 70% or greater homology (using BLAST criteria).

One embodiment of a 24P4C12 polynucleotide is a 24P4C12 polynucleotide having the sequence shown in FIGS. 1A-1D (SEQ ID NO: 1). A 24P4C12 polynucleotide may comprise a polynucleotide having the nucleotide sequence of human 24P4C12 as shown in FIGS. 1A-1D (SEQ ID NO: 1), wherein T can also be U; a polynucleotide that encodes all or part of the 24P4C12 protein; a sequence complementary to the foregoing; or a polynucleotide fragment of any of the foregoing. Another embodiment comprises a polynucleotide having the sequence as shown in FIGS. 1A-1D (SEQ ID NO: 1), from nucleotide residue number 6 through nucleotide residue number 2138, or having the sequence as shown in FIG. 1E (SEQ ID NO: 3), wherein T can also be U. Another embodiment comprises a polynucleotide encoding a 24P4C12 polypeptide whose sequence is encoded by the cDNA contained in either of the plasmids designated p24P4C12-GTE5 or p24P4C12-GTE9 deposited with American Type Culture Collection as Designation Nos. 207129 and 207084, respectively. Another embodiment comprises a polynucleotide that is capable of hybridizing under stringent hybridization conditions to the human 24P4C12 cDNA shown in FIGS. 1A-1D (SEQ ID NO: 1) or to a polynucleotide fragment thereof.

Typical embodiments of the invention disclosed herein include 24P4C12 polynucleotides encoding specific portions of the 24P4C12 mRNA sequence such as those that encode the protein and fragments thereof. For example, representative embodiments of the invention disclosed herein include: polynucleotides encoding about amino acid 1 to about amino acid 10 of the 24P4C12 protein shown in FIGS. 1A-1D (SEQ ID NO: 2), polynucleotides encoding about amino acid 20 to about amino acid 30 of the 24P4C12 protein shown in FIGS. 1A-1D (SEQ ID NO: 2), polynucleotides encoding about amino acid 30 to about amino acid 40 of the 24P4C12 protein shown in FIGS. 1A-1D (SEQ ID NO: 2), polynucleotides encoding about amino acid 40 to about amino acid 50 of the 24P4C12 protein shown in FIGS. 1A-1D (SEQ ID NO: 2), polynucleotides encoding about amino acid 50 to about amino acid 60 of the 24P4C12 protein shown in FIGS. 1A-1D (SEQ ID NO: 2), polynucleotides encoding about amino acid 60 to about amino acid 70 of the 24P4C12 protein shown in FIGS. 1A-1D (SEQ ID NO: 2), polynucleotides encoding about amino acid 70 to about amino acid 80 of the 24P4C12 protein shown in FIGS. 1A-1D (SEQ ID NO: 2), polynucleotides encoding about amino acid 80 to about amino acid 90 of the 24P4C12 protein shown in FIGS. 1A-1D (SEQ ID NO: 2) and polynucleotides encoding about amino acid 90 to about amino acid 100 of the 24P4C12 protein shown in FIGS. 1A-1D (SEQ ID NO: 2), etc. Following this scheme, polynucleotides (of at least 10 amino acids) encoding portions of the amino acid sequence of amino acids 100-710 of the 24P4C12 protein are typical embodiments of the invention. Polynucleotides encoding larger portions of the 24P4C12 protein are also contemplated. For example polynucleotides encoding from about amino acid 1 (or 20 or 30 or 40 etc.) to about amino acid 20, (or 30, or 40 or 50 etc.) of the 24P4C12 protein shown in FIGS. 1A-1D (SEQ ID NO: 2) may be generated by a variety of techniques well known in the art.

Additional illustrative embodiments of the invention disclosed herein include 24P4C12 polynucleotide fragments encoding one or more of the biological motifs contained within the 24P4C12 protein sequence. In one embodiment, typical polynucleotide fragments of the invention can encode one or more of the transmembrane domains disclosed herein. In another embodiment, typical polynucleotide fragments of the invention can encode one or more of the regions of 24P4C12 that exhibit homology to H38087, NG22 or CEESB82F. In another embodiment of the invention, typical polynucleotide fragments can encode one or more of the 24P4C12 N-glycosylation, protein kinase C phosphorylation, casein kinase II phosphorylation, tyrosine kinase phosphorylation, N-myristoylation, or amidation sites, or the leucine zipper pattern, as disclosed in greater detail in the text discussing the 24P4C12 protein and polypeptides below. In yet another embodiment of the invention, typical polynucleotide fragments can encode sequences that are unique to one or more 24P4C12 alternative splicing variants.

The polynucleotides of the preceding paragraphs have a number of different specific uses. For example, as 24P4C12 is shown to be specifically expressed in prostate cancers (FIGS. 2A, 3C, 5, 6), these polynucleotides may be used in methods for assessing the status of 24P4C12 gene products in normal versus cancerous tissues. Typically, polynucleotides encoding specific regions of the 24P4C12 protein may be used to assess the presence of perturbations (such as deletions, insertions, point mutations etc.) in specific regions (such regions containing a transmembrane domain) of the 24P4C12 gene products. Exemplary assays include both RT-PCR assays as well as single-strand conformation polymorphism (SSCP) analysis (see e.g. Marrogi et al., J. Cutan. Pathol. 26(8): 369-378 (1999), both of which utilize polynucleotides encoding specific regions of a protein to examine these regions within the protein.

Likewise, the invention additionally provides polynucleotides corresponding or complementary to all or part of a H38087 gene, mRNA, and/or coding sequence, preferably in isolated form, including polynucleotides encoding a H38087 protein and fragments thereof, DNA, RNA, DNA/RNA hybrid, and related molecules, polynucleotides or oligonucleotides complementary to a H38087 gene or mRNA sequence or a part thereof, and polynucleotides or oligonucleotides that hybridize to a H38087 gene, mRNA, or to a H38087 encoding polynucleotide (collectively, "H38087 polynucleotides"). As used herein, the H38087 gene and protein is meant to include the H38087 genes and proteins specifically described herein and the genes and proteins corresponding to other H38087 proteins and structurally similar variants of the foregoing. Such other H38087 proteins and variants will generally have coding sequences that are highly homologous to the H38087 coding sequence, and preferably will share at least about 50% amino acid identity and at least about 60% amino acid homology (using BLAST criteria), more preferably sharing 70% or greater homology (using BLAST criteria).

One embodiment of a H38087 polynucleotide is a H38087 polynucleotide having the sequence shown in FIGS. 7A-7D (SEQ ID NO: 6). A H38087 polynucleotide may comprise a polynucleotide having the nucleotide sequence of human H38087 as shown in FIGS. 7A-7D (SEQ ID NO: 6), wherein T can also be U; a polynucleotide that encodes all or part of the H38087 protein; a sequence complementary to the foregoing; or a polynucleotide fragment of any of the foregoing. Another embodiment comprises a polynucleotide having the sequence as shown in FIGS. 7A-7D (SEQ ID NO: 6), from nucleotide residue number 59 through nucleotide residue number 2173 (using the numbering shown in FIGS. 7A-7D; SEQ ID NO: 6). Another embodiment comprises a polynucleotide that is capable of hybridizing under stringent hybridization conditions to the human H38087 cDNA shown in FIGS. 7A-7D or to a polynucleotide fragment thereof.

Typical embodiments of the invention disclosed herein include H38087 polynucleotides encoding specific portions of the H38087 mRNA sequence such as those that encode the protein and fragments thereof. For example, representative embodiments of the invention disclosed herein include: polynucleotides encoding about amino acid 1 to about amino acid 10 of the H38087 protein shown in FIGS. 7A-7D (SEQ ID NO: 7), polynucleotides encoding about amino acid 20 to about amino acid 30 of the H38087 protein shown in FIGS. 7A-7D (SEQ ID NO: 7), polynucleotides encoding about amino acid 30 to about amino acid 40 of the H38087 protein shown in FIGS. 7A-7D (SEQ ID NO: 7), polynucleotides encoding about amino acid 40 to about amino acid 50 of the H38087 protein shown in FIGS. 7A-7D (SEQ ID NO: 7), polynucleotides encoding about amino acid 50 to about amino acid 60 of the H38087 protein shown in FIGS. 7A-7D (SEQ ID NO: 7), polynucleotides encoding about amino acid 60 to about amino acid 70 of the H38087 protein shown in FIGS. 7A-7D (SEQ ID NO: 7), polynucleotides encoding about amino acid 70 to about amino acid 80 of the H38087 protein shown in FIGS. 7A-7D (SEQ ID NO: 7), polynucleotides encoding about amino acid 80 to about amino acid 90 of the H38087 protein shown in FIGS. 7A-7D (SEQ ID NO: 7) and polynucleotides encoding about amino acid 90 to about amino acid 100 of the H38087 protein shown in FIGS. 7A-7D (SEQ ID NO: 7), etc. Following this scheme, polynucleotides (of at least 10 amino acids) encoding portions of the amino acid sequence of amino acids 100-704 of the H38087 protein are typical embodiments of the invention. Polynucleotides encoding larger portions of the H38087 protein are also contemplated. For example polynucleotides encoding from about amino acid 1 (or 20 or 30 or 40 etc.) to about amino acid 20, (or 30, or 40 or 50 etc.) of the H38087 protein shown in FIGS. 7A-7D (SEQ ID NO: 7) may be generated by a variety of techniques well known in the art.

Additional illustrative embodiments of the invention disclosed herein include H38087 polynucleotide fragments encoding one or more of the biological motifs contained within the H38087 protein sequence. In one embodiment, typical polynucleotide fragments of the invention can encode one or more of the transmembrane domains disclosed herein. In another embodiment, typical polynucleotide fragments of the invention can encode one or more of the regions of H38087 that exhibit homology to 24P4C12, NG22 or CEESB82F. In another embodiment of the invention, typical polynucleotide fragments can encode one or more of the H38087 N-glycosylation, protein kinase C phosphorylation, casein kinase II phosphorylation, tyrosine kinase phosphorylation, or N-myristoylation sites, or the signal sequence, as disclosed in greater detail in the text discussing the H38087 protein and polypeptides below. In yet another embodiment of the invention, typical polynucleotide fragments can encode sequences that are unique to one or more H38087 alternative splicing variants.

Other specifically contemplated embodiments of the invention disclosed herein are genomic DNA, cDNAs, ribozymes, and antisense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the 24P4C12 and H38087 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 24P4C12 or H38087. See for example, Jack Cohen, OLIGODEOXYNUCLEOTIDES, Antisense Inhibitors of Gene Expression, CRC Press, 1989; and Synthesis 1:1-5 (1988). The 24P4C12 and H38087 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1,1-dioxide, which is a sulfur transfer reagent. See Iyer, R. P. et al, J. Org. Chem. 55:4693-4698 (1990); and Iyer, R. P. et al., J. Am. Chem. Soc. 112:1253-1254 (1990), the disclosures of which are fully incorporated by reference herein.

The 24P4C12 and H38087 antisense oligonucleotides of the present invention typically may be RNA or DNA that is complementary to and stably hybridizes with the first 100 N-terminal codons or last 100 C-terminal codons of the 24P4C12 or H38087 genome or the corresponding mRNA. While absolute complementarity is not required, high degrees of complementarity are preferred. Use of an oligonucleotide complementary to this region allows for the selective hybridization to 24P4C12 or H38087 mRNA and not to mRNA specifying other regulatory subunits of protein kinase. Preferably, the 24P4C12 and H38087 antisense oligonucleotides of the present invention are a 15 to 30-mer fragment of the antisense DNA molecule having a sequence that hybridizes to 24P4C12 or H38087 mRNA. Optionally, the 24P4C12 or H38087 antisense oligonucleotide is a 30-mer oligonucleotide that is complementary to a region in the first 10 N-terminal codons and last 10 C-terminal codons of 24P4C12 or H38087. Alternatively, the antisense molecules are modified to employ ribozymes in the inhibition of 24P4C12 or H38087 expression. L. A. Couture & D. T. Stinchcomb; *Trends Genet* 12: 510-515 (1996).

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of a 24P4C12 or H38087 polynucleotide in a sample and as a means for detecting a cell expressing a 24P4C12 or H38087 protein.

Examples of such probes include polypeptides comprising all or part of the human 24P4C12 cDNA sequence shown in FIGS. 1A-1D (SEQ ID NO: 1) or the human H38087 cDNA sequence FIGS. 7A-7D (SEQ ID NO: 6). Examples of primer pairs capable of specifically amplifying 24P4C12 or H38087 mRNAs are also described in the Examples that follow. As will be understood by the skilled artisan, a great many different primers and probes may be prepared based on the sequences provided herein and used effectively to amplify and/or detect a 24P4C12 or H38087 mRNA.

As used herein, a polynucleotide is said to be "isolated" when it is substantially separated from contaminant polynucleotides that correspond or are complementary to genes other than the 24P4C12 or H38087 gene or that encode polypeptides other than 24P4C12 or H38087 gene product or fragments thereof. A skilled artisan can readily employ nucleic acid isolation procedures to obtain an isolated 24P4C12 or H38087 polynucleotide.

The 24P4C12 or H38087 polynucleotides of the invention are useful for a variety of purposes, including but not limited to their use as probes and primers for the amplification and/or detection of the 24P4C12 or H38087 genes, mRNAs, or fragments thereof; as reagents for the diagnosis and/or prognosis of prostate cancer and other cancers; as coding sequences capable of directing the expression of 24P4C12 or H38087 polypeptides; as tools for modulating or inhibiting the expression of the 24P4C12 or H38087 genes and/or translation of the 24P4C12 or H38087 transcripts; and as therapeutic agents.

Isolation of 24P4C12- and H38087-Encoding Nucleic Acid Molecules

The 24P4C12 and H38087 cDNA sequences described herein enable the isolation of other polynucleotides encoding 24P4C12 or H38087 gene product(s), as well as the isolation of polynucleotides encoding 24P4C12 or H38087 gene product homologs, alternatively spliced isoforms, allelic variants, and mutant forms of the 24P4C12 or H38087 gene product. Various molecular cloning methods that can be employed to isolate full length cDNAs encoding a 24P4C12 or H38087 gene are well known (See, for example, Sambrook, J. et al., Molecular Cloning: A Laboratory Manual, 2d edition., Cold Spring Harbor Press, New York, 1989; Current Protocols in Molecular Biology. Ausubel et al., Eds., Wiley and Sons, 1995). For example, lambda phage cloning methodologies may be conveniently employed, using commercially available cloning systems (e.g., Lambda ZAP Express, Stratagene). Phage clones containing 24P4C12 or H38087 gene cDNAs may be identified by probing with a labeled 24P4C12 or H38087 cDNA or a fragment thereof. For example, in one embodiment, the 24P4C12 cDNA (FIGS. 1A-1D; SEQ ID NO: 1) or a portion thereof can be synthesized and used as a probe to retrieve overlapping and full length cDNAs corresponding to a 24P4C12 gene. The 24P4C12 gene itself may be isolated by screening genomic DNA libraries, bacterial artificial chromosome libraries (BACs), yeast artificial chromosome libraries (YACs), and the like, with 24P4C12 DNA probes or primers.

Recombinant DNA Molecules and Host-Vector Systems

The invention also provides recombinant DNA or RNA molecules containing a 24P4C12 or H38087 polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, for example, Sambrook et al, 1989, supra).

The invention further provides a host-vector system comprising a recombinant DNA molecule containing a 24P4C12 and/or H38087 polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such LnCaP, PC-3, DU145, LAPC-4, TsuPr1, other transfectable or transducible prostate cancer cell lines, as well as a number of mammalian cells routinely used for the expression of recombinant proteins (e.g., COS, CHO, 293, 293T cells). More particularly, a polynucleotide comprising the coding sequence of 24P4C12 or H38087 may be used to generate 24P4C12 or H38087 proteins or fragments thereof using any number of host-vector systems routinely used and widely known in the art.

A wide range of host-vector systems suitable for the expression of 24P4C12 and H38087 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, 24P4C12 or H38087 may be preferably expressed in several prostate cancer and non-prostate cell lines, including for example 293, 293T, rat-1, NIH 3T3, PC-3, LNCaP and TsuPr1. The host-vector systems of the invention are useful for the production of a 24P4C12 or H38087 protein or fragment thereof. Such host-vector systems may be employed to study the functional properties of 24P4C12 or H38087 and 24P4C12 or H38087 mutations.

Recombinant human 24P4C12 or H38087 protein may be produced by mammalian cells transfected with a construct encoding 24P4C12 or H38087. In an illustrative embodiment described in the Examples, 293T cells can be transfected with an expression plasmid encoding 24P4C12, the 24P4C12 protein is expressed in the 293T cells, and the recombinant 24P4C12 protein can be isolated using standard purification methods (e.g., affinity purification using anti-24P4C12 antibodies). In another embodiment, also described in the Examples herein, the 24P4C12 coding sequence is subcloned into the retroviral vector pSRαtkneo and used to infect various mammalian cell lines, such as NIH 3T3, PC3 and LnCaP in order to establish 24P4C12 expressing cell lines. Various other expression systems well known in the art may also be employed. Expression constructs encoding a leader peptide joined in frame to the 24P4C12 coding sequence may be used for the generation of a secreted form of recombinant 24P4C12 protein.

Proteins encoded by the 24P4C12 or H38087 genes, or by fragments thereof, will have a variety of uses, including but not limited to generating antibodies and in methods for identifying ligands and other agents and cellular constituents that bind to a 24P4C12 or H38087 gene product. Antibodies raised against a 24P4C12 or H38087 protein or fragment thereof may be useful in diagnostic and prognostic assays, and imaging methodologies in the management of human cancers characterized by expression of 24P4C12 protein, including but not limited to cancer of the prostate. Such antibodies may be expressed intracellularly and used in methods of treating patients with such cancers. Various immunological assays useful for the detection of 24P4C12 and H38087 proteins are contemplated, including but not limited to various types of radioimmunoassays, enzyme-linked immunosorbent assays (ELISA), enzyme-linked immunofluorescent assays (ELIFA), immunocytochemical methods, and the like. Such antibodies may be labeled and used as immunological imaging reagents capable of detecting 24P4C12 or H38087 expressing cells (e.g., in radioscintigraphic imaging methods). 24P4C12 proteins may also be particularly useful in generating cancer vaccines, as further described below.

24P4C12 Polypeptides

Another aspect of the present invention provides 24P4C12 proteins and polypeptide fragments thereof. The 24P4C12 proteins of the invention include those specifically identified herein, as well as allelic variants, conservative substitution variants and homologs that can be isolated/generated and characterized without undue experimentation following the methods outlined below. Fusion proteins that combine parts of different 24P4C12 proteins or fragments thereof, as well as fusion proteins of a 24P4C12 protein and a heterologous polypeptide are also included. Such 24P4C12 proteins will be collectively referred to as the 24P4C12 proteins, the proteins of the invention, or 24P4C12. As used herein, the term "24P4C12 polypeptide" refers to a polypeptide fragment or a 24P4C12 protein of at least 10 amino acids, preferably at least 15 amino acids.

Specific embodiments of 24P4C12 proteins comprise a polypeptide having the amino acid sequence of human 24P4C12 as shown in FIGS. 1A-1D (SEQ ID NO: 2). Alternatively, embodiments of 24P4C12 proteins comprise variant polypeptides having alterations in the amino acid sequence of human 24P4C12 as shown in FIGS. 1A-1D (SEQ ID NO: 2).

In general, naturally occurring allelic variants of human 24P4C12 will share a high degree of structural identity and homology (e.g., 90% or more identity). Typically, allelic variants of the 24P4C12 proteins will contain conservative amino acid substitutions within the 24P4C12 sequences described herein or will contain a substitution of an amino acid from a corresponding position in a 24P4C12 homologue. One class of 24P4C12 allelic variants will be proteins that share a high degree of homology with at least a small region of a particular 24P4C12 amino acid sequence, but will further contain a radical departure form the sequence, such as a non-conservative substitution, truncation, insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Embodiments of the invention disclosed herein include a wide variety of art accepted variants of 24P4C12 proteins such as polypeptides having amino acid insertions, deletions and substitutions. 24P4C12 variants can be made using methods known in the art such as site-directed mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., Gene, 34:315 (1985)], restriction selection mutagenesis [Wells et al., *Philos. Trans. R. Soc. London SerA,* 317:415 (1986)] or other known techniques can be performed on the cloned DNA to produce the 24P4C12 variant DNA. Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W. H. Freeman & Co., N.Y.); Chothia, J. Mol. Biol., 150:1 (1976)]. If alanine substitution does not yield adequate amounts of variant, an isosteric amino acid can be used.

As discussed above, embodiments of the claimed invention include polypeptides containing less than the 710 amino acid sequence of the 24P4C12 protein shown in FIGS. 1A-1D (SEQ ID NO: 2). For example, representative embodiments of the invention disclosed herein include polypeptides consisting of about amino acid 1 to about amino acid 10 of the 24P4C12 protein shown in FIGS. 1A-1D (SEQ ID NO: 2), polypeptides consisting of about amino acid 20 to about amino acid 30 of the 24P4C12 protein shown in FIGS. 1A-1D (SEQ ID NO: 2), polypeptides consisting of about amino acid 30 to about amino acid 40 of the 24P4C12 protein shown in FIGS. 1A-1D (SEQ ID NO: 2), polypeptides consisting of about amino acid 40 to about amino acid 50 of the 24P4C12 protein shown in FIGS. 1A-1D (SEQ ID NO: 2), polypeptides consisting of about amino acid 50 to about amino acid 60 of the 24P4C12 protein shown in FIGS. 1A-1D (SEQ ID NO: 2), polypeptides consisting of about amino acid 60 to about amino acid 70 of the 24P4C12 protein shown in FIGS. 1A-1D (SEQ ID NO: 2), polypeptides consisting of about amino acid 70 to about amino acid 80 of the 24P4C12 protein shown in FIGS. 1A-1D (SEQ ID NO: 2), polypeptides consisting of about amino acid 80 to about amino acid 90 of the 24P4C12 protein shown in FIGS. 1A-1D (SEQ ID NO: 2) and polypeptides consisting of about amino acid 90 to about amino acid 100 of the 24P4C12 protein shown in FIGS. 1A-1D (SEQ ID NO: 2), etc. Following this scheme, polypeptides consisting of portions of the amino acid sequence of amino acids 100-710 of the 24P4C12 protein are typical embodiments of the invention. Polypeptides consisting of larger portions of the 24P4C12 protein are also contemplated. For example polypeptides consisting of about amino acid 1 (or 20 or 30 or 40 etc.) to about amino acid 20, (or 30, or 40 or 50 etc.) of the 24P4C12 protein shown in FIGS. 1A-1D (SEQ ID NO: 2) may be generated by a variety of techniques well known in the art.

Additional illustrative embodiments of the invention disclosed herein include 24P4C12 polypeptides containing the amino acid residues of one or more of the biological motifs contained within the 24P4C12 polypeptide sequence as shown in FIG. 1A (SEQ ID NO: 2). In one embodiment, typical polypeptides of the invention can contain one or more of the transmembrane regions shown in FIGS. 1A-1D (SEQ ID NO: 2), or one or more of the regions of 24P4C12 that exhibit homology to H38087, NG22 OR CEESB82F. In another embodiment, typical polypeptides of the invention can contain one or more of the 24P4C12 N-glycosylation sites such as NRSC (SEQ ID NO: 8) at residues 29-32 (numbering from first amino acid residue shown in FIG. 1A), NSTG (SEQ ID NO: 9) at residues 69-72, NMTV (SEQ ID NO: 10) at residues 155-158, NDTT (SEQ ID NO: 11) at residues 197-200, NLSA (SEQ ID NO: 12) at residues 298-301, NISS (SEQ ID NO: 13) at residues 393-396, NTSC (SEQ ID NO: 14) at residues 405-408, NSSC (SEQ ID NO: 15) at residues 416-419, and/or NGSL (SEQ ID NO: 16) at residues 678-681. In another embodiment, typical polypeptides of the invention can contain one or more of the 24P4C12 protein kinase C phosphorylation sites such as SFR at residues 22-24, SVK at residues 218-220, SSK at residues 430-432, TLR at residues 494-496, SAK at residues 573-575, and/or SGR at residues 619-621. In another embodiment, typical polypeptides of the invention can contain one or more of the 24P4C12 casein kinase II phosphorylation sites such as SCTD (SEQ ID NO: 17) at residues 31-34, SVAE (SEQ ID NO: 18) at residues 102-105, SCPE (SEQ ID NO: 19) at residues 119-122, TVGE (SEQ ID NO: 20) at residues 135-138, and/or SVQE (SEQ ID NO: 21) at residues 304-307. In another embodiment, typical polypeptides of the invention can contain one or more of the tyrosine kinase phosphorylation sites such as RDEDDEAY (SEQ ID NO: 22) at residues 6-13. In another embodiment, typical polypeptides of the invention can contain one or more of the N-myristoylation sites such as GAYCGM (SEQ ID NO: 23) at residues 72-77, GMGENK (SEQ ID NO: 24) at residues 76-81, GVPWNM (SEQ ID NO: 25) at residues 151-156, GLIDSL (SEQ ID NO: 26) at residues 207-212, GIYYCW (SEQ ID NO: 27) at residues 272-277, GASISQ (SEQ ID NO: 28) at residues 287-292, GQMMST (SEQ ID NO: 29) at residues 379-354, GLFWTL (SEQ ID NO: 30) at residues 449-454, and/or GAFASF (SEQ ID NO: 31) at residues 467-472. In another embodiment, typical polypeptides of the invention can contain one or more of the amidation sites such as LGKK (SEQ ID NO: 32) at residues 695-698. In another embodiment, typical polypeptides of the invention can contain a leucine zipper pattern such as LFILLLR-LVAGPLVLVILGVL (SEQ ID NO: 33) at residues 245-266. Related embodiments of these inventions include polypeptides containing combinations of the different motifs discussed above with preferable embodiments being those which contain no insertions, deletions or substitutions either within the motifs or the intervening sequences of these polypeptides.

In yet another embodiment of the invention, typical polypeptides can contain amino acid sequences that are unique to one or more 24P4C12 alternative splicing variants. The monitoring of alternative splice variants of 24P4C12 is useful because changes in the alternative splicing of proteins is suggested as one of the steps in a series of events that lead to the progression of cancers (see e.g. Carstens et al., Oncogene 15(250: 3059-3065 (1997)). Consequently, monitoring of alternative splice variants of 24P4C12 provides an additional means to evaluate syndromes associated with perturbations in 24P4C12 gene products such as cancers.

Polypeptides consisting of one or more of the 24P4C12 motifs discussed above are useful in elucidating the specific characteristics of a malignant phenotype in view of the observation that the 24P4C12 motifs discussed above are associated with growth disregulation and because 24P4C12 is overexpressed in cancers (FIG. 5). Casein kinase II and cAMP and cCMP-dependent protein kinase, for example are enzymes known to be associated with the development of the malignant phenotype (see e.g. Chen et al., Lab Invest., 78(2): 165-174 (1998); Gaiddon et al., Endocrinology 136 (10): 4331-4338 (1995) and Hall et al., Nucleic Acids Research 24(6): 1119-1126 (1996)). Moreover, both glycosylation and myristoylation are protein modifications also associated with cancer and cancer progression (see e.g. Dennis et al., Biochim. Biophys. Acta 1473(1):21-34 (1999); Raju et al., Exp. Cell Res. 235(1): 145-154 (1997)).

The polypeptides of the preceding paragraphs have a number of different specific uses. As 24P4C12 is shown to be highly expressed in prostate cancers (FIGS. 2A, 3C, 5, 6), these polypeptides may be used in methods for assessing the status of 24P4C12 gene products in normal versus cancerous tissues and elucidating the malignant phenotype. Typically, polypeptides encoding specific regions of the 24P4C12 protein may be used to assess the presence of perturbations (such as deletions, insertions, point mutations etc.) in specific regions (such as regions containing a transmembrane domain) of the 24P4C12 gene products. Exemplary assays can utilize antibodies targeting a 24P4C12 polypeptides containing the amino acid residues of one or more of the biological motifs contained within the 24P4C12 polypeptide sequence in order to evaluate the characteristics of this region in normal versus cancerous tissues. Alternatively, 24P4C12 polypeptides containing the amino acid residues of one or more of the biological motifs contained within the 24P4C12 polypeptide sequence can be used to screen for factors that interact with that region of 24P4C12.

As discussed above, redundancy in the genetic code permits variation in 24P4C12 gene sequences. In particular, one skilled in the art will recognize specific codon preferences by a specific host species and can adapt the disclosed sequence as preferred for a desired host. For example, preferred codon sequences typically have rare codons (i.e., codons having a usage frequency of less than about 20% in known sequences of the desired host) replaced with higher frequency codons. Codon preferences for a specific organism may be calculated, for example, by utilizing codon usage tables available on the INTERNET at the following address: http://www.dna.affrc.go.jp/~nakamura/codon.html. Nucleotide sequences that have been optimized for a particular host species by replacing any codons having a usage frequency of less than about 20% are referred to herein as "codon optimized sequences."

Additional sequence modifications are known to enhance protein expression in a cellular host. These include elimination of sequences encoding spurious polyadenylation signals, exon/intron splice site signals, transposon-like repeats, and/or other such well-characterized sequences that may be deleterious to gene expression. The GC content of the sequence may be adjusted to levels average for a given cellular host, as calculated by reference to known genes expressed in the host cell. Where possible, the sequence may also be modified to avoid predicted hairpin secondary mRNA structures. Other useful modifications include the addition of a translational initiation consensus sequence at the start of the open reading frame, as described in Kozak, *Mol. Cell Biol.,* 9:5073-5080 (1989). Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequence."

24P4C12 proteins may be embodied in many forms, preferably in isolated form. As used herein, a protein is said to be "isolated" when physical, mechanical or chemical methods are employed to remove the 24P4C12 protein from cellular constituents that are normally associated with the protein. A skilled artisan can readily employ standard purification methods to obtain an isolated 24P4C12 protein. A purified 24P4C12 protein molecule will be substantially free of other proteins or molecules that impair the binding of 24P4C12 to antibody or other ligand. The nature and degree of isolation and purification will depend on the intended use. Embodiments of a 24P4C12 protein include a purified 24P4C12 protein and a functional, soluble 24P4C12 protein. In one form, such functional, soluble 24P4C12 proteins or fragments thereof retain the ability to bind antibody or other ligand.

The invention also provides 24P4C12 polypeptides comprising biologically active fragments of the 24P4C12 amino acid sequence, such as a polypeptide corresponding to part of the amino acid sequence for 24P4C12 as shown in FIGS. 1A-1D (SEQ ID NO: 2). Such polypeptides of the invention exhibit properties of the 24P4C12 protein, such as the ability to elicit the generation of antibodies that specifically bind an epitope associated with the 24P4C12 protein.

24P4C12 polypeptides can be generated using standard peptide synthesis technology or using chemical cleavage methods well known in the art based on the amino acid sequences of the human 24P4C12 proteins disclosed herein. Alternatively, recombinant methods can be used to generate nucleic acid molecules that encode a polypeptide fragment of a 24P4C12 protein. In this regard, the 24P4C12-encoding nucleic acid molecules described herein provide means for generating defined fragments of 24P4C12 proteins. 24P4C12 polypeptides are particularly useful in generating and characterizing domain specific antibodies (e.g., antibodies recognizing an extracellular or intracellular epitope of a 24P4C12 protein), in identifying agents or cellular factors that bind to 24P4C12 or a particular structural domain thereof, and in various therapeutic contexts, including but not limited to cancer vaccines.

24P4C12 polypeptides containing particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments containing such structures are particularly useful in generating subunit specific anti-24P4C12 antibodies or in identifying cellular factors that bind to 24P4C12.

In an embodiment described in the examples that follow, 24P4C12 can be conveniently expressed in cells (such as 293T cells) transfected with a commercially available expression vector such as a CMV-driven expression vector encoding 24P4C12 with a C-terminal 6×His and MYC tag (pcDNA3.1/mycHIS, Invitrogen). The HIS-tagged 24P4C12 expressed in cells may be purified using a nickel column using standard techniques.

Modifications of 24P4C12 such as covalent modifications are included within the scope of this invention. One type of covalent modification includes reacting targeted amino acid residues of a 24P4C12 polypeptide with an organic derivatizing agent that is capable of reacting with selected side chains or the N- or C-terminal residues of the 24P4C12. Another type of covalent modification of the 24P4C12 polypeptide included within the scope of this invention comprises altering the native glycosylation pattern of the polypeptide. "Altering the native glycosylation pattern" is intended for purposes herein to mean deleting one or more carbohydrate moieties found in native sequence 24P4C12 (either by removing the underlying glycosylation site or by deleting the glycosylation by chemical and/or enzymatic means), and/or adding one or more glycosylation sites that are not present in the native sequence 24P4C12. In addition, the phrase includes qualitative changes in the glycosylation of the native proteins, involving a change in the nature and proportions of the various carbohydrate moieties present. Another type of covalent modification of 24P4C12 comprises linking the 24P4C12 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The 24P4C12 of the present invention may also be modified in a way to form a chimeric molecule comprising 24P4C12 fused to another, heterologous polypeptide or amino acid sequence. In one embodiment, such a chimeric molecule comprises a fusion of the 24P4C12 with a polyhistidine epitope tag, which provides an epitope to which immobilized nickel can selectively bind. The epitope tag is generally placed at the amino- or carboxyl-terminus of the 24P4C12. In an alternative embodiment, the chimeric molecule may comprise a fusion of the 24P4C12 with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 24P4C12 polypeptide in place of at least one variable region within an Ig molecule. In a particularly preferred embodiment, the immunoglobulin fusion includes the hinge, CH2 and CH3, or the hinge, CHI, CH2 and CH3 regions of an IgGI molecule. For the production of immunoglobulin fusions see also U.S. Pat. No. 5,428,130 issued Jun. 27, 1995.

H38087 Polypeptides

Another aspect of the present invention provides H38087 proteins and polypeptide fragments thereof. The H38087 proteins of the invention include those specifically identified herein, as well as allelic variants, conservative substitution variants and homologs that can be isolated/generated and characterized without undue experimentation following the methods outlined herein. Fusion proteins that combine parts of different H38087 proteins or fragments thereof, as well as fusion proteins of a H38087 protein and a heterologous polypeptide are also included. Such H38087 proteins will be collectively referred to as the H38087 proteins or H38087. As used herein, the term "H38087 polypeptide" refers to a polypeptide fragment or a H38087 protein of at least 10 amino acids, preferably at least 15 amino acids.

As discussed above, embodiments of the claimed invention include polypeptides containing less than the 704 amino acid sequence of the H38087 protein shown in FIGS. 7A-7D (SEQ ID NO: 7). For example, representative embodiments of the invention disclosed herein include polypeptides consisting of about amino acid 1 to about amino acid 10 of the H38087 protein shown in FIGS. 7A-7D (SEQ ID NO: 7), polypeptides consisting of about amino acid 20 to about amino acid 30 of the H38087 protein shown in FIGS. 7A-7D (SEQ ID NO: 7), polypeptides consisting of about amino acid 30 to about amino acid 40 of the H38087 protein shown in FIGS. 7A-7D (SEQ ID NO: 7), polypeptides consisting of about amino acid 40 to about amino acid 50 of the H38087 protein shown in FIGS. 7A-7D (SEQ ID NO: 7), polypeptides consisting of about amino acid 50 to about amino acid 60 of the H38087 protein shown in FIGS. 7A-7D (SEQ ID NO: 7), polypeptides consisting of about amino acid 60 to about amino acid 70 of the H38087 protein shown in FIGS. 7A-7D (SEQ ID NO: 7), polypeptides consisting of about amino acid 70 to about amino acid 80 of the H38087 protein shown in FIGS. 7A-7D (SEQ ID NO: 7), polypeptides consisting of about amino acid 80 to about amino acid 90 of the H38087 protein shown in FIGS. 7A-7D (SEQ ID NO: 7) and polypeptides consisting of about amino acid 90 to about amino acid 100 of the H38087 protein shown in FIGS. 7A-7D (SEQ ID NO: 7), etc. Following this scheme, polypeptides consisting of portions of the amino acid sequence of amino acids 100-710 of the H38087 protein are typical embodiments of the invention. Polypeptides consisting of larger portions of the H38087 protein are also contemplated. For example polypeptides consisting of about amino acid 1 (or 20 or 30 or 40 etc.) to about amino acid 20, (or 30, or 40 or 50 etc.) of the H38087 protein shown in FIGS. 7A-7D (SEQ ID NO: 7) may be generated by a variety of techniques well known in the art.

Additional illustrative embodiments of the invention disclosed herein include H38087 polypeptides containing the amino acid residues of one or more of the biological motifs contained within the H38087 polypeptide sequence as shown in FIG. 7 (SEQ ID NO: 7). In one embodiment, typical polypeptides of the invention can contain one or more of the transmembrane regions shown in FIGS. 7A-7D, or one or more of the regions of H38087 that exhibit homology to 24P4C12, NG22 OR CEESB82F. In another embodiment, typical polypeptides of the invention can contain one or more of the H38087 N-glycosylation sites such as NETT (SEQ ID NO: 46) at residues 185-188 (numbering from first amino acid residue shown in FIG. 7), NITD (SEQ ID NO: 47) at residues 198-201, and/or NKTN (SEQ ID NO: 48) at residues 695-698. In another embodiment, typical polypeptides of the invention can contain one or more of the H38087 protein kinase C phosphorylation sites such as TFK at residues 19-21, SSR at residues 126-128, SRK at residues 195-197, TAK at residues 402-404, SAR at residues 574-576, THR at residues 620-622, TLK at residues 689-

691, and/or TNK at residues 697-699. In another embodiment, typical polypeptides of the invention can contain one or more of the H38087 casein kinase II phosphorylation sites such as THGD (SEQ ID NO: 49) at residues 54-57, SRGE (SEQ ID NO: 50) at residues 67-70, TKNE (SEQ ID NO: 51) at residues 77-80, SSRD (SEQ ID NO: 52) at residues 126-129, TTYE (SEQ ID NO: 53) at residues 187-190, TYED (SEQ ID NO: 54) at residues 188-191, SLVD (SEQ ID NO: 55) at residues 293-296, SILE (SEQ ID NO: 56) at residues 321-234, TSNE (SEQ ID NO: 57) at residues 385-388 and/or SSHE (SEQ ID NO: 58) at residues 413-416. In another embodiment, typical polypeptides of the invention can contain one or more of the tyrosine kinase phosphorylation sites such as RSSRDFEYY (SEQ ID NO: 59) at residues 125-133. In another embodiment, typical polypeptides of the invention can contain one or more of the N-myristoylation sites such as GQKGTK (SEQ ID NO: 60) at residues 73-78, GNETTY (SEQ ID NO: 61) at residues 184-189, GSRKNI (SEQ ID NO: 62) at residues 194-199, GAKKAN (SEQ ID NO: 63) at residues 205-210, GVLEAR (SEQ ID NO: 64) at residues 211-216, GLVIAM (SEQ ID NO: 65) at residues 236-241, GIFHCY (SEQ ID NO: 66) at residues 273-278, GSDVSL (SEQ ID NO: 67) at residues 289-294, GGESGY (SEQ ID NO: 68) at residues 431-436, GAFASY (SEQ ID NO: 69) at residues 468-473, and/or GTNFCT (SEQ ID NO: 70) at residues 568-573. Related embodiments of these inventions include polypeptides containing combinations of the different motifs discussed above with preferable embodiments being those which contain no insertions, deletions or substitutions either within the motifs or the intervening sequences of these polypeptides.

The H38087 polypeptides of the invention can be modified, generated and used in manners analogous to those described above for 24P4C12 polypeptides, as would be known and appreciated by those skilled in the art.

24P4C12 Antibodies

The term "antibody" is used in the broadest sense and specifically covers single anti-24P4C12 monoclonal antibodies (including agonist, antagonist and neutralizing antibodies) and anti-24P4C12 antibody compositions with polyepitopic specificity. The term "monoclonal antibody" (mAb) as used herein refers to an antibody obtained from a population of substantially homogeneous antibodies, i.e. the antibodies comprising the individual population are identical except for possible naturally-occurring mutations that may be present in minor amounts.

Another aspect of the invention provides antibodies that bind to 24P4C12 proteins and polypeptides. The most preferred antibodies will specifically bind to a 24P4C12 protein and will not bind (or will bind weakly) to non-24P4C12 proteins and polypeptides. Anti-24P4C12 antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule that binds to its target, i.e., the antigen binding region.

24P4C12 antibodies of the invention may be particularly useful in prostate cancer diagnostic and prognostic assays, and imaging methodologies. Intracellularly expressed antibodies (e.g., single chain antibodies) may be therapeutically useful in treating cancers in which the expression of 24P4C12 is involved, such as for example advanced and metastatic prostate cancers. Also useful in therapeutic methods for treatment of prostate cancer are systemically administered 24P4C12 antibodies that interfere with 24P4C12 function or that target extracellular regions of 24P4C12 for delivery of a toxin or therapeutic molecule. Such delivery of a toxin or therapeutic molecule can be achieved using known methods of conjugating a second molecule to the 24P4C12 antibody or fragment thereof. Similarly, such antibodies may be useful in the treatment, diagnosis, and/or prognosis of other cancers, to the extent 24P4C12 is also expressed or overexpressed in other types of cancer.

The invention also provides various immunological assays useful for the detection and quantification of 24P4C12 and mutant 24P4C12 proteins and polypeptides. Such assays generally comprise one or more 24P4C12 antibodies capable of recognizing and binding a 24P4C12 or mutant 24P4C12 protein, as appropriate, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting prostate cancer and other cancers expressing 24P4C12 are also provided by the invention, including but limited to radioscintigraphic imaging methods using labeled 24P4C12 antibodies. Such assays may be clinically useful in the detection, monitoring, and prognosis of 24P4C12 expressing cancers, such as prostate cancer.

24P4C12 antibodies may also be used in methods for purifying 24P4C12 and mutant 24P4C12 proteins and polypeptides and for isolating 24P4C12 homologues and related molecules. For example, in one embodiment, the method of purifying a 24P4C12 protein comprises incubating a 24P4C12 antibody, which has been coupled to a solid matrix, with a lysate or other solution containing 24P4C12 under conditions that permit the 24P4C12 antibody to bind to 24P4C12; washing the solid matrix to eliminate impurities; and eluting the 24P4C12 from the coupled antibody. Other uses of the 24P4C12 antibodies of the invention include generating anti-idiotypic antibodies that mimic the 24P4C12 protein.

Various methods for the preparation of antibodies are well known in the art. For example, antibodies may be prepared by immunizing a suitable mammalian host using a 24P4C12 protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of 24P4C12 may also be used, such as a 24P4C12 GST-fusion protein. In a particular embodiment, a GST fusion protein comprising all or most of the open reading frame amino acid sequence of FIGS. 1A-1D (SEQ ID NO: 2) may be produced and used as an immunogen to generate appropriate antibodies. In another embodiment, a 24P4C12 peptide may be synthesized and used as an immunogen.

In addition, naked DNA immunization techniques known in the art may be used (with or without purified 24P4C12 protein or 24P4C12 expressing cells) to generate an immune response to the encoded immunogen (for review, see Donnelly et al., 1997, Ann. Rev. Immunol. 15: 617-648).

The amino acid sequence of the 24P4C12 as shown in FIGS. 1A-1D (SEQ ID NO: 2) may be used to select specific regions of the 24P4C12 protein for generating antibodies. For example, hydrophobicity and hydrophilicity analyses of the 24P4C12 amino acid sequence may be used to identify hydrophilic regions in the 24P4C12 structure. Regions of the 24P4C12 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Methods for the generation of 24P4C12 antibodies are further illustrated by way of the examples provided herein.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a 24P4C12 immunogen is conducted generally by injection over a suitable time period and with use of a suitable adjuvant, as is generally understood in the art. During the immunization schedule, titers of antibodies can be taken to determine adequacy of antibody formation.

Polyclonal 24P4C12 antibodies can be prepared using conventional techniques known in the art. A representative protocol for the preparation of such antibodies is described in the Examples that follow. Polyclonal antibodies can be useful for sensitive detection of multiple epitopes associated with 24P4C12.

24P4C12 monoclonal antibodies may be produced by various means well known in the art. For example, immortalized cell lines that secrete a desired monoclonal antibody may be prepared using the standard hybridoma technology of Kohler and Milstein or modifications that immortalize producing B cells, as is generally known. The immortalized cell lines secreting the desired antibodies are screened by immunoassay in which the antigen is the 24P4C12 protein or a 24P4C12 fragment. When the appropriate immortalized cell culture secreting the desired antibody is identified, the cells may be expanded and antibodies produced either from in vitro cultures or from ascites fluid.

The antibodies or fragments may also be produced, using current technology, by recombinant means. Regions that bind specifically to the desired regions of the 24P4C12 protein can also be produced in the context of chimeric or CDR grafted antibodies of multiple species origin. Humanized or human 24P4C12 antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296. Methods for producing fully human monoclonal antibodies include phage display and transgenic methods (for review, see Vaughan et al., 1998, Nature Biotechnology 16: 535-539).

Fully human 24P4C12 monoclonal antibodies may be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45-64 (1993); Burton and Barbas, Human Antibodies from combinatorial libraries. Id., pp 65-82). Fully human 24P4C12 monoclonal antibodies may also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607-614). This method avoids the in vitro manipulation required with phage display technology and efficiently produces high affinity authentic human antibodies.

Reactivity of 24P4C12 antibodies with a 24P4C12 protein may be established by a number of well known means, including western blot, immunoprecipitation, ELISA, and FACS analyses using, as appropriate, 24P4C12 proteins, peptides, 24P4C12-expressing cells or extracts thereof.

A 24P4C12 antibody or fragment thereof of the invention may be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. A second molecule for conjugation to the 24P4C12 antibody can be selected in accordance with the intended use. For example, for therapeutic use, the second molecule can be a toxin or therapeutic agent. Further, bi-specific antibodies specific for two or more 24P4C12 epitopes may be generated using methods generally known in the art. Homodimeric antibodies may also be generated by cross-linking techniques known in the art (e.g., Wolff et al., Cancer Res. 53: 2560-2565).

H38087 Antibodies

The invention also provides antibodies, both polyclonal and monoclonal, directed against H38087. These antibodies can be modified, generated and used in manners analogous to those described above for 24P4C12 antibodies. The ubiquitous expression of H38087, however, makes it likely to be useful as a control for testing 24P4C12-specific therapeutics, and possibly for comparison in 24P4C12 diagnostic applications. A 24P4C12-specific therapeutic that affects H38087 function could be toxic to normal cells. However, a therapeutic that selectively affects 24P4C12, but not H38087, may be less toxic to normal cells. Therefore, H38087 proteins and antibodies can be useful as pre-clinical testing tools for therapeutic modalities directed towards 24P4C12.

24P4C12 Transgenic Animals

Nucleic acids that encode 24P4C12 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In one embodiment, cDNA encoding 24P4C12 can be used to clone genomic DNA encoding 24P4C12 in accordance with established techniques and the genomic sequences used to generate transgenic animals that contain cells that express DNA encoding 24P4C12. Methods for generating transgenic animals, particularly animals such as mice or rats, have become conventional in the art and are described, for example, in U.S. Pat. Nos. 4,736,866 and 4,870,009. Typically, particular cells would be targeted for 24P4C12 transgene incorporation with tissue-specific enhancers. Transgenic animals that include a copy of a transgene encoding 24P4C12 introduced into the germ line of the animal at an embryonic stage can be used to examine the effect of increased expression of DNA encoding 24P4C12. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of 24P4C12 can be used to construct a 24P4C12 "knock out" animal that has a defective or altered gene encoding 24P4C12 as a result of homologous recombination between the endogenous gene encoding 24P4C12 and altered genomic DNA encoding 24P4C12 introduced into an embryonic cell of the animal. For example, cDNA encoding 24P4C12 can be used to clone genomic DNA encoding 24P4C12 in accordance with established techniques. A portion of the genomic DNA encoding 24P4C12 can be deleted or replaced with another gene, such as a gene encoding a selectable marker that can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the 24P4C12 polypeptide.

Likewise, H38087 transgenic animals can be prepared using nucleic acids that encode H38087.

Methods for the Detection of 24P4C12

Another aspect of the present invention relates to methods for detecting 24P4C12 polynucleotides and 24P4C12 proteins and variants thereof, as well as methods for identifying a cell that expresses 24P4C12. 24P4C12 appears to be expressed in the LAPC xenografts that are derived from lymph-node and bone metastasis of prostate cancer and the expression profile of 24P4C12 makes it a potential diagnostic marker for metastasized disease. In this context, the status of 24P4C12 gene products may provide information useful for predicting a variety of factors including susceptibility to advanced stage disease, rate of progression, and/or tumor aggressiveness. As discussed in detail below, the status of 24P4C12 gene products in patient samples may be analyzed by a variety protocols that are well known in the art including immunohistochemical analysis, the variety of Northern blotting techniques including in situ hybridization, RT-PCR analysis (for example on laser capture micro-dissected samples), western blot analysis and tissue array analysis.

More particularly, the invention provides assays for the detection of 24P4C12 polynucleotides in a biological sample, such as serum, bone, prostate, and other tissues, urine, semen, cell preparations, and the like. Detectable 24P4C12 polynucleotides include, for example, a 24P4C12 gene or fragments thereof, 24P4C12 mRNA, alternative splice variant 24P4C12 mRNAs, and recombinant DNA or RNA molecules containing a 24P4C12 polynucleotide. A number of methods for amplifying and/or detecting the presence of 24P4C12 polynucleotides are well known in the art and may be employed in the practice of this aspect of the invention.

In one embodiment, a method for detecting a 24P4C12 mRNA in a biological sample comprises producing cDNA from the sample by reverse transcription using at least one primer; amplifying the cDNA so produced using a 24P4C12 polynucleotides as sense and antisense primers to amplify 24P4C12 cDNAs therein; and detecting the presence of the amplified 24P4C12 cDNA. Optionally, the sequence of the amplified 24P4C12 cDNA can be determined. In another embodiment, a method of detecting a 24P4C12 gene in a biological sample comprises first isolating genomic DNA from the sample; amplifying the isolated genomic DNA using 24P4C12 polynucleotides as sense and antisense primers to amplify the 24P4C12 gene therein; and detecting the presence of the amplified 24P4C12 gene. Any number of appropriate sense and antisense probe combinations may be designed from the nucleotide sequences provided for the 24P4C12 (FIGS. 1A-1D; SEQ ID NO: 1) and used for this purpose.

The invention also provides assays for detecting the presence of a 24P4C12 protein in a tissue or other biological sample such as serum, bone, prostate, and other tissues, urine, cell preparations, and the like. Methods for detecting a 24P4C12 protein are also well known and include, for example, immunoprecipitation, immunohistochemical analysis, western blot analysis, molecular binding assays, ELISA, ELIFA and the like. For example, in one embodiment, a method of detecting the presence of a 24P4C12 protein in a biological sample comprises first contacting the sample with a 24P4C12 antibody, a 24P4C12-reactive fragment thereof, or a recombinant protein containing an antigen binding region of a 24P4C12 antibody; and then detecting the binding of 24P4C12 protein in the sample thereto.

Methods for identifying a cell that expresses 24P4C12 are also provided. In one embodiment, an assay for identifying a cell that expresses a 24P4C12 gene comprises detecting the presence of 24P4C12 mRNA in the cell. Methods for the detection of particular mRNAs in cells are well known and include, for example, hybridization assays using complementary DNA probes (such as in situ hybridization using labeled 24P4C12 riboprobes, northern blot and related techniques) and various nucleic acid amplification assays (such as RT-PCR using complementary primers specific for 24P4C12, and other amplification type detection methods, such as, for example, branched DNA, SISBA, TMA and the like). Alternatively, an assay for identifying a cell that expresses a 24P4C12 gene comprises detecting the presence of 24P4C12 protein in the cell or secreted by the cell. Various methods for the detection of proteins are well known in the art and may be employed for the detection of 24P4C12 proteins and 24P4C12 expressing cells.

24P4C12 expression analysis may also be useful as a tool for identifying and evaluating agents that modulate 24P4C12 gene expression. For example, 24P4C12 expression is significantly upregulated in prostate cancers, and may also be expressed in other cancers. Identification of a molecule or biological agent that could inhibit 24P4C12 expression or over-expression in cancer cells may be of therapeutic value. Such an agent may be identified by using a screen that quantifies 24P4C12 expression by RT-PCR, nucleic acid hybridization or antibody binding.

Monitoring the Status of 24P4C12 and its Products

Assays that evaluate the status of the 24P4C12 gene and 24P4C12 gene products in an individual may provide information on the growth or oncogenic potential of a biological sample from this individual. For example, because 24P4C12 mRNA is so highly expressed in prostate cancers relative to normal tissues, assays that evaluate the relative levels of 24P4C12 mRNA transcripts or proteins in a biological sample may be used to diagnose a disease associated with 24P4C12 disregulation such as cancer and may provide prognostic information useful in defining appropriate therapeutic options. Similarly, assays that evaluate the integrity 24P4C12 nucleotide and amino acid sequences in a biological sample, may also be used in this context.

The finding that 24P4C12 mRNA is so highly expressed in prostate cancers, and not in normal tissue, provides evidence that this gene is associated with disregulated cell growth and therefore identifies this gene and its products as targets that the skilled artisan can use to evaluate biological samples from individuals suspected of having a disease associated with 24P4C12 disregulation. In this context, the evaluation of the expression status of 24P4C12 gene and its products can be used to gain information on the disease potential of a tissue sample. The terms "expression status" in this context is used to broadly refer to the variety of factors involved in the expression, function and regulation of a gene and its products such as the level of mRNA expression, the integrity of the expressed gene products (such as the nucleic and amino acid sequences) and transcriptional and translational modifications to these molecules.

The expression status of 24P4C12 may provide information useful for predicting susceptibility to particular disease stages, progression, and/or tumor aggressiveness. The invention provides methods and assays for determining 24P4C12 expression status and diagnosing cancers that express 24P4C12, such as cancers of the prostate, breast, bladder, lung, bone, colon, pancreatic, testicular, cervical and ovarian cancers. 24P4C12 expression status in patient samples may be analyzed by a number of means well known in the art, including without limitation, immunohistochemical analysis, in situ hybridization, RT-PCR analysis on laser capture micro-dissected samples, western blot analysis of clinical samples and cell lines, and tissue array analysis. Typical protocols for evaluating the expression status of the 24P4C12 gene and gene products can be found, for example in *Current Protocols In Molecular Biology*, Units 2 [Northern Blotting], 4 [Southern Blotting], 15 [Immunoblotting] and 18 [PCR Analysis], Frederick M. Ausubul et al. eds., 1995.

In one aspect, the invention provides methods for monitoring 24P4C12 gene products by determining the status of 24P4C12 gene products expressed by cells in a test tissue sample from an individual suspected of having a disease associated with disregulated cell growth (such as hyperplasia or cancer) and then comparing the status so determined to the status of 24P4C12 gene products in a corresponding normal sample, the presence of aberrant 24P4C12 gene products in the test sample relative to the normal sample providing an indication of the presence of disregulated cell growth within the cells of the individual.

In another aspect, the invention provides assays useful in determining the presence of cancer in an individual, comprising detecting a significant increase in 24P4C12 mRNA or protein expression in a test cell or tissue sample relative to expression levels in the corresponding normal cell or tissue. The presence of significant 24P4C12 expression in these tissues may be useful to indicate the emergence, presence and/or severity of cancer.

In a related embodiment, 24P4C12 expression status may be determined at the protein level rather than at the nucleic acid level. For example, such a method or assay would comprise determining the level of 24P4C12 protein expressed by cells in a test tissue sample and comparing the level so determined to the level of 24P4C12 expressed in a corresponding normal sample. In one embodiment, the presence of 24P4C12 protein is evaluated, for example, using immunohistochemical methods. 24P4C12 antibodies or binding partners capable of detecting 24P4C12 protein expression may be used in a variety of assay formats well known in the art for this purpose.

In other related embodiments, one can evaluate the integrity 24P4C12 nucleotide and amino acid sequences in a biological sample in order to identify perturbations in the structure of these molecules such as insertions, deletions, substitutions and the like. Such embodiments are useful because perturbations in the nucleotide and amino acid sequences are observed in a large number of proteins associated with a growth disregulated phenotype (see e.g. Marrogi et al., J. Cutan. Pathol. 26(8): 369-378 (1999)). In this context, a wide variety of assays for observing perturbations in nucleotide and amino acid sequences are well known in the art. For example, the size and structure of nucleic acid or amino acid sequences of 24P4C12 gene products may be observed by the northern, Southern, western, PCR and DNA sequencing protocols discussed herein. In addition, other methods for observing perturbations in nucleotide and amino acid sequences such as single strand conformation polymorphism analysis are well known in the art (see e.g. U.S. Pat. Nos. 5,382,510 and 5,952,170).

In another related embodiment, the invention provides assays useful in determining the presence of cancer in an individual, comprising detecting a significant change in the 24P4C12 alternative splice variants expressed in a test cell or tissue sample relative to expression levels in the corresponding normal cell or tissue. The monitoring of alternative splice variants of 24P4C12 is useful because changes in the alternative splicing of proteins is suggested as one of the steps in a series of events that lead to the progression of cancers (see e.g. Carstens et al., Oncogene 15(250: 3059-3065 (1997)).

Gene amplification provides an additional method of assessing the status of 24P4C12. Gene amplification may be measured in a sample directly, for example, by conventional Southern blotting, northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

In addition to the tissues discussed above, peripheral blood may be conveniently assayed for the presence of cancer cells, including but not limited to prostate cancers, using RT-PCR to detect 24P4C12 expression. The presence of RT-PCR amplifiable 24P4C12 mRNA provides an indication of the presence of the cancer. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25: 373-384; Ghossein et al., 1995, J. Clin. Oncol. 13: 1195-2000; Heston et al., 1995, Clin. Chem. 41: 1687-1688). RT-PCR assays are well known in the art.

A related aspect of the invention is directed to predicting susceptibility to developing cancer in an individual. In one embodiment, a method for predicting susceptibility to cancer comprises detecting 24P4C12 mRNA or 24P4C12 protein in a tissue sample, its presence indicating susceptibility to cancer, wherein the degree of 24P4C12 mRNA expression present is proportional to the degree of susceptibility. In a specific embodiment, the presence of 24P4C12 in prostate tissue is examined, with the presence of 24P4C12 in the sample providing an indication of prostate cancer susceptibility (or the emergence or existence of a prostate tumor). In a closely related embodiment, one can evaluate the integrity 24P4C12 nucleotide and amino acid sequences in a biological sample in order to identify perturbations in the structure of these molecules such as insertions, deletions, substitutions and the like, with the presence of one or more perturbations in 24P4C12 gene products in the sample providing an indication of cancer susceptibility (or the emergence or existence of a tumor).

Yet another related aspect of the invention is directed to methods for gauging tumor aggressiveness. In one embodiment, a method for gauging aggressiveness of a tumor comprises determining the level of 24P4C12 mRNA or 24P4C12 protein expressed by cells in a sample of the tumor, comparing the level so determined to the level of 24P4C12 mRNA or 24P4C12 protein expressed in a corresponding normal tissue taken from the same individual or a normal tissue reference sample, wherein the degree of 24P4C12 mRNA or 24P4C12 protein expression in the tumor sample relative to the normal sample indicates the degree of aggressiveness. In a specific embodiment, aggressiveness of prostate tumors is evaluated by determining the extent to which 24P4C12 is expressed in the tumor cells, with higher expression levels indicating more aggressive tumors. In a closely related embodiment, one can evaluate the integrity 24P4C12 nucleotide and amino acid sequences in a biological sample in order to identify perturbations in the structure of these molecules such as insertions, deletions, substitutions and the like, with the presence of one or more perturbations indicating more aggressive tumors.

Yet another related aspect of the invention is directed to methods for observing the progression of a malignancy in an individual over time. In one embodiment, methods for observing the progression of a malignancy in an individual over time comprise determining the level of 24P4C12 mRNA or 24P4C12 protein expressed by cells in a sample of the tumor, comparing the level so determined to the level of 24P4C12 mRNA or 24P4C12 protein expressed in an equivalent tissue sample taken from the same individual at a different time, wherein the degree of 24P4C12 mRNA or 24P4C12 protein expression in the tumor sample over time provides information on the progression of the cancer. In a specific embodiment, the progression of a cancer is evaluated by determining the extent to which 24P4C12 expression in the tumor cells alters over time, with higher expression levels indicating a progression of the cancer. In a closely related embodiment, one can evaluate the integrity 24P4C12 nucleotide and amino acid sequences in a biological sample in order to identify perturbations in the structure of these molecules such as insertions, deletions, substitutions and the like, with the presence of one or more perturbations indicating a progression of the cancer.

The above diagnostic approaches may be combined with any one of a wide variety of prognostic and diagnostic protocols known in the art. For example, another embodiment of the invention disclosed herein is directed to methods for observing a coincidence between the expression of 24P4C12 gene and 24P4C12 gene products (or perturbations in 24P4C12 gene and 24P4C12 gene products) and a factor that is associated with malignancy as a means of diagnosing and prognosticating the status of a tissue sample. In this context, a wide variety of factors associated with malignancy may be utilized such as the expression of genes otherwise associated with malignancy (including PSA, PSCA and PSM expression) as well as gross cytological observations (see e.g. Bocking et al., Anal Quant Cytol. 6(2):74-88 (1984); Eptsein, Hum Pathol. February 1995; 26(2):223-9 (1995); Thorson et al., Mod Pathol. June 1998; 11(6):543-51; Baisden et al., Am J Surg Pathol. 23(8):918-24 91999)). Methods for observing a coincidence between the expression of 24P4C12 gene and 24P4C12 gene products (or perturbations in 24P4C12 gene and 24P4C12 gene products) and an additional factor that is associated with malignancy are useful, for example, because the presence of a set or constellation of specific factors that coincide provides information crucial for diagnosing and prognosticating the status of a tissue sample.

In a typical embodiment, methods for observing a coincidence between the expression of 24P4C12 gene and 24P4C12 gene products (or perturbations in 24P4C12 gene and 24P4C12 gene products) and a factor that is associated with malignancy entails detecting the overexpression of 24P4C12 mRNA or protein in a tissue sample, detecting the overexpression of PSA mRNA or protein in a tissue sample, and observing a coincidence of 24P4C12 mRNA or protein and PSA mRNA or protein overexpression. In a specific embodiment, the expression of 24P4C12 and PSA mRNA in prostate tissue is examined. In a preferred embodiment, the coincidence of 24P4C12 and PSA mRNA overexpression in the sample provides an indication of prostate cancer, prostate cancer susceptibility or the emergence or existence of a prostate tumor.

Methods for detecting and quantifying the expression of 24P4C12 mRNA or protein are described herein and use standard nucleic acid and protein detection and quantification technologies well known in the art. Standard methods for the detection and quantification of 24P4C12 mRNA include in situ hybridization using labeled 24P4C12 riboprobes, northern blot and related techniques using 24P4C12 polynucleotide probes, RT-PCR analysis using primers specific for 24P4C12, and other amplification type detection methods, such as, for example, branched DNA, SISBA, TMA and the like. In a specific embodiment, semi-quantitative RT-PCR may be used to detect and quantify 24P4C12 mRNA expression as described in the Examples that follow. Any number of primers capable of amplifying 24P4C12 may be used for this purpose, including but not limited to the various primer sets specifically described herein. Standard methods for the detection and quantification of protein may be used for this purpose. In a specific embodiment, polyclonal or monoclonal antibodies specifically reactive with the wild-type 24P4C12 protein may be used in an immunohistochemical assay of biopsied tissue.

Identifying Molecules that Interact with 24P4C12

The 24P4C12 protein sequences disclosed herein allow the skilled artisan to identify molecules that interact with them via any one of a variety of art accepted protocols. For example one can utilize one of the variety of so-called interaction trap systems (also referred to as the "two-hybrid assay"). In such systems, molecules that interact reconstitute a transcription factor and direct expression of a reporter gene, the expression of which is then assayed. Typical systems identify protein-protein interactions in vivo through reconstitution of a eukaryotic transcriptional activator and are disclosed for example in U.S. Pat. Nos. 5,955,280, 5,925,523, 5,846,722 and 6,004,746.

Alternatively, one can identify molecules that interact with 24P4C12 protein sequences by screening peptide libraries. In such methods, peptides that bind to selected receptor molecules such as 24P4C12 are identified by screening libraries that encode a random or controlled collection of amino acids. Peptides encoded by the libraries are expressed as fusion proteins of bacteriophage coat proteins, and bacteriophage particles are then screened against the receptors of interest. Peptides having a wide variety of uses, such as therapeutic or diagnostic reagents, may thus be identified without any prior information on the structure of the expected ligand or receptor molecule. Typical peptide libraries and screening methods that can be used to identify molecules that interact with 24P4C12 protein sequences are disclosed for example in U.S. Pat. Nos. 5,723,286 and 5,733,731.

Alternatively, cell lines expressing 24P4C12 can be used to identify protein-protein interactions mediated by 24P4C12. This possibility can be examined using immunoprecipitation techniques as shown by others (Hamilton B J, et al. Biochem. Biophys. Res. Commun. 1999, 261:646-51). Typically 24P4C12 protein can be immunoprecipitated from 24P4C12 expressing prostate cancer cell lines using anti-24P4C12 antibodies. Alternatively, antibodies against His-tag can be used in a cell line engineered to express 24P4C12 (using, e.g., vectors mentioned above). The immuno-precipitated complex can be examined for protein association by procedures such as western blotting, $^{35}$S-methionine labeling of proteins, protein microsequencing, silver staining and two dimensional gel electrophoresis.

Related embodiments of such screening assays include methods for identifying small molecules that interact with 24P4C12. Typical methods are discussed for example in U.S. Pat. No. 5,928,868 and include methods for forming hybrid ligands in which at least one ligand is a small molecule. In an illustrative embodiment, the hybrid ligand is introduced into cells that in turn contain a first and a second expression vector. Each expression vector includes DNA for expressing a hybrid protein that encodes a target protein linked to a coding sequence for a transcriptional module. Each cell further contains a reporter gene, the expression of which is conditioned on the proximity of the first and second hybrid proteins to each other, an event that occurs only if the hybrid ligand binds to target sites on both hybrid proteins. Those cells that express the reporter gene are selected and the unknown small molecule or the unknown hybrid protein is identified.

A typical embodiment of this invention consists of a method of screening for a molecule that interacts with a 24P4C12 amino acid sequence shown in FIGS. 1A-1D, comprising the steps of contacting a population of molecules with the 24P4C12 amino acid sequence, allowing the population of molecules and the 24P4C12 amino acid sequence to interact under conditions that facilitate an interaction, determining the presence of a molecule that interacts with the 24P4C12 amino acid sequence and then separating molecules that do not interact with the 24P4C12 amino acid sequence from molecules that do interact with the 24P4C12 amino acid sequence. In a specific embodiment, the method further includes purifying a molecule that interacts with the 24P4C12 amino acid sequence. In a preferred embodiment, the 24P4C12 amino acid sequence is contacted with a library of peptides.

Therapeutic Methods and Compositions

The identification of 24P4C12 as a prostate tumor-associated protein, opens a number of therapeutic approaches to the treatment of such cancers. As discussed above, it is possible that 24P4C12 functions as a receptor involved in activating or modulating proliferation signals, and that it presents epitopes at the cell surface that can be targeted for therapy.

The expression profile of 24P4C12 is reminiscent of the MAGEs, PSA and PMSA, which are tissue-specific genes that are up-regulated in melanomas and other cancers (Van den Eynde and Boon, Int J Clin Lab Res. 27:81-86, 1997). Due to their tissue-specific expression and high expression levels in cancer, these molecules are currently being investigated as targets for cancer vaccines (Durrant, Anticancer Drugs 8:727-733, 1997; Reynolds et al., Int J Cancer 72:972-976, 1997). The expression pattern of 24P4C12 provides evidence that it is likewise a potential target for a cancer vaccine approach to prostate cancer and other cancers, as its expression is limited in normal tissues. Its structural features as a potential receptor also provides evidence that 24P4C12 may be a small molecule target, as well as a target for antibody-based therapeutic strategies.

Accordingly, therapeutic approaches targeting extracellular portions of 24P4C12, or aimed at inhibiting the activity of the 24P4C12 protein are expected to be useful for patients suffering from prostate cancer, testicular cancer, and other cancers expressing 24P4C12. The therapeutic approaches aimed at inhibiting the activity of the 24P4C12 protein generally fall into two classes. One class comprises various methods for inhibiting the binding or association of the 24P4C12 protein with its binding partner or with other proteins. Another class comprises a variety of methods for inhibiting the transcription of the 24P4C12 gene or translation of 24P4C12 mRNA.

24P4C12 as a Cell Surface Target for Antibody-Based Therapy

The structural features of 24P4C12 indicate that this molecule is likely a cell surface antigen, providing an attractive target for antibody-based therapeutic strategies. Because 24P4C12 is over-expressed on cancer cells relative to normal cells, systemic administration of 24P4C12-immunoreactive compositions would be expected to exhibit relatively good sensitivity with minimal toxic, non-specific and/or non-target effects caused by binding of the immunotherapeutic molecule to non-target organs and tissues. Antibodies specifically reactive with extracellular domains of 24P4C12 can be useful to treat 24P4C12-expressing cancers systemically, either as conjugates with a toxin or therapeutic agent, or as naked antibodies capable of inhibiting cell proliferation or function.

24P4C12 antibodies can be introduced into a patient such that the antibody binds to 24P4C12 on the cancer cells and mediates the destruction of the cells and the tumor and/or inhibits the growth of the cells or the tumor. Mechanisms by which such antibodies exert a therapeutic effect may include complement-mediated cytolysis, antibody-dependent cellular cytotoxicity, modulating the physiological function of 24P4C12, inhibiting ligand binding or signal transduction pathways, modulating tumor cell differentiation, altering tumor angiogenesis factor profiles, and/or by inducing apoptosis. 24P4C12 antibodies can be conjugated to toxic or therapeutic agents and used to deliver the toxic or therapeutic agent directly to 24P4C12-bearing tumor cells. Examples of toxic agents include, but are not limited to, calchemicin, maytansinoids, radioisotopes such as $^{131}$I, ytrium, and bismuth.

Cancer immunotherapy using anti-24P4C12 antibodies may follow the teachings generated from various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186; Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166); Velders et al., 1995, Cancer Res. 55:4398-4403), and breast cancer (Shepard et al., 1991, J. Clin. Immunol. 11:117-127). Some therapeutic approaches involve conjugation of naked antibody to a toxin, such as the conjugation of $^{131}$I to anti-CD20 antibodies (e.g., Rituxan™, IDEC Pharmaceuticals Corp., naked antibody; Coulter Pharmaceuticals, Palo Alto, Calif., $^{131}$I-anti-CD20 conjugate), while others involve co-administration of antibodies and other therapeutic agents, such as Herceptin™ (trastuzumab) with paclitaxel (Genentech, Inc.). For treatment of prostate cancer, for example, 24P4C12 antibodies can be administered in conjunction with radiation, chemotherapy or hormone ablation.

Although 24P4C12 antibody therapy may be useful for all stages of cancer, antibody therapy may be particularly appropriate in advanced or metastatic cancers. Treatment with the antibody therapy of the invention may be indicated for patients who have received previously one or more chemotherapy, while combining the antibody therapy of the invention with a chemotherapeutic or radiation regimen may be preferred for patients who have not received chemotherapeutic treatment. Additionally, antibody therapy may enable the use of reduced dosages of concomitant chemotherapy, particularly for patients who do not tolerate the toxicity of the chemotherapeutic agent very well.

It may be desirable for some cancer patients to be evaluated for the presence and level of 24P4C12 expression, preferably using immunohistochemical assessments of tumor tissue, quantitative 24P4C12 imaging, or other techniques capable of reliably indicating the presence and degree of 24P4C12 expression. Immunohistochemical analysis of tumor biopsies or surgical specimens may be preferred for this purpose. Methods for immunohistochemical analysis of tumor tissues are well known in the art.

Anti-24P4C12 monoclonal antibodies useful in treating prostate and other cancers include those that are capable of initiating a potent immune response against the tumor and those that are capable of direct cytotoxicity. In this regard, anti-24P4C12 monoclonal antibodies (mAbs) may elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, anti-24P4C12 mAbs that exert a direct biological effect on tumor growth are useful in the practice of the invention. Potential mechanisms by which such directly cytotoxic mAbs may act include inhibition of cell growth, modulation of cellular differentiation, modulation of tumor angiogenesis factor profiles, and the induction of apoptosis. The mechanism by which a particular anti-24P4C12 mAb exerts an anti-tumor effect may be evaluated using any number of in vitro assays designed to determine ADCC, ADMMC, complement-mediated cell lysis, and so forth, as is generally known in the art.

The use of murine or other non-human monoclonal antibodies, or human/mouse chimeric mAbs may induce moderate to strong immune responses in some patients. In some cases, this will result in clearance of the antibody from circulation and reduced efficacy. In the most severe cases, such an immune response may lead to the extensive formation of immune complexes which, potentially, can cause renal failure. Accordingly, preferred monoclonal antibodies used in the practice of the therapeutic methods of the invention are those that are either fully human or humanized and that bind specifically to the target 24P4C12 antigen with high affinity but exhibit low or no antigenicity in the patient.

Therapeutic methods of the invention contemplate the administration of single anti-24P4C12 mAbs as well as combinations, or cocktails, of different mAbs. Such mAb cocktails may have certain advantages inasmuch as they contain mAbs that target different epitopes, exploit different effector mechanisms or combine directly cytotoxic mAbs with mAbs that rely on immune effector functionality. Such mAbs in combination may exhibit synergistic therapeutic effects. In addition, the administration of anti-24P4C12 mAbs may be combined with other therapeutic agents, including but not limited to various chemotherapeutic agents, androgen-blockers, and immune modulators (e.g., IL-2, GM-CSF). The anti-24P4C12 mAbs may be administered in their "naked" or unconjugated form, or may have therapeutic agents conjugated to them.

The anti-24P4C12 antibody formulations may be administered via any route capable of delivering the antibodies to the tumor site. Potentially effective routes of administration include, but are not limited to, intravenous, intraperitoneal, intramuscular, intratumor, intradermal, and the like. Treatment will generally involve the repeated administration of the anti-24P4C12 antibody preparation via an acceptable route of administration such as intravenous injection (IV), typically at a dose in the range of about 0.1 to about 10 mg/kg body weight. Doses in the range of 10-500 mg mAb per week may be effective and well tolerated.

Based on clinical experience with the Herceptin mAb in the treatment of metastatic breast cancer, an initial loading dose of approximately 4 mg/kg patient body weight IV followed by weekly doses of about 2 mg/kg IV of the anti-24P4C12 mAb preparation may represent an acceptable dosing regimen. Preferably, the initial loading dose is administered as a 90 minute or longer infusion. The periodic maintenance dose may be administered as a 30 minute or longer infusion, provided the initial dose was well tolerated. However, as one of skill in the art will understand, various factors will influence the ideal dose regimen in a particular case. Such factors may include, for example, the binding affinity and half life of the Ab or mAbs used, the degree of 24P4C12 expression in the patient, the extent of circulating shed 24P4C12 antigen, the desired steady-state antibody concentration level, frequency of treatment, and the influence of chemotherapeutic agents used in combination with the treatment method of the invention.

Optimally, patients should be evaluated for the level of circulating shed 24P4C12 antigen in serum in order to assist in the determination of the most effective dosing regimen and related factors. Such evaluations may also be used for monitoring purposes throughout therapy, and may be useful to gauge therapeutic success in combination with evaluating other parameters (such as serum PSA levels in prostate cancer therapy).

Inhibition of 24P4C12 Protein Function

The invention includes various methods and compositions for inhibiting the binding of 24P4C12 to its binding partner or ligand, or its association with other protein(s) as well as methods for inhibiting 24P4C12 function.

Inhibition of 24P4C12 with Intracellular Antibodies

In one approach, recombinant vectors encoding single chain antibodies that specifically bind to 24P4C12 may be introduced into 24P4C12 expressing cells via gene transfer technologies, wherein the encoded single chain anti-24P4C12 antibody is expressed intracellularly, binds to 24P4C12 protein, and thereby inhibits its function. Methods for engineering such intracellular single chain antibodies are well known. Such intracellular antibodies, also known as “intrabodies”, may be specifically targeted to a particular compartment within the cell, providing control over where the inhibitory activity of the treatment will be focused. This technology has been successfully applied in the art (for review, see Richardson and Marasco, 1995, TIBTECH vol. 13). Intrabodies have been shown to virtually eliminate the expression of otherwise abundant cell surface receptors. See, for example, Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337.

Single chain antibodies comprise the variable domains of the heavy and light chain joined by a flexible linker polypeptide, and are expressed as a single polypeptide. Optionally, single chain antibodies may be expressed as a single chain variable region fragment joined to the light chain constant region. Well known intracellular trafficking signals may be engineered into recombinant polynucleotide vectors encoding such single chain antibodies in order to precisely target the expressed intrabody to the desired intracellular compartment. For example, intrabodies targeted to the endoplasmic reticulum (ER) may be engineered to incorporate a leader peptide and, optionally, a C-terminal ER retention signal, such as the KDEL amino acid motif. Intrabodies intended to exert activity in the nucleus may be engineered to include a nuclear localization signal. Lipid moieties may be joined to intrabodies in order to tether the intrabody to the cytosolic side of the plasma membrane. Intrabodies may also be targeted to exert function in the cytosol. For example, cytosolic intrabodies may be used to sequester factors within the cytosol, thereby preventing them from being transported to their natural cellular destination.

In order to specifically direct the expression of such intrabodies to particular tumor cells, the transcription of the intrabody may be placed under the regulatory control of an appropriate tumor-specific promoter and/or enhancer. In order to target intrabody expression specifically to prostate, for example, the PSA promoter and/or promoter/enhancer may be utilized (See, for example, U.S. Pat. No. 5,919,652).

Inhibition of 24P4C12 with Recombinant Proteins

In another approach, recombinant molecules that are capable of binding to 24P4C12 thereby preventing 24P4C12 from accessing/binding to its binding partner(s) or associating with other protein(s) are used to inhibit 24P4C12 function. Such recombinant molecules may, for example, contain the reactive part(s) of a 24P4C12 specific antibody molecule. In a particular embodiment, the 24P4C12 binding domain of a 24P4C12 binding partner may be engineered into a dimeric fusion protein comprising two 24P4C12 ligand binding domains linked to the Fc portion of a human IgG, such as human IgG1. Such IgG portion may contain, for example, the $C_H2$ and $C_H3$ domains and the hinge region, but not the $C_H1$ domain. Such dimeric fusion proteins may be administered in soluble form to patients suffering from a cancer associated with the expression of 24P4C12, where the dimeric fusion protein specifically binds to 24P4C12 thereby blocking 24P4C12 interaction with a binding partner. Such dimeric fusion proteins may be further combined into multimeric proteins using known antibody linking technologies.

Inhibition of 24P4C12 Transcription or Translation

Within another class of therapeutic approaches, the invention provides various methods and compositions for inhibiting the transcription of the 24P4C12 gene. Similarly, the invention also provides methods and compositions for inhibiting the translation of 24P4C12 mRNA into protein.

In one approach, a method of inhibiting the transcription of the 24P4C12 gene comprises contacting the 24P4C12 gene with a 24P4C12 antisense polynucleotide. In another approach, a method of inhibiting 24P4C12 mRNA translation comprises contacting the 24P4C12 mRNA with an antisense polynucleotide. In another approach, a 24P4C12 specific ribozyme may be used to cleave the 24P4C12 message, thereby inhibiting translation. Such antisense and ribozyme based methods may also be directed to the regulatory regions of the 24P4C12 gene, such as the 24P4C12 promoter and/or enhancer elements. Similarly, proteins capable of inhibiting a 24P4C12 gene transcription factor may be used to inhibit 24P4C12 mRNA transcription. The various polynucleotides and compositions useful in the aforementioned methods have been described above. The use of antisense and ribozyme molecules to inhibit transcription and translation is well known in the art.

Other factors that inhibit the transcription of 24P4C12 through interfering with 24P4C12 transcriptional activation may also be useful for the treatment of cancers expressing 24P4C12. Similarly, factors that are capable of interfering with 24P4C12 processing may be useful for the treatment of cancers expressing 24P4C12. Cancer treatment methods utilizing such factors are also within the scope of the invention.

General Considerations for Therapeutic Strategies

Gene transfer and gene therapy technologies may be used for delivering therapeutic polynucleotide molecules to tumor cells synthesizing 24P4C12 (i.e., antisense, ribozyme, polynucleotides encoding intrabodies and other 24P4C12 inhibitory molecules). A number of gene therapy approaches are known in the art. Recombinant vectors encoding 24P4C12 antisense polynucleotides, ribozymes, factors capable of interfering with 24P4C12 transcription, and so forth, may be delivered to target tumor cells using such gene therapy approaches.

The above therapeutic approaches may be combined with any one of a wide variety of chemotherapy or radiation therapy regimens. These therapeutic approaches may also enable the use of reduced dosages of chemotherapy and/or less frequent administration, particularly in patients that do not tolerate the toxicity of the chemotherapeutic agent well.

The anti-tumor activity of a particular composition (e.g., antisense, ribozyme, intrabody), or a combination of such compositions, may be evaluated using various in vitro and in vivo assay systems. In vitro assays for evaluating therapeutic potential include cell growth assays, soft agar assays and other assays indicative of tumor promoting activity, binding assays capable of determining the extent to which a therapeutic composition will inhibit the binding of 24P4C12 to a binding partner, etc.

In vivo, the effect of a 24P4C12 therapeutic composition may be evaluated in a suitable animal model. For example, xenogenic prostate cancer models wherein human prostate cancer explants or passaged xenograft tissues are introduced into immune compromised animals, such as nude or SCID mice, are appropriate in relation to prostate cancer and have been described (Klein et al., 1997, Nature Medicine 3: 402-408). For example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy may be predicted using assays that measure inhibition of tumor formation, tumor regression or metastasis, and the like. See, also, the Examples below.

In vivo assays that qualify the promotion of apoptosis may also be useful in evaluating potential therapeutic compositions. In one embodiment, xenografts from bearing mice treated with the therapeutic composition may be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods may be formulated into pharmaceutical compositions comprising a carrier suitable for the desired delivery method. Suitable carriers include any material that when combined with the therapeutic composition retains the anti-tumor function of the therapeutic composition and is non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile sodium chloride for injection, USP. Therapeutic protein preparations may be lyophilized and stored as sterile powders, preferably under vacuum, and then reconstituted in bacteriostatic water containing, for example, benzyl alcohol preservative, or in sterile water prior to injection.

Dosages and administration protocols for the treatment of cancers using the foregoing methods will vary with the method and the target cancer and will generally depend on a number of other factors appreciated in the art.

Cancer Vaccines

The invention further provides cancer vaccines comprising a 24P4C12 protein or fragment thereof, as well as DNA based vaccines. Preferably, the vaccine comprises an immunogenic portion of a 24P4C12 protein or polypeptide. In view of the tissue-restricted expression of 24P4C12, 24P4C12 cancer vaccines are expected to be effective at specifically preventing and/or treating 24P4C12 expressing cancers without creating non-specific effects on non-target tissues. The use of a tumor antigen in a vaccine for generating humoral and cell-mediated immunity for use in anti-cancer therapy is well known in the art and has been employed in prostate cancer using human PSMA and rodent PAP immunogens (Hodge et al., 1995, Int. J. Cancer 63: 231-237; Fong et al., 1997, J. Immunol. 159: 3113-3117). Such methods can be readily practiced by employing a 24P4C12 protein, or fragment thereof, or a 24P4C12-encoding nucleic acid molecule and recombinant vectors capable of expressing and appropriately presenting the 24P4C12 immunogen.

For example, viral gene delivery systems may be used to deliver a 24P4C12-encoding nucleic acid molecule. Various viral gene delivery systems that can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658-663). Non-viral delivery systems may also be employed by using naked DNA encoding a 24P4C12 protein or fragment thereof introduced into the patient (e.g., intramuscularly) to induce an anti-tumor response. In one embodiment, the full-length human 24P4C12 cDNA may be employed. In another embodiment, 24P4C12 nucleic acid molecules encoding specific cytotoxic T lymphocyte (CTL) epitopes may be employed. CTL epitopes can be determined using specific algorithms (e.g., Epimer, Brown University) to identify peptides within a 24P4C12 protein that are capable of optimally binding to specified HLA alleles.

Various ex vivo strategies may also be employed. One approach involves the use of dendritic cells to present 24P4C12 antigen to a patient's immune system. Dendritic cells express MHC class I and II, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28: 65-69; Murphy et al., 1996, Prostate 29: 371-380). Dendritic cells can be used to present 24P4C12 peptides to T cells in the context of MHC class I and II molecules. In one embodiment, autologous dendritic cells are pulsed with 24P4C12 peptides capable of binding to MHC molecules. In another embodiment, dendritic cells are pulsed with the complete 24P4C12 protein. Yet another embodiment involves engineering the overexpression of the 24P4C12 gene in dendritic cells using various implementing vectors known in the art, such as adenovirus (Arthur et al., 1997, Cancer Gene Ther. 4: 17-25), retrovirus (Henderson et al., 1996, Cancer Res. 56: 3763-3770), lentivirus, adeno-associated virus, DNA transfection (Ribas et al., 1997, Cancer Res. 57: 2865-2869), and tumor-derived RNA transfection (Ashley et al., 1997, J. Exp. Med. 186: 1177-1182).

Cells expressing 24P4C12 may also be engineered to express immune modulators, such as GM-CSF, and used as immunizing agents.

Anti-idiotypic anti-24P4C12 antibodies can also be used in anti-cancer therapy as a vaccine for inducing an immune response to cells expressing a 24P4C12 protein. Specifically, the generation of anti-idiotypic antibodies is well known in the art and can readily be adapted to generate anti-idiotypic anti-24P4C12 antibodies that mimic an epitope on a 24P4C12 protein (see, for example, Wagner et al., 1997, Hybridoma 16: 33-40; Foon et al., 1995, J Clin Invest 96: 334-342; Herlyn et al., 1996, Cancer Immunol Immunother 43: 65-76). Such an anti-idiotypic antibody can be used in cancer vaccine strategies.

Genetic immunization methods may be employed to generate prophylactic or therapeutic humoral and cellular immune responses directed against cancer cells expressing 24P4C12. Constructs comprising DNA encoding a 24P4C12 protein/immunogen and appropriate regulatory sequences may be injected directly into muscle or skin of an individual, such that the cells of the muscle or skin take-up the construct and express the encoded 24P4C12 protein/immunogen. Expression of the 24P4C12 protein immunogen results in the generation of prophylactic or therapeutic humoral and cellular immunity against prostate cancers. Various prophylactic and therapeutic genetic immunization techniques known in the art may be used (for review, see information and references published at Internet address www.genweb.com).

Kits

For use in the diagnostic and therapeutic applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for a 24P4C12 (and/or H38087) protein or a 24P4C12 (and/or H38087) gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the on the container to indicate that the composition is used for a specific therapy or non-therapeutic application, and may also indicate directions for either in vivo or in vitro use, such as those described above.

The 24P4C12 cDNA was deposited under the terms of the Budapest Treaty with the American Type Culture Collection (ATCC; 10801 University Blvd., Manassas, Va. 20110-2209 USA) as plasmids p24P4C12-GTE9 and p24P4C12-GTE5 on Feb. 2 and 26, 1999, respectively, and have been accorded ATCC Designation Numbers 207084 and 207129.

EXAMPLES

Various aspects of the invention are further described and illustrated by way of the several examples that follow, none of which are intended to limit the scope of the invention.

Example 1

SSH-Generated Isolation of cDNA Fragment of the 24P4C12 Gene

Materials and Methods

LAPC Xenografts

LAPC xenografts were obtained from Dr. Charles Sawyers (UCLA) and generated as described (Klein et al, 1997, Nature Med. 3:402-408; Craft et al., 1999, Cancer Res. 59:5030-5036). Androgen dependent and independent LAPC-4 xenografts (LAPC-4 AD and AI, respectively) were grown in intact male SCID mice or in castrated males, respectively, and were passaged as small tissue chunks in recipient males. LAPC-4 AI xenografts were derived from LAPC-4 AD tumors. To generate the AI xenografts, male mice bearing LAPC AD tumors were castrated and maintained for 2-3 months. After the LAPC tumors re-grew, the tumors were harvested and passaged in castrated males or in female SCID mice.

Cell Lines

Human cell lines (e.g., HeLa) were obtained from the ATCC and were maintained in DMEM with 5% fetal calf serum.

RNA Isolation

Tumor tissue and cell lines were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides

The following HPLC purified oligonucleotides were used.

```
DPNCDN (cDNA synthesis primer):
5'TTTTGATCAAGCTT303'                             (SEQ ID NO: 34)

Adaptor 1:
5'CTAATACGACTCACTATAGGGCTCGAGCGGCCGCCCGGGCAG3'   (SEQ ID NOS: 35, 36, respectively)
                                   3'GGCCCGTCCTAG5'
```

-continued

```
Adaptor 2:
5'GTAATACGACTCACTATAGGGCAGCGTGGTCGCGGCCGAG3'     (SEQ ID NOS: 37, 38, respectively)
                          3'CGGCTCCTAG5'

PCR primer 1:
5'CTAATACGACTCACTATAGGGC3'                       (SEQ ID NO: 39)

Nested primer (NP)1:
5'TCGAGCGGCCGCCCGGGCAGGA3'                       (SEQ ID NO: 40)

Nested primer (NP)2:
5'AGCGTGGTCGCGGCCGAGGA3'                         (SEQ ID NO: 41)
```

Suppression Subtractive Hybridization

Suppression subtractive hybridization (SSH) was used to identify cDNAs corresponding to 24P4C12s that may be differentially expressed in prostate cancer. The SSH reaction utilized cDNA from two different prostate tissue sources, subtracting BPH (benign prostatic hyperplasia) cDNA from LAPC-4 AD cDNA. The LAPC-4 AD cDNA was used as the source of the "tester", while the BPH cDNA was used as the source of the "driver".

Double stranded cDNAs corresponding to tester and driver cDNAs were synthesized from 2 μg of poly(A)+ RNA isolated from the relevant xenograft tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs. at 37° C. Digested cDNA was extracted with phenol/chloroform (1:1) and ethanol precipitated.

Driver cDNA was generated by combining in a 1:1 ratio Dpn II digested cDNA from the relevant xenograft source (see above) with a mix of digested cDNAs derived from human benign prostatic hyperplasia (BPH), the human cell lines HeLa, 293, A431, Colo205, and mouse liver.

Tester cDNA was generated by diluting 1 μl of Dpn II digested cDNA from the relevant xenograft source (see above) (400 ng) in 5 μl of water. The diluted cDNA (2 μl, 160 ng) was then ligated to 2 μl of Adaptor 1 and Adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) Adaptor 1- and Adaptor 2-ligated tester cDNA. In a final volume of 4 μl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification Cloning and Sequencing of Gene Fragments Generated from SSH To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10×reaction buffer (CLONTECH) and 0.5 μl 50× Advantage cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10-12 cycles of 94° C. for 10 sec, 68° C. for 30 sec, 72° C. for 1.5 minutes. The PCR products were analyzed using 2% agarose gel electrophoresis.

The PCR products were inserted into pCR2.1 using the T/A vector cloning kit (Invitrogen). Transformed *E. coli* were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis

First strand cDNAs were generated from 1 μg of mRNA with oligo (dT)12-18 priming using the Gibco-BRL Superscript Preamplification system. The manufacturers protocol was used and included an incubation for 50 min at 42° C. with reverse transcriptase followed by RNAse H treatment at 37° C. for 20 min. After completing the reaction, the volume was increased to 200 μl with water prior to normalization. First strand cDNAs from 16 different normal human tissues were obtained from Clontech.

Normalization of the first strand cDNAs from multiple tissues was performed by using the primers 5'atatcgccgcgctcgtcgtcgacaa3' (SEQ ID NO: 42) and 5'agccacacgcagctcattgtagaagg 3' (SEQ ID NO: 43) to amplify β-actin. First strand cDNA (5 μl) was amplified in a total volume of 50 μl containing 0.4 μM primers, 0.2 μM each dNTPs, 1×PCR buffer (Clontech, 10 mM Tris-HCL, 1.5 mM MgCl2, 50 mM KCl, pH 8.3) and 1× Klentaq DNA polymerase (Clontech). Five μl of the PCR reaction was removed at 18, 20, and 22 cycles and used for agarose gel electrophoresis. PCR was performed using an MJ Research thermal cycler under the following conditions: initial denaturation was at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization were required to achieve equal band intensities in all tissues after 22 cycles of PCR.

To determine expression levels of the 24P4C12 gene, 5 μl of normalized first strand cDNA was analyzed by PCR using 25, 30, and 35 cycles of amplification using the following primer pairs, which were designed with the assistance of (MIT; for details, see, www.genome.wi.mit.edu):

```
5'- agatgaggaggaggacaaaggtg - 3'   (SEQ ID NO: 44)

5'- actgctgggaggagtaccgagtg - 3'   (SEQ ID NO: 45)
```

Semi quantitative expression analysis was achieved by comparing the PCR products at cycle numbers that give light band intensities.

Results

The SSH experiments described in the Materials and Methods, supra, led to the isolation of numerous candidate gene fragment clones (SSH clones). All candidate clones were sequenced and subjected to homology analysis against all sequences in the major public gene and EST databases in order to provide information on the identity of the corresponding gene and to help guide the decision to analyze a particular gene for differential expression. In general, gene fragments which had no homology to any known sequence in any of the searched databases, and thus considered to represent novel genes, as well as gene fragments showing homology to previously sequenced expressed sequence tags (ESTs), were subjected to differential expression analysis by RT-PCR and/or northern analysis.

One of the SHH clones, comprising about 160 bp, encodes a putative open reading frame (ORF) of 53 amino acids and exhibits significant homology to an EST derived from a colon tumor library (FIG. 1E; SEQ ID NOS: 3, 4). This SSH clone, designated 24P4C12, was used to design primers for RT-PCR expression analysis of the 24P4C12 gene in various tissues. RT-PCR analysis showed that 24P4C12 is expressed in all the LAPC xenografts and normal prostate at approximately equal levels (FIG. 2A). RT-PCR analysis of first strand cDNA derived from 16 normal tissues showed expression in colon, prostate, kidney and lung after 25 cycles of amplification (FIGS. 2B and 2C). Northern blot analysis using the 24P4C12 SSH fragment as probe shows the highest expression of an approximately 3 kb 24P4C12 transcript in LAPC-9AD, followed by LAPC-4 AD (FIGS. 3A-3C).

Example 2

Cloning of Full Length 24P4C12 cDNAs

Full length cDNAs encoding the 24P4C12 gene were isolated from a normal prostate library and sequenced. Two of the isolated clones, designated 24P4C12-GTE9 (containing most of the coding region of the 24P4C12 gene) and 24P4C12-GTE5 (containing the entire coding region of the 24P4C12 gene), were deposited as plasmids p24P4C12-GTE9 and p24P4C12-GTE5 with the ATCC (Manassas, Va.) on Feb. 2 and 26, 1999, respectively, and have been accorded ATCC Designation Numbers 207084 and 207129, respectively. These two clones, as well as another clone encoding most of the 24P4C12 coding region, 24P4C12-GTE4, had overlapping nucleotide sequences which were combined to generate the complete coding and partial non-coding sequence of the 24P4C12 gene as shown in FIGS. 1A-1D (SEQ ID NO: 1).

The 2587 bp 24P4C12 cDNA sequence shown in FIGS. 1A-1D (SEQ ID NO: 1) encodes an ORF of 710 amino acids with significant homology to the mouse gene NG22 and the *C. elegans* gene CEESB82F. An amino acid sequence alignment of the human 24P4C12 protein encoded by the cDNA of FIGS. 1A-1D (SEQ ID NO: 2) and the murine NG22 gene products is shown in FIGS. 4A-4B.

NG22 was recently identified as one of many ORFs within a genomic BAC clone that encompasses the MHC class III in the mouse genome. Both NG22 and CEESB82F appear to be genes that contain 12 transmembrane domains. The 24P4C12 cDNA sequence shown in FIGS. 1A-1D (SEQ ID NO: 1) contains 13 potential transmembrane domains. 12-transmembrane transporter proteins are known (Kitty and Amara, 1992, Curr. Opin. Biotechnology 3: 675-682). Due to the putative secondary structure of 24P4C12, it is possible that the 24P4C12 protein functions as a cell surface membrane pump or transporter.

Example 3

24P4C12 Gene Expression Analysis

24P4C12 mRNA expression in normal human tissues was analyzed by northern blotting of multiple tissue blots (Clontech; Palo Alto, Calif.), comprising a total of 16 different normal human tissues, using labeled 24P4C12 SSH fragment (Example 1) as a probe. RNA samples were quantitatively normalized with a β-actin probe. Northern blot analysis showed expression primarily in prostate and colon, with lower expression detected in kidney, and significantly lower expression detected in pancreas, lung and placenta.

To analyze 24P4C12 expression in cancer tissues, northern blotting was performed on RNA derived from the LAPC xenografts, and several prostate and non-prostate cancer cell lines. The results show high expression levels of 24P4C12 in LAPC-4 AD, LAPC-4 AI, LAPC-9 AD, LNCaP and LAPC-4 cell line (FIG. 3, FIG. 5). Very high levels are detected in LAPC-3 AI (FIG. 5). Lower levels are detected in LAPC-9 AI. More detailed analysis of the xenografts shows that 24P4C12 is highly expressed in the xenografts even when grown within the tibia of mice (FIG. 5). Northern analysis also shows that 24P4C12 is expressed in the normal prostate and prostate tumor tissues derived from prostate cancer patients (FIG. 6A). These results suggest that 24P4C12 is a prostate gene that is highly expressed in prostate cancer and may have a utility as a drug or antibody target in prostate cancer.

Example 4

Generation of 24P4C12 Polyclonal Antibodies

To generate polyclonal sera to 24P4C12, a peptide was synthesized corresponding to amino acids 1-14 (MGGKQRDEDDEAYG; SEQ ID NO: 71) of the 24P4C12 protein sequence. This peptide was coupled to Keyhole limpet hemacyanin (KLH) and was used to immunize a rabbit as follows. The rabbit was initially immunized with 200 μg of peptide-KLH mixed in complete Freund's adjuvant. The rabbit was then injected every two weeks with 200

μg of peptide-KLH in incomplete Freund's adjuvant. Bleeds were taken approximately 7-10 days following each immunization. ELISA and Western blotting analyses were used to determine titer and specificity of the rabbit serum to the immunizing peptide and 24P4C12 protein respectively. Affinity purified anti-24P4C12 polyclonal antibodies were prepared by passage of crude serum from immunized rabbit over an affinity matrix comprised of 24P4C12 peptide covalently coupled to Affigel 15 (BioRad). After extensive washing of the matrix with PBS, antibodies specific to 24P4C12 peptide were eluted with low pH glycine buffer (0.1M, pH 2.5) and dialyzed against PBS.

Western blot analysis was then performed with anti-24P4C12 pAb of 293T cells transiently transfected with 24P4C12 cDNA either in the CMV-driven PCDNA3.1 Myc-His (Invitrogen) or retroviral pSR-alpha expression vectors. 293T cells were transiently transfected with 10 μg of either empty vector, or with the 24P4C12 cDNA in pcDNA 3.1 CMV-driven MYC-His (Invitrogen) or pSR-alpha retroviral expression vectors using the CaPO4 method. Forty hours following transfection cells were harvested and lysed in 2×SDS-PAGE sample buffer. Cell lysates in sample buffer were then subjected to either mild heat denaturation (70° C.) or strong heat denaturation (100° C.), separated on a 10% SDS-PAGE gel and transferred to nitrocellulose. Membranes were then subjected to Western analysis with 2 μg/ml of an affinity purified rabbit anti-peptide pAb raised to amino acids 1-14 (MGGKQRDEDDEAYG; SEQ ID NO: 71) of 24P4C12. Anti-24P4C12 immunoreactive bands were visualized by incubation with anti-rabbit-HRP conjugated secondary antibody and enhanced chemiluminescence detection.

Figure 10B:
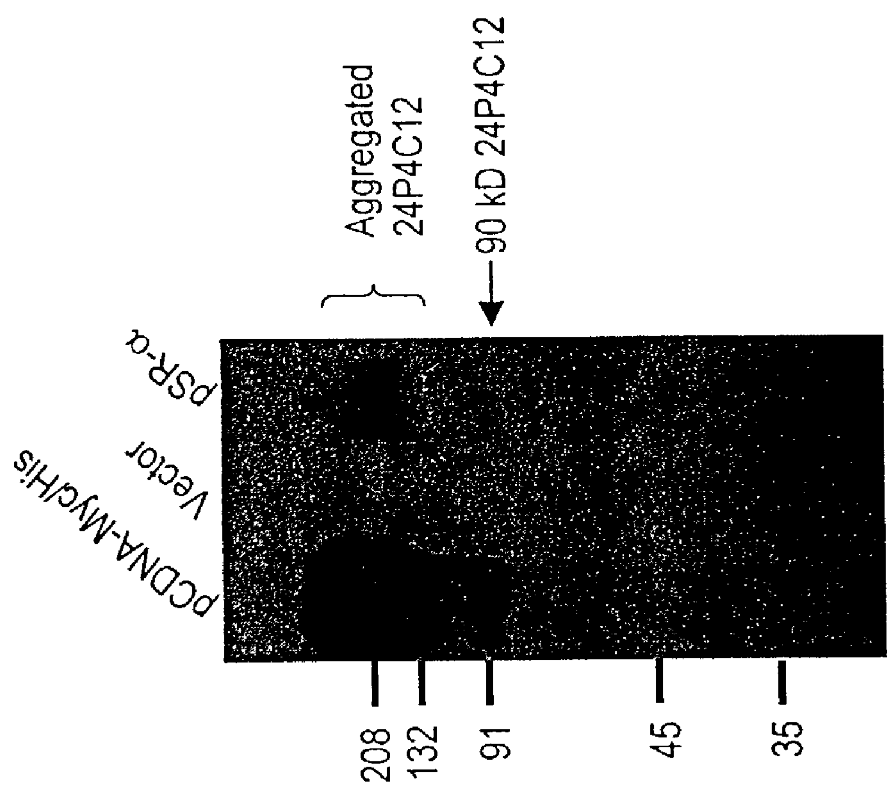
FIG. 10B. Detection of 24P4C12 protein in 293T cells transfected with 24P4C12 cDNA by 24P4C12-specific polyclonal antibodies. Transfected 293T cells prepared as for FIG. 10A were lysed in sample buffer and subjected to strong heat denaturation (100° C.). Western analysis with 2 μg/ml of an affinity purified rabbit anti-peptide pAb raised to amino acids 1-14 (MGGKQRDEDDEAYG) of 24P4C12 was performed as for FIG. 10A. Results show specific recognition of a 90 kD immunoreactive band (arrow) and a high molecular weight smear (>132 Kd) that is enhanced by heat denaturation.
Figure 10A:
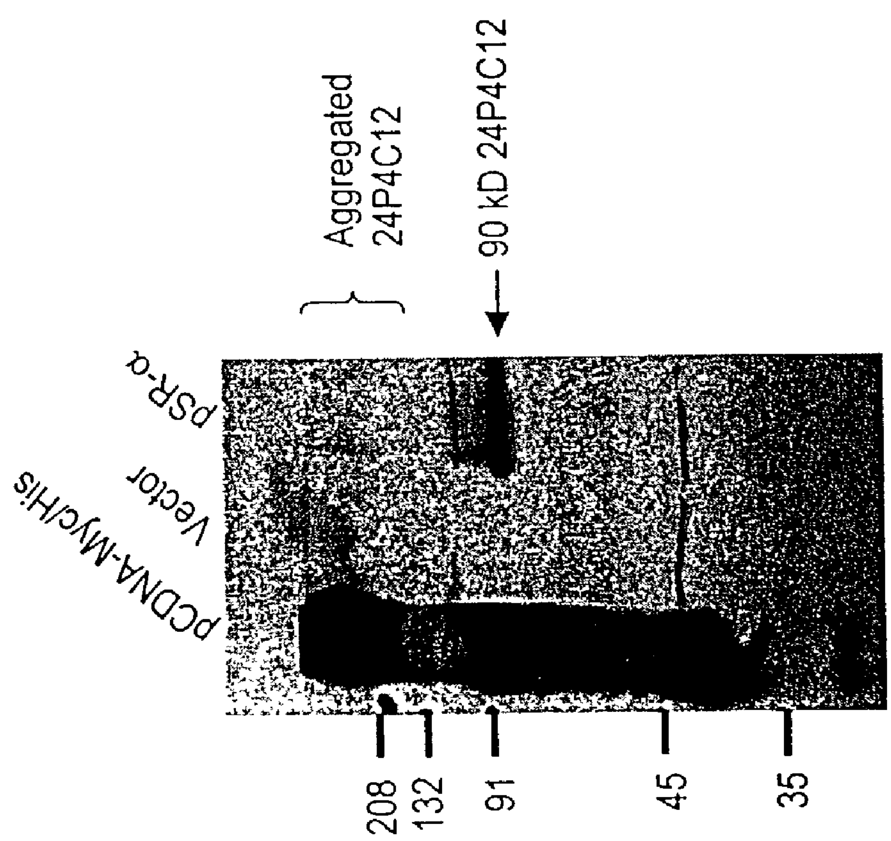
FIG. 10A. Detection of 24P4C12 protein in 293T cells transfected with 24P4C12 cDNA by 24P4C12-specific polyclonal antibodies. 293T cells were transiently transfected with empty vector, or 24P4C12 cDNA in pcDNA 3.1 CMV-driven MYC-His or pSR-alpha retroviral expression vectors. Cell lysates in sample buffer were then subjected to mild heat denaturation (70° C.) and separated on a 10% SDS-PAGE gel and transferred to nitrocellulose. Membranes were then subjected to western analysis with 2 μg/ml of an affinity purified rabbit anti-peptide pAb raised to amino acids 1-14 (MGGKQRDEDDEAYG) of 24P4C12. Anti-24P4C12 immunoreactive bands were visualized by incubation with anti-rabbit-HRP conjugated secondary antibody and enhanced chemiluminescence detection. Results show specific recognition of a 90 kD immunoreactive band (arrow) and a high molecular weight smear (>132 Kd) that is enhanced by heat denaturation.

Results of the western blot analysis show specific recognition of a 90 kD band and of a high molecular smear in transfected cells but not in cells transfected with empty vector (FIG. 10A, FIG. 10B). The calculated molecular weight of 24P4C12 from the amino acid sequence is 79.2 kD. The appearance of a 90 kD band in western analysis of cell lysates suggests that 24P4C12 protein contains post-translational modifications. Indeed, there are multiple potential N-linked glycosylation sites predicted from the amino acid sequence. The ratio of the high molecular smear is enhanced by high heat (100° C.) denaturation compared to mild heat (70° C.) denaturation which suggests aggregation of this 12 transmembrane protein upon heat-induced exposure of hydrophobic sequences. Multiple lower molecular weight bands are also detected in cells transfected with the highly expressed pcDNA 3.1 vector that may represent degradation products.

Example 5

Production of Recombinant 24P4C12 in a Mammalian System

To express recombinant 24P4C12, the full length 24P4C12 cDNA can be cloned into an expression vector that provides a 6His tag at the carboxyl-terminus (pCDNA 3.1 myc-his, InVitrogen). The constructs can be transfected into 293T cells. Transfected 293T cell lysates can be probed with the anti-24P4C12 polyclonal serum described in Example 4 above in a Western blot.

The 24P4C12 genes can also be subcloned into the retroviral expression vector pSRαMSVtkneo and used to establish 24P4C12 expressing cell lines as follows. The 24P4C12 coding sequence (from translation initiation ATG to the termination codons) is amplified by PCR using ds cDNA template from 24P4C12 cDNA. The PCR product is subcloned into pSRαMSVtkneo via the EcoR1(blunt-ended) and Xba 1 restriction sites on the vector and transformed into DH5α competent cells. Colonies are picked to screen for clones with unique internal restriction sites on the cDNA. The positive clone is confirmed by sequencing of the cDNA insert. Retroviruses may thereafter be used for infection and generation of various cell lines using, for example, NIH 3T3, PC3, and LnCap cells.

Example 6

Production of Recombinant 24P4C12 in a Baculovirus System

To generate a recombinant 24P4C12 protein in a baculovirus expression system, the 24P4C12 cDNA is cloned into the baculovirus transfer vector pBlueBac 4.5 (Invitrogen), which provides a His-tag at the N-terminus Specifically, pBlueBac-24P4C12 is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 24P4C12 protein is then generated by infection of HighFive insect cells (InVitrogen) with the purified baculovirus. Recombinant 24P4C12 protein may be detected using anti-24P4C12 antibody. 24P4C12 protein may be purified and used in various cell based assays or as immunogen to generate polyclonal and monoclonal antibodies specific for 24P4C12.

Example 7

Identification & Cloning of H38087, Family Member of 24P4C12

Figure 9A:
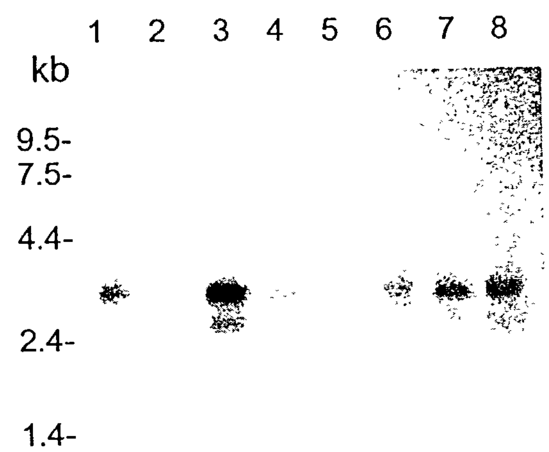
FIG. 9A. Expression of 24P4C12 in human tissues. A multiple tissue northern blot (Clontech) with 2 μg of mRNA/lane was probed with the 24P4C12 SSH fragment. Size standards in kilobases (kb) are indicated on the side. Lanes represent the following tissues: (1) heart; (2) brain; (3) placenta; (4) lung; (5) liver; (6) skeletal muscle; (7) kidney; and (8) pancreas.
Figure 9B:
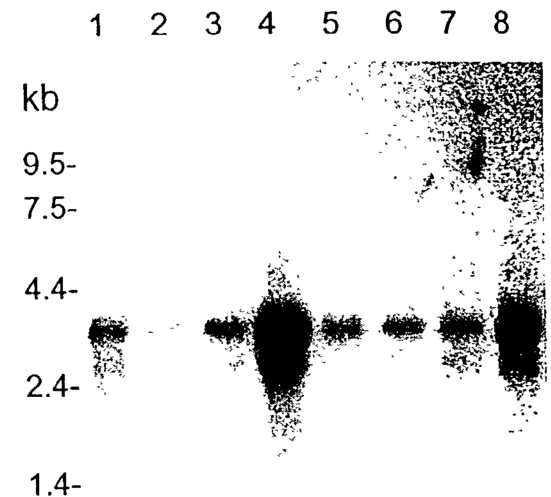
FIG. 9B. Expression of 24P4C12 in human tissues. A multiple tissue northern blot (Clontech) with 2 μg of mRNA/lane was probed with the 24P4C12 SSH fragment. Size standards in kilobases (kb) are indicated on the side. Lanes represent the following tissues: (1) spleen; (2) thymus; (3) prostate; (4) testis; (5) ovary; (6) small intestine; (7) colon; and (8) leukocytes.
Figure 9C:
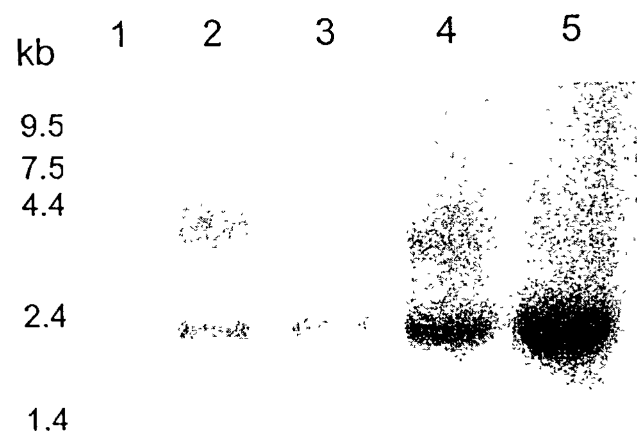
FIG. 9C. Expression of 24P4C12 in human tissues. An LAPC xenograft northern blot with 10 μg of total RNA/lane was probed with the 24P4C12 SSH fragment. Size standards in kilobases (kb) are indicated on the side. Lanes represent the following tissues: (1) PC-3; (2) LAPC-4 AD; (3) LAPC-4 AI; (4) LAPC-9 AD; (5) LAPC-9 AI.

H38087 was identified as a family member of 24P4C12 by searching the dBEST database with the 24P4C12 amino acid sequence using the tblastn tool in NCBI. ESTs that encode protein fragments of homologous proteins were identified. One of these, H38087, was cloned from a testis library. The cDNA (clone GTB6) is 2738 bp in size and encodes a 704 amino acid protein with 11 putative transmembrane domains (FIGS. 7A-7D; SEQ ID NOS: 6, 7). The 58 base pairs of 5' untranslated region are very GC rich (87%), indicating that this gene may contain translational regulatory elements (FIGS. 7A-7D). The amino acid sequence of 24P4C12 (SEQ ID NO: 2) and H38087 (SEQ ID NO: 7) are 44% identical and 56% homologous over the entire sequence (FIG. 8). Expression analysis shows that H38087 is ubiquitously expressed (FIG. 9). Highest expression levels are detected in testis. Expression is also seen in all the LAPC xenografts. Since H38087 is ubiquitously expressed, it could serve as a control for testing 24P4C12-specific therapeutics. A 24P4C12-specific therapeutic that affects H38087 function could be toxic to normal cells. However, a therapeutic that selectively affects 24P4C12, but not H38087, may be less toxic to normal cells. Therefore, H38087 protein is useful as a pre-clinical testing tool for therapeutic modalities directed towards 24P4C12.

Example 8

Identification of Potential Signal Transduction Pathways

To determine whether 24P4C12 directly or indirectly activates known signal transduction pathways in cells, luciferase (luc) based transcriptional reporter assays are carried out in cells expressing 24P4C12. These transcriptional reporters contain consensus binding sites for known transcription factors that lie downstream of well characterized signal transduction pathways. The reporters and examples of their associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress 24P4C12-mediated effects may be assayed in cells showing mRNA expression. Luciferase reporter plasmids may be introduced by lipid mediated transfection (TFX-50, Promega). Luciferase activity, an indicator of relative transcriptional activity, is measured by incubation of cells extracts with luciferin substrate and luminescence of the reaction is monitored in a luminometer.

Example 9

Generation of 24P4C12 Monoclonal Antibodies

In order to generate 24P4C12 monoclonal antibodies, a glutathione-S-transferase (GST) fusion protein encompassing a 24P4C12 protein is synthesized and used as immunogen. Alternatively, 24P4C12 can be conveniently expressed in 293T cells transfected with a CMV-driven expression vector encoding 24P4C12 with a C-terminal 6×His and MYC tag (pcDNA3.1/mycHIS, Invitrogen). HIS-tagged 24P4C12 expressed in cells can be purified using a nickel column using standard techniques.

Balb C mice are initially immunized intraperitoneally with 200 μg of the GST-24P4C12 fusion protein mixed in complete Freund's adjuvant. Mice are subsequently immunized every 2 weeks with 75 μg of GST-24P4C12 protein mixed in Freund's incomplete adjuvant for a total of 3 immunizations. Reactivity of serum from immunized mice to full length 24P4C12 protein is monitored by ELISA using a partially purified preparation of HIS-tagged 24P4C12 protein expressed from 293T cells (Example 5). Mice showing the strongest reactivity are rested for 3 weeks and given a final injection of fusion protein in PBS and then sacrificed 4 days later. The spleens of the sacrificed mice are then harvested and fused to SPO/2 myeloma cells using standard procedures (Harlow and Lane, 1988). Supernatants from growth wells following HAT selection are screened by ELISA and Western blot to identify 24P4C12 specific antibody producing clones.

The binding affinity of a 24P4C12 monoclonal antibody may be determined using standard technology. Affinity measurements quantify the strength of antibody to epitope binding and may be used to help define which 24P4C12 monoclonal antibodies are preferred for diagnostic or therapeutic use. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 10

In Vitro Assays of 24P4C12 Function

The expression of 24P4C12 in prostate and other cancers provides evidence that this gene has a functional role in tumor progression and/or tumor initiation. It is possible that 24P4C12 functions as a receptor involved in activating proliferation signals. 24P4C12 function can be assessed in mammalian cells using in vitro approaches. For mammalian expression, 24P4C12 can be cloned into a number of appropriate vectors, including pcDNA 3.1 myc-His-tag Example 5) and the retroviral vector pSRαtkneo (Muller et al., 1991, MCB 11:1785). Using such expression vectors, 24P4C12 can be expressed in several cell lines, including PC-3, NIH 3T3, LNCaP and 293T. Expression of 24P4C12 can be monitored using anti-24P4C12 antibodies and northern blot analysis (see Examples 4 and 9).

Mammalian cell lines expressing 24P4C12 can be tested in several in vitro and in vivo assays, including cell proliferation in tissue culture, activation of apoptotic signals, tumor formation in SCID mice, and in vitro invasion using a membrane invasion culture system (MICS; Welch et al., Int. J. Cancer 43: 449-457). 24P4C12 cell phenotype is compared to the phenotype of cells that lack expression of 24P4C12.

Cell lines expressing 24P4C12 can also be assayed for alteration of invasive and migratory properties by measuring passage of cells through a matrigel coated porous membrane chamber (Becton Dickinson). Passage of cells through the membrane to the opposite side is monitored using a fluorescent assay (Becton Dickinson Technical Bulletin #428) using calcein-Am (Molecular Probes) loaded indicator cells. Cell lines analyzed include parental and 24P4C12 overexpressing PC3, NIH 3T3 and LNCaP cells. To determine whether 24P4C12-expressing cells have chemoattractant properties, indicator cells are monitored for passage through the porous membrane toward a gradient of 24P4C12 conditioned media compared to control media. This assay may also be used to qualify and quantify specific neutralization of the 24P4C12 induced effect by candidate cancer therapeutic compositions.

The function of 24P4C12 can be evaluated using anti-sense RNA technology coupled to the various functional assays described above, e.g. growth, invasion and migration. Anti-sense RNA oligonucleotides can be introduced into 24P4C12 expressing cells, thereby preventing the expression of 24P4C12. Control and anti-sense containing cells can be analyzed for proliferation, invasion, migration, apoptotic and transcriptional potential. The local as well as systemic effect of the loss of 24P4C12 expression can be evaluated.

Example 11

In Vivo Assay for 24P4C12 Tumor Growth Promotion

The effect of the 24P4C12 protein on tumor cell growth may be evaluated in vivo by gene overexpression in tumor-bearing mice. For example, SCID mice can be injected subcutaneously on each flank with $1\times10^6$ of either PC3, TSUPR1, or DU145 cells containing tkNeo empty vector or 24P4C12. At least two strategies may be used: (1) Constitutive 24P4C12 expression under regulation of a promoter such as a constitutive promoter obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems, and (2) Regulated expression under control of an inducible vector system, such as ecdysone, tet, etc., provided such promoters are compatible with the host cell systems. Tumor volume is then monitored at the appearance of palpable tumors and followed over time to determine if 24P4C12 expressing cells grow at a faster rate and whether tumors produced by 24P4C12-expressing cells demonstrate characteristics of altered aggressiveness (e.g. enhanced metastasis, vascularization, reduced responsiveness to chemotherapeutic drugs). Additionally, mice may be implanted with $1\times10^5$ of the same cells orthotopically to determine if 24P4C12 has an effect on local growth in the prostate or on the ability of the cells to metastasize, specifically to lungs, lymph nodes, and bone marrow.

The assay is also useful to determine the 24P4C12 inhibitory effect of candidate therapeutic compositions, such as for example, 24P4C12 intrabodies, 24P4C12 antisense molecules and ribozymes.

Example 12

Western Analysis of 24P4C12 Expression in Subcellular Fractions

Sequence analysis of 24P4C12 revealed the presence of a transmembrane domain. The cellular location of 24P4C12 can be assessed using subcellular fractionation techniques widely used in cellular biology (Storrie B, et al. Methods Enzymol. 1990;182:203-25). Prostate cell lines can be separated into nuclear, cytosolic and membrane fractions. The expression of 24P4C12 in the different fractions can be tested using western blotting techniques.

Alternatively, to determine the subcellular localization of 24P4C12, 293T cells can be transfected with an expression vector encoding HIS-tagged 24P4C12 (PCDNA 3.1 MYC/HIS, Invitrogen). The transfected cells can be harvested and subjected to a differential subcellular fractionation protocol as previously described (Pemberton, P. A. et al, 1997, J of Histochemistry and Cytochemistry, 45:1697-1706.) This protocol separates the cell into fractions enriched for nuclei, heavy membranes (lysosomes, peroxisomes, and mitochondria), light membranes (plasma membrane and endoplasmic reticulum), and soluble proteins.

Throughout this application, various publications are referenced within parentheses. The disclosures of these publications are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention. These modifications and other embodiments include, but are not limited to, adapting the various methods, assays, molecules and strategies disclosed herein in connection with 24P4C12 for use with H38087.

The invention claimed is:

1. A method of inhibiting growth or survival of cancer cells that express 24P4C12 protein having an amino acid sequence of SEQ ID NO: 2, the method comprising steps of:

providing to the cells a composition comprising at least one component that interacts with 24P4C12 protein, whereby the growth, survival, or growth and survival of cancer cells that express 24P4C12 is inhibited;

wherein said component is at least an antigen-binding portion of an antibody that specifically binds to the extracellular portion of 24P4C12 protein.

2. The method of claim 1, wherein the antibody portion is an entire antibody.

3. The method claim 1, wherein the cancer cells are prostate cancer cells.

4. The method of claim 2, wherein the cancer cells are prostate cancer cells.

5. The method of claim 1, wherein the antibody is a monoclonal antibody.

6. The method of claim 1, wherein the antibody portion is an Fab, $F(ab')_2$, Fv or $F_{s_v}$ fragment.

7. The method of claim 1, wherein the antibody is conjugated to a toxin or to a therapeutic agent.

8. The method of claim 1, wherein the antibody is a humanized or fully human antibody.

* * * * *

SEQUENCE LISTING

```
<160> NUMBER OF SEQ ID NOS: 71

<210> SEQ ID NO 1
<211> LENGTH: 2585
<212> TYPE: DNA
<213> ORGANISM: Homo sapiens
<220> FEATURE:
<221> NAME/KEY: CDS
<222> LOCATION: (4)...(2136)

<400> SEQUENCE: 1

gcc atg ggg gga aag cag cgg gac gag gat gac gag gcc tac ggg aag       48
    Met Gly Gly Lys Gln Arg Asp Glu Asp Asp Glu Ala Tyr Gly Lys
     1               5                  10                  15

cca gtc aaa tac gac ccc tcc ttt cga ggc ccc atc aag aac aga agc       96
Pro Val Lys Tyr Asp Pro Ser Phe Arg Gly Pro Ile Lys Asn Arg Ser
                20                  25                  30

tgc aca gat gtc atc tgc tgc gtc ctc ttc ctg ctc ttc att cta ggt      144
Cys Thr Asp Val Ile Cys Cys Val Leu Phe Leu Leu Phe Ile Leu Gly
            35                  40                  45

tac atc gtg gtg ggg att gtg gcc tgg ttg tat gga gac ccc cgg caa      192
Tyr Ile Val Val Gly Ile Val Ala Trp Leu Tyr Gly Asp Pro Arg Gln
        50                  55                  60

gtc ctc tac ccc agg aac tct act ggg gcc tac tgt ggc atg ggg gag      240
```

-continued

```
Val Leu Tyr Pro Arg Asn Ser Thr Gly Ala Tyr Cys Gly Met Gly Glu
     65                  70                  75

aac aaa gat aag ccg tat ctc ctg tac ttc aac atc ttc agc tgc atc      288
Asn Lys Asp Lys Pro Tyr Leu Leu Tyr Phe Asn Ile Phe Ser Cys Ile
 80                  85                  90                  95

ctg tcc agc aac atc atc tca gtt gct gag aac ggc cta cag tgc ccc      336
Leu Ser Ser Asn Ile Ile Ser Val Ala Glu Asn Gly Leu Gln Cys Pro
                100                 105                 110

aca ccc cag gtg tgt gtg tcc tcc tgc ccg gag gac cca tgg act gtg      384
Thr Pro Gln Val Cys Val Ser Ser Cys Pro Glu Asp Pro Trp Thr Val
            115                 120                 125

gga aaa aac gag ttc tca cag act gtt ggg gaa gtc ttc tat aca aaa      432
Gly Lys Asn Glu Phe Ser Gln Thr Val Gly Glu Val Phe Tyr Thr Lys
        130                 135                 140

aac agg aac ttt tgt ctg cca ggg gta ccc tgg aat atg acg gtg atc      480
Asn Arg Asn Phe Cys Leu Pro Gly Val Pro Trp Asn Met Thr Val Ile
    145                 150                 155

aca agc ctg caa cag gaa ctc tgc ccc agt ttc ctc ctc ccc tct gct      528
Thr Ser Leu Gln Gln Glu Leu Cys Pro Ser Phe Leu Leu Pro Ser Ala
160                 165                 170                 175

cca gct ctg ggg cgc tgc ttt cca tgg acc aac gtt act cca ccg gcg      576
Pro Ala Leu Gly Arg Cys Phe Pro Trp Thr Asn Val Thr Pro Pro Ala
                180                 185                 190

ctc cca ggg atc acc aat gac acc acc ata cag cag ggg atc agc ggt      624
Leu Pro Gly Ile Thr Asn Asp Thr Thr Ile Gln Gln Gly Ile Ser Gly
            195                 200                 205

ctt att gac agc ctc aat gcc cga gac atc agt gtt aag atc ttt gaa      672
Leu Ile Asp Ser Leu Asn Ala Arg Asp Ile Ser Val Lys Ile Phe Glu
        210                 215                 220

gat ttt gcc cag tcc tgg tat tgg att ctt gtt gcc ctg ggg gtg gct      720
Asp Phe Ala Gln Ser Trp Tyr Trp Ile Leu Val Ala Leu Gly Val Ala
    225                 230                 235

ctg gtc ttg agc cta ctg ttt atc ttg ctt ctg cgc ctg gtg gct ggg      768
Leu Val Leu Ser Leu Leu Phe Ile Leu Leu Leu Arg Leu Val Ala Gly
240                 245                 250                 255

ccc ctg gtg ctg gtg ctg atc ctg gga gtg ctg ggc gtg ctg gca tac      816
Pro Leu Val Leu Val Leu Ile Leu Gly Val Leu Gly Val Leu Ala Tyr
                260                 265                 270

ggc atc tac tac tgc tgg gag gag tac cga gtg ctg cgg gac aag ggc      864
Gly Ile Tyr Tyr Cys Trp Glu Glu Tyr Arg Val Leu Arg Asp Lys Gly
            275                 280                 285

gcc tcc atc tcc cag ctg ggt ttc acc acc aac ctc agt gcc tac cag      912
Ala Ser Ile Ser Gln Leu Gly Phe Thr Thr Asn Leu Ser Ala Tyr Gln
        290                 295                 300

agc gtg cag gag acc tgg ctg gcc gcc ctg atc gtg ttg gcg gtg ctt      960
Ser Val Gln Glu Thr Trp Leu Ala Ala Leu Ile Val Leu Ala Val Leu
    305                 310                 315

gaa gcc atc ctg ctg ctg atg ctc atc ttc ctg cgg cag cgg att cgt     1008
Glu Ala Ile Leu Leu Leu Met Leu Ile Phe Leu Arg Gln Arg Ile Arg
320                 325                 330                 335

att gcc atc gcc ctc ctg aag gag gcc agc aag gct gtg gga cag atg     1056
Ile Ala Ile Ala Leu Leu Lys Glu Ala Ser Lys Ala Val Gly Gln Met
                340                 345                 350

atg tct acc atg ttc tac cca ctg gtc acc ttt gtc ctc ctc ctc atc     1104
Met Ser Thr Met Phe Tyr Pro Leu Val Thr Phe Val Leu Leu Leu Ile
            355                 360                 365

tgc att gcc tac tgg gcc atg act gct ctg tac ctg gct aca tcg ggg     1152
Cys Ile Ala Tyr Trp Ala Met Thr Ala Leu Tyr Leu Ala Thr Ser Gly
        370                 375                 380
```

-continued

```
caa ccc cag tat gtg ctc tgg gca tcc aac atc agc tcc ccc ggc tgt      1200
Gln Pro Gln Tyr Val Leu Trp Ala Ser Asn Ile Ser Ser Pro Gly Cys
    385                 390                 395

gag aaa gtg cca ata aat aca tca tgc aac ccc acg gcc cac ctt gtg      1248
Glu Lys Val Pro Ile Asn Thr Ser Cys Asn Pro Thr Ala His Leu Val
400                 405                 410                 415

aac tcc tcg tgc cca ggg ctg atg tgc gtc ttc cag ggc tac tca tcc      1296
Asn Ser Ser Cys Pro Gly Leu Met Cys Val Phe Gln Gly Tyr Ser Ser
                420                 425                 430

aaa ggc cta atc caa cgt tct gtc ttc aat ctg caa atc tat ggg gtc      1344
Lys Gly Leu Ile Gln Arg Ser Val Phe Asn Leu Gln Ile Tyr Gly Val
            435                 440                 445

ctg ggg ctc ttc tgg acc ctt aac tgg gta ctg gcc ctg ggc caa tgc      1392
Leu Gly Leu Phe Trp Thr Leu Asn Trp Val Leu Ala Leu Gly Gln Cys
        450                 455                 460

gtc ctc gct gga gcc ttt gcc tcc ttc tac tgg gcc ttc cac aag ccc      1440
Val Leu Ala Gly Ala Phe Ala Ser Phe Tyr Trp Ala Phe His Lys Pro
    465                 470                 475

cag gac atc cct acc ttc ccc tta atc tct gcc ttc atc cgc aca ctc      1488
Gln Asp Ile Pro Thr Phe Pro Leu Ile Ser Ala Phe Ile Arg Thr Leu
480                 485                 490                 495

cgt tac cac act ggg tca ttg gca ttt gga gcc ctc atc ctg acc ctt      1536
Arg Tyr His Thr Gly Ser Leu Ala Phe Gly Ala Leu Ile Leu Thr Leu
                500                 505                 510

gtg cag ata gcc cgg gtc atc ttg gag tat att gac cac aag ctc aga      1584
Val Gln Ile Ala Arg Val Ile Leu Glu Tyr Ile Asp His Lys Leu Arg
            515                 520                 525

gga gtg cag aac cct gta gcc cgc tgc atc atg tgc tgt ttc aag tgc      1632
Gly Val Gln Asn Pro Val Ala Arg Cys Ile Met Cys Cys Phe Lys Cys
        530                 535                 540

tgc ctc tgg tgt ctg gaa aaa ttt atc aag ttc cta aac cgc aat gca      1680
Cys Leu Trp Cys Leu Glu Lys Phe Ile Lys Phe Leu Asn Arg Asn Ala
    545                 550                 555

tac atc atg atc gcc atc tac ggg aag aat ttc tgt gtc tca gcc aaa      1728
Tyr Ile Met Ile Ala Ile Tyr Gly Lys Asn Phe Cys Val Ser Ala Lys
560                 565                 570                 575

aat gcg ttc atg cta ctc atg cga aac att gtc agg gtg gtc gtc ctg      1776
Asn Ala Phe Met Leu Leu Met Arg Asn Ile Val Arg Val Val Val Leu
                580                 585                 590

gac aaa gtc aca gac ctg ctg ctg ttc ttt ggg aag ctg ctg gtg gtc      1824
Asp Lys Val Thr Asp Leu Leu Leu Phe Phe Gly Lys Leu Leu Val Val
            595                 600                 605

gga ggc gtg ggg gtc ctg tcc ttc ttt ttt ttc tcc ggt cgc atc ccg      1872
Gly Gly Val Gly Val Leu Ser Phe Phe Phe Phe Ser Gly Arg Ile Pro
        610                 615                 620

ggg ctg ggt aaa gac ttt aag agc ccc cac ctc aac tat tac tgg ctg      1920
Gly Leu Gly Lys Asp Phe Lys Ser Pro His Leu Asn Tyr Tyr Trp Leu
    625                 630                 635

ccc atc atg acc tcc atc ctg ggg gcc tat gtc atc gcc agc ggc ttc      1968
Pro Ile Met Thr Ser Ile Leu Gly Ala Tyr Val Ile Ala Ser Gly Phe
640                 645                 650                 655

ttc agc gtt ttc ggc atg tgt gtg gac acg ctc ttc ctc tgc ttc ctg      2016
Phe Ser Val Phe Gly Met Cys Val Asp Thr Leu Phe Leu Cys Phe Leu
                660                 665                 670

gaa gac ctg gag cgg aac aac ggc tcc ctg gac cgg ccc tac tac atg      2064
Glu Asp Leu Glu Arg Asn Asn Gly Ser Leu Asp Arg Pro Tyr Tyr Met
            675                 680                 685

tcc aag agc ctt cta aag att ctg ggc aag aag aac gag gcg ccc ccg      2112
Ser Lys Ser Leu Leu Lys Ile Leu Gly Lys Lys Asn Glu Ala Pro Pro
        690                 695                 700
```

```
gac aac aag aag agg aag aag tga cagctccggc cctgatccag gactgcaccc    2166
Asp Asn Lys Lys Arg Lys Lys  *
    705                 710

cacccccacc gtccagccat ccaacctcac ttcgccttac aggtctccat tttgtggtaa   2226

aaaaaggttt taggccaggc gccgtggctc acgcctgtaa tccaacactt tgagaggctg   2286

aggcgggcgg atcacctgag tcaggagttc gagaccagcc tggccaacat ggtgaaacct   2346

ccgtctctat taaaaataca aaaattagcc gagagtggtg gcatgcacct gtcatcccag   2406

ctactcggga ggctgaggca ggagaatcgc ttgaacccgg gaggcagagg ttgcagtgag   2466

ccgagatcgc gccactgcac tccaacctgg gtgacagact ctgtctccaa aacaaaacaa   2526

acaaacaaaa agattttatt aaagatattt tgttaactca gtaaaaaaaa aaaaaaaaa    2585


<210> SEQ ID NO 2
<211> LENGTH: 710
<212> TYPE: PRT
<213> ORGANISM: Homo sapiens

<400> SEQUENCE: 2

Met Gly Gly Lys Gln Arg Asp Glu Asp Asp Glu Ala Tyr Gly Lys Pro
 1               5                  10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
        35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
    130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
    210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Leu Arg Leu Val Ala Gly Pro
                245                 250                 255

Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
```

-continued

```
        275                 280                 285

Ser Ile Ser Gln Leu Gly Phe Thr Thr Asn Leu Ser Ala Tyr Gln Ser
    290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                325                 330                 335

Ala Ile Ala Leu Leu Lys Glu Ala Ser Lys Ala Val Gly Gln Met Met
            340                 345                 350

Ser Thr Met Phe Tyr Pro Leu Val Thr Phe Val Leu Leu Leu Ile Cys
        355                 360                 365

Ile Ala Tyr Trp Ala Met Thr Ala Leu Tyr Leu Ala Thr Ser Gly Gln
    370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
            420                 425                 430

Gly Leu Ile Gln Arg Ser Val Phe Asn Leu Gln Ile Tyr Gly Val Leu
        435                 440                 445

Gly Leu Phe Trp Thr Leu Asn Trp Val Leu Ala Leu Gly Gln Cys Val
    450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
            500                 505                 510

Gln Ile Ala Arg Val Ile Leu Glu Tyr Ile Asp His Lys Leu Arg Gly
        515                 520                 525

Val Gln Asn Pro Val Ala Arg Cys Ile Met Cys Cys Phe Lys Cys Cys
    530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Val Leu Asp
            580                 585                 590

Lys Val Thr Asp Leu Leu Leu Phe Phe Gly Lys Leu Leu Val Val Gly
        595                 600                 605

Gly Val Gly Val Leu Ser Phe Phe Phe Phe Ser Gly Arg Ile Pro Gly
    610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
            660                 665                 670

Asp Leu Glu Arg Asn Asn Gly Ser Leu Asp Arg Pro Tyr Tyr Met Ser
        675                 680                 685

Lys Ser Leu Leu Lys Ile Leu Gly Lys Lys Asn Glu Ala Pro Pro Asp
    690                 695                 700
```

```
Asn Lys Lys Arg Lys Lys
705                 710


<210> SEQ ID NO 3
<211> LENGTH: 160
<212> TYPE: DNA
<213> ORGANISM: Homo sapiens
<220> FEATURE:
<221> NAME/KEY: CDS
<222> LOCATION: (1)...(160)

<400> SEQUENCE: 3

gat cag ggc ggc cag cca ggt ctc ctg cac gct ctg gta ggc act gag       48
Asp Gln Gly Gly Gln Pro Gly Leu Leu His Ala Leu Val Gly Thr Glu
 1               5                  10                  15

gtt ggt ggt gaa acc cag ctg gga gat gga ggc gcc ctc gtc ccg cag       96
Val Gly Gly Glu Thr Gln Leu Gly Asp Gly Gly Ala Leu Val Pro Gln
             20                  25                  30

cac tcg gta ctc ctc cca gca gta gta gat gcc ata tgc cag cac gcc      144
His Ser Val Leu Leu Pro Ala Val Val Asp Ala Ile Cys Gln His Ala
         35                  40                  45

cag cac tcc cag gat c                                                160
Gln His Ser Gln Asp
     50


<210> SEQ ID NO 4
<211> LENGTH: 53
<212> TYPE: PRT
<213> ORGANISM: Homo sapiens

<400> SEQUENCE: 4

Asp Gln Gly Gly Gln Pro Gly Leu Leu His Ala Leu Val Gly Thr Glu
 1               5                  10                  15

Val Gly Gly Glu Thr Gln Leu Gly Asp Gly Gly Ala Leu Val Pro Gln
             20                  25                  30

His Ser Val Leu Leu Pro Ala Val Val Asp Ala Ile Cys Gln His Ala
         35                  40                  45

Gln His Ser Gln Asp
     50


<210> SEQ ID NO 5
<211> LENGTH: 705
<212> TYPE: PRT
<213> ORGANISM: Mouse

<400> SEQUENCE: 5

Arg Lys Gln Asn Glu Asn Glu Ala His Gly Asn Ser Ala Lys Tyr Asp
 1               5                  10                  15

Pro Ser Phe Arg Gly Pro Ile Lys Asn Arg Gly Cys Thr Asp Ile Ile
             20                  25                  30

Cys Cys Val Leu Phe Leu Ile Phe Ile Leu Gly Tyr Ile Ile Val Gly
         35                  40                  45

Leu Val Ala Trp Val Tyr Gly Asp Pro Arg Gln Val Leu Tyr Pro Arg
     50                  55                  60

Asn Ser Thr Gly Ala Tyr Cys Gly Val Gly Asp Asn Lys Asp Lys Pro
65                  70                  75                  80

Tyr Val Leu Tyr Phe Asp Ile Leu Ser Cys Ala Ala Ala Ile Asn Ile
                85                  90                  95

Ile Ser Ile Ala Glu Asn Gly Leu Gln Cys Pro Thr Pro Gln Val Cys
            100                 105                 110
```

-continued

```
Val Ser Ser Cys Pro Leu Ala Pro Trp Ala Val Glu Val Phe Gln Phe
        115                 120                 125

Ser Lys Thr Val Gly Glu Val Tyr Gly Glu Arg Arg Asn Phe Cys Leu
    130                 135                 140

Pro Ala Val Ser Pro Asp Met Ile Val Glu Glu Ser Leu Gln Lys Gly
145                 150                 155                 160

Leu Cys Pro Arg Phe Leu Leu Pro Ser Thr Pro Ala Leu Gly Arg Cys
                165                 170                 175

Phe Pro Leu Pro Asn Ile Asn Phe Thr Leu Pro Glu Asp Leu Arg Ile
            180                 185                 190

Asn Asn Thr Thr Val Ser Asn Gly Ile Ser Gly Leu Leu Asp Ser Ile
        195                 200                 205

Asn Ala Arg Asp Val Ser Val Lys Ile Phe Glu Asp Phe Ala Gln Ser
    210                 215                 220

Trp Tyr Trp Ile Leu Val Ala Leu Gly Val Ala Leu Ala Leu Ser Leu
225                 230                 235                 240

Leu Phe Ile Leu Leu Leu Arg Leu Val Ala Ala Pro Leu Val Leu Leu
                245                 250                 255

Leu Ile Val Gly Val Leu Ala Val Leu Ala Tyr Gly Ile Tyr His Cys
            260                 265                 270

Trp Gln Gln Tyr Gln Val Phe Arg Asp Lys Gly Ala Ser Ile Thr Gln
        275                 280                 285

Leu Gly Phe Thr Thr Asn Phe Ser Ala Tyr Gln Ser Val Lys Glu Thr
    290                 295                 300

Trp Leu Ala Ala Leu Ile Val Leu Ala Val Leu Glu Gly Ile Leu Leu
305                 310                 315                 320

Leu Met Leu Ile Phe Leu Arg Gln Arg Ile Arg Ile Ala Ile Ala Leu
                325                 330                 335

Leu Lys Glu Ala Ser Arg Ala Val Gly Gln Met Met Ser Thr Met Phe
            340                 345                 350

Tyr Pro Leu Val Thr Phe Val Leu Leu Val Ile Cys Ile Gly Tyr Trp
        355                 360                 365

Ala Val Thr Ala Leu Tyr Leu Ala Thr Ser Gly Gln Pro Gln Tyr Ile
    370                 375                 380

Tyr Trp Ala Ser Asn Thr Ser Thr Pro Gly Cys Glu Asn Val Pro Val
385                 390                 395                 400

Asn Met Thr Cys Asp Pro Met Ala Pro Leu Asn Ser Ser Cys Pro Asn
                405                 410                 415

Leu Lys Cys Val Phe Lys Gly Tyr Ser Thr Thr Gly Leu Ala Gln Arg
            420                 425                 430

Ser Leu Phe Asn Leu Gln Ile Tyr Gly Val Leu Gly Leu Phe Trp Thr
        435                 440                 445

Val Asn Trp Val Leu Ala Leu Gly Gln Cys Val Leu Ala Gly Ala Phe
    450                 455                 460

Ala Ser Phe Tyr Trp Ala Phe His Lys Pro Arg Asp Ile Pro Thr Phe
465                 470                 475                 480

Pro Leu Ser Ser Ala Phe Ile Arg Thr Leu Arg Tyr His Thr Gly Ser
                485                 490                 495

Leu Ala Phe Gly Ala Leu Ile Leu Ser Leu Val Gln Ile Ala Arg Val
            500                 505                 510

Ile Leu Glu Tyr Ile Asp His Lys Leu Arg Gly Ser Gln Asn Pro Val
        515                 520                 525
```

-continued

```
Ala Arg Cys Ile Ile Cys Cys Phe Lys Cys Cys Leu Trp Cys Leu Glu
    530                 535                 540

Lys Phe Ile Lys Phe Leu Asn Arg Asn Ala Tyr Ile Met Ile Ala Ile
545                 550                 555                 560

Tyr Gly Lys Asn Phe Cys Val Ser Ala Lys Asn Ala Phe Met Leu Leu
                565                 570                 575

Met Arg Asn Val Leu Arg Val Val Val Leu Asp Lys Val Thr Asp Leu
            580                 585                 590

Leu Leu Phe Phe Gly Lys Leu Leu Val Val Gly Gly Val Gly Val Leu
        595                 600                 605

Ser Phe Phe Phe Phe Ser Gly Arg Ile Lys Gly Leu Gly Lys Asp Phe
    610                 615                 620

Glu Asn Pro Asn Leu Asn Tyr Tyr Trp Leu Pro Ile Met Thr Ser Ile
625                 630                 635                 640

Met Gly Ala Tyr Val Ile Ala Ser Gly Phe Phe Ser Val Phe Gly Met
                645                 650                 655

Cys Val Asp Thr Leu Phe Leu Cys Phe Leu Glu Asp Leu Glu Arg Asn
            660                 665                 670

Asp Gly Ser Gln Glu Arg Pro Tyr Tyr Met Pro Lys Ala Leu Leu Lys
        675                 680                 685

Ile Leu Gly Lys Lys Asn Glu Ala Pro Thr Gly Gly Lys Thr Arg Lys
    690                 695                 700

Lys
705


<210> SEQ ID NO 6
<211> LENGTH: 2737
<212> TYPE: DNA
<213> ORGANISM: Homo sapiens
<220> FEATURE:
<221> NAME/KEY: CDS
<222> LOCATION: (58)...(2172)

<400> SEQUENCE: 6

gcccgcccgg gctggggtcg cgctggctcg gactccgctc cccgccccgc cgcggcc atg    60
                                                               Met
                                                                1

gag gac gag cgg aaa aac gga gcc tac gga acg cca cag aag tat gat      108
Glu Asp Glu Arg Lys Asn Gly Ala Tyr Gly Thr Pro Gln Lys Tyr Asp
            5                   10                  15

ccc act ttc aaa gga ccc att tac aat agg ggc tgc acg gat atc ata      156
Pro Thr Phe Lys Gly Pro Ile Tyr Asn Arg Gly Cys Thr Asp Ile Ile
        20                  25                  30

tgc tgt gtg ttc ctg ctc ctg gcc att gtg ggc tac gtg gct gta ggc      204
Cys Cys Val Phe Leu Leu Leu Ala Ile Val Gly Tyr Val Ala Val Gly
    35                  40                  45

atc ata gcc tgg act cat gga gac cct cga aag gtg atc tac ccc act      252
Ile Ile Ala Trp Thr His Gly Asp Pro Arg Lys Val Ile Tyr Pro Thr
 50                  55                  60                  65

gat agc cgg ggc gag ttc tgc ggg cag aag ggc aca aaa aac gag aac      300
Asp Ser Arg Gly Glu Phe Cys Gly Gln Lys Gly Thr Lys Asn Glu Asn
                70                  75                  80

aaa ccc tat ctg ttt tat ttc aac att gtg aaa tgt gcc agc ccc ctg      348
Lys Pro Tyr Leu Phe Tyr Phe Asn Ile Val Lys Cys Ala Ser Pro Leu
            85                  90                  95

gtt ctg ctg gaa ttc caa tgt ccc act ccc cag atc tgc gtg gaa aaa      396
Val Leu Leu Glu Phe Gln Cys Pro Thr Pro Gln Ile Cys Val Glu Lys
        100                 105                 110
```

-continued

```
tgc ccc gac cgc tac ctc acg tac ctg aat gct cgc agc tcc cgg gac      444
Cys Pro Asp Arg Tyr Leu Thr Tyr Leu Asn Ala Arg Ser Ser Arg Asp
    115                 120                 125

ttt gag tac tat aag cag ttc tgt gtt cct ggc ttc aag aac aat aaa      492
Phe Glu Tyr Tyr Lys Gln Phe Cys Val Pro Gly Phe Lys Asn Asn Lys
130                 135                 140                 145

gga gtg gct gag gtg ctt cga gat ggt gac tgc cct gct gtc ctc atc      540
Gly Val Ala Glu Val Leu Arg Asp Gly Asp Cys Pro Ala Val Leu Ile
                150                 155                 160

ccc agc aaa ccc ttg gcc cgg aga tgc ttc ccc gct atc cac gcc tac      588
Pro Ser Lys Pro Leu Ala Arg Arg Cys Phe Pro Ala Ile His Ala Tyr
            165                 170                 175

aag ggt gtc ctg atg gtg ggc aat gag acg acc tat gag gat ggg cat      636
Lys Gly Val Leu Met Val Gly Asn Glu Thr Thr Tyr Glu Asp Gly His
        180                 185                 190

ggc tcc cgg aaa aac atc aca gac ctg gtg gag ggc gcc aag aaa gcc      684
Gly Ser Arg Lys Asn Ile Thr Asp Leu Val Glu Gly Ala Lys Lys Ala
    195                 200                 205

aat gga gtc cta gag gcg cgg caa ctc gcc atg cgc ata ttt gaa gat      732
Asn Gly Val Leu Glu Ala Arg Gln Leu Ala Met Arg Ile Phe Glu Asp
210                 215                 220                 225

tac acc gtc tct tgg tac tgg att atc ata ggc ctg gtc att gcc atg      780
Tyr Thr Val Ser Trp Tyr Trp Ile Ile Ile Gly Leu Val Ile Ala Met
                230                 235                 240

gcg atg agc ctc ctg ttc atc atc ctg ctt cgc ttc ctg gct ggt att      828
Ala Met Ser Leu Leu Phe Ile Ile Leu Leu Arg Phe Leu Ala Gly Ile
            245                 250                 255

atg gtc tgg gtg atg atc atc atg gtg att ctg gtg ctg ggc tac gga      876
Met Val Trp Val Met Ile Ile Met Val Ile Leu Val Leu Gly Tyr Gly
        260                 265                 270

ata ttt cac tgc tac atg gag tac tcc cga ctg cgt ggt gag gcc ggc      924
Ile Phe His Cys Tyr Met Glu Tyr Ser Arg Leu Arg Gly Glu Ala Gly
    275                 280                 285

tct gat gtc tct ttg gtg gac ctc ggc ttt cag acg gat ttc cgg gtg      972
Ser Asp Val Ser Leu Val Asp Leu Gly Phe Gln Thr Asp Phe Arg Val
290                 295                 300                 305

tac ctg cac tta cgg cag acc tgg ttg gcc ttt atg atc att ctg agt     1020
Tyr Leu His Leu Arg Gln Thr Trp Leu Ala Phe Met Ile Ile Leu Ser
                310                 315                 320

atc ctt gaa gtc att atc atc ttg ctg ctc atc ttt ctc cgg aag aga     1068
Ile Leu Glu Val Ile Ile Ile Leu Leu Leu Ile Phe Leu Arg Lys Arg
            325                 330                 335

att ctc atc gcg att gca ctc atc aaa gaa gcc agc agg gct gtg gga     1116
Ile Leu Ile Ala Ile Ala Leu Ile Lys Glu Ala Ser Arg Ala Val Gly
        340                 345                 350

tac gtc atg tgc tcc ttg ctc tac cca ctg gtc acc ttc ttc ttg ctg     1164
Tyr Val Met Cys Ser Leu Leu Tyr Pro Leu Val Thr Phe Phe Leu Leu
    355                 360                 365

tgc ctc tgc atc gcc tac tgg gcc agc act gct gtc ttc ctg tcc act     1212
Cys Leu Cys Ile Ala Tyr Trp Ala Ser Thr Ala Val Phe Leu Ser Thr
370                 375                 380                 385

tcc aac gaa gcg gtc tat aag atc ttt gat gac agc ccc tgc cca ttt     1260
Ser Asn Glu Ala Val Tyr Lys Ile Phe Asp Asp Ser Pro Cys Pro Phe
                390                 395                 400

act gcg aaa acc tgc aac cca gag acc ttc ccc tcc tcc cat gag tcc     1308
Thr Ala Lys Thr Cys Asn Pro Glu Thr Phe Pro Ser Ser His Glu Ser
            405                 410                 415

cgc caa tgc ccc aat gcc cgt tgc cag ttc gtc ttc tac ggt ggt gag     1356
Arg Gln Cys Pro Asn Ala Arg Cys Gln Phe Val Phe Tyr Gly Gly Glu
        420                 425                 430
```

-continued

```
tcg ggc tac cac cgg gcc ctg ctg ggc ctg cag atc ttc aat gcc ttc     1404
Ser Gly Tyr His Arg Ala Leu Leu Gly Leu Gln Ile Phe Asn Ala Phe
    435                 440                 445

atg ttc ttc tgg ttg gcc aac ttc gtg ctg gcg ctg ggc cag gtc acg     1452
Met Phe Phe Trp Leu Ala Asn Phe Val Leu Ala Leu Gly Gln Val Thr
450                 455                 460                 465

ctg gcc ggg gcc ttt gcc tcc tac tac tgg gcc ctg cgc aag ccg gac     1500
Leu Ala Gly Ala Phe Ala Ser Tyr Tyr Trp Ala Leu Arg Lys Pro Asp
                470                 475                 480

gac ctg ccg gcc ttc ccg ctc ttc tct gcc ttt ggc cgg gcg ctc agg     1548
Asp Leu Pro Ala Phe Pro Leu Phe Ser Ala Phe Gly Arg Ala Leu Arg
            485                 490                 495

tac cac aca ggc tcc ctg gcc ttt ggc gcg ctc atc ctg gcc att gtg     1596
Tyr His Thr Gly Ser Leu Ala Phe Gly Ala Leu Ile Leu Ala Ile Val
        500                 505                 510

cag atc atc cgt gtg ata ctc gag tac ctg gat cag cgg ctg aaa gct     1644
Gln Ile Ile Arg Val Ile Leu Glu Tyr Leu Asp Gln Arg Leu Lys Ala
    515                 520                 525

gca gag aac aag ttt gcc aag tgc ctc atg acc tgt ctc aaa tgc tgc     1692
Ala Glu Asn Lys Phe Ala Lys Cys Leu Met Thr Cys Leu Lys Cys Cys
530                 535                 540                 545

ttc tgg tgc ctg gag aag ttc atc aaa ttc ctt aat agg aat gcc tac     1740
Phe Trp Cys Leu Glu Lys Phe Ile Lys Phe Leu Asn Arg Asn Ala Tyr
                550                 555                 560

atc atg att gcc atc tac ggc acc aat ttc tgc acc tcg gcc agg aat     1788
Ile Met Ile Ala Ile Tyr Gly Thr Asn Phe Cys Thr Ser Ala Arg Asn
            565                 570                 575

gcc ttc ttc ctg ctc atg aga aac atc atc aga gtg gct gtc ctg gat     1836
Ala Phe Phe Leu Leu Met Arg Asn Ile Ile Arg Val Ala Val Leu Asp
        580                 585                 590

aaa gtt act gac ttc ctc ttc ctg ttg ggc aaa ctt ctg atc gtt ggt     1884
Lys Val Thr Asp Phe Leu Phe Leu Leu Gly Lys Leu Leu Ile Val Gly
    595                 600                 605

agt gtg ggg atc ctg gct ttc ttc ttc ttc acc cac cgt atc agg atc     1932
Ser Val Gly Ile Leu Ala Phe Phe Phe Phe Thr His Arg Ile Arg Ile
610                 615                 620                 625

gtg cag gat aca gca cca ccc ctc aat tat tac tgg gtt cct ata ctg     1980
Val Gln Asp Thr Ala Pro Pro Leu Asn Tyr Tyr Trp Val Pro Ile Leu
                630                 635                 640

acg gtg atc gtt ggc tcc tac ttg att gca cac ggt ttc ttc agc gtc     2028
Thr Val Ile Val Gly Ser Tyr Leu Ile Ala His Gly Phe Phe Ser Val
            645                 650                 655

tat ggc atg tgt gtg gac acg ctg ttc ctc tgc ttc ttg gag gac ctg     2076
Tyr Gly Met Cys Val Asp Thr Leu Phe Leu Cys Phe Leu Glu Asp Leu
        660                 665                 670

gag agg aat gac ggc tcg gcc gag agg cct tac ttc atg tct tcc acc     2124
Glu Arg Asn Asp Gly Ser Ala Glu Arg Pro Tyr Phe Met Ser Ser Thr
    675                 680                 685

ctc aag aaa ctc ttg aac aag acc aac aag aag gca gcg gag tcc tga     2172
Leu Lys Lys Leu Leu Asn Lys Thr Asn Lys Lys Ala Ala Glu Ser  *
690                 695                 700

aggccccgtg ctccccacct ctcaaggagt ctcatgccgc agggtgctca gtagctgggt   2232

ctgttccccc agccccttgg gctcacctga agtcctatca ctgccgctct gcccctcccc   2292

atgagccaga tcccaccagt ttctggacgt ggagagtctg ggcatctccc ttcttatgcc   2352

aaggggcgct tggagttttc atggctgccc ctccagactg cgagaaacaa gtaaaaaccc   2412

attggggcct cttgatgtct gggatggcac gtggcccgac ctccacaagc tccctcatgc   2472
```

-continued ttcctgtccc ccgcttacac gacaacgggc cagaccacgg gaaggacggt gtttgtgtct 2532 gagggagctg ctggccacag tgaacaccca cgtttattcc tgcctgctcc ggccaggact 2592 gaacccccttc tccacacctg aacagttggc tcaagggcca ccagaagcat ttctttatta 2652 ttattatttt ttaacctgga catgcattaa agggtctatt agctttcaaa aaaaaaaaaa 2712 aaaaaaaaaa aaaaaaaaaa aaaaa 2737

<210> SEQ ID NO 7
<211> LENGTH: 704
<212> TYPE: PRT
<213> ORGANISM: Homo sapiens

<400> SEQUENCE: 7

Met Glu Asp Glu Arg Lys Asn Gly Ala Tyr Gly Thr Pro Gln Lys Tyr
1 5 10 15

Asp Pro Thr Phe Lys Gly Pro Ile Tyr Asn Arg Gly Cys Thr Asp Ile
20 25 30

Ile Cys Cys Val Phe Leu Leu Leu Ala Ile Val Gly Tyr Val Ala Val
35 40 45

Gly Ile Ile Ala Trp Thr His Gly Asp Pro Arg Lys Val Ile Tyr Pro
50 55 60

Thr Asp Ser Arg Gly Glu Phe Cys Gly Gln Lys Gly Thr Lys Asn Glu
65 70 75 80

Asn Lys Pro Tyr Leu Phe Tyr Phe Asn Ile Val Lys Cys Ala Ser Pro
85 90 95

Leu Val Leu Leu Glu Phe Gln Cys Pro Thr Pro Gln Ile Cys Val Glu
100 105 110

Lys Cys Pro Asp Arg Tyr Leu Thr Tyr Leu Asn Ala Arg Ser Ser Arg
115 120 125

Asp Phe Glu Tyr Tyr Lys Gln Phe Cys Val Pro Gly Phe Lys Asn Asn
130 135 140

Lys Gly Val Ala Glu Val Leu Arg Asp Gly Asp Cys Pro Ala Val Leu
145 150 155 160

Ile Pro Ser Lys Pro Leu Ala Arg Arg Cys Phe Pro Ala Ile His Ala
165 170 175

Tyr Lys Gly Val Leu Met Val Gly Asn Glu Thr Thr Tyr Glu Asp Gly
180 185 190

His Gly Ser Arg Lys Asn Ile Thr Asp Leu Val Glu Gly Ala Lys Lys
195 200 205

Ala Asn Gly Val Leu Glu Ala Arg Gln Leu Ala Met Arg Ile Phe Glu
210 215 220

Asp Tyr Thr Val Ser Trp Tyr Trp Ile Ile Ile Gly Leu Val Ile Ala
225 230 235 240

Met Ala Met Ser Leu Leu Phe Ile Ile Leu Leu Arg Phe Leu Ala Gly
245 250 255

Ile Met Val Trp Val Met Ile Ile Met Val Ile Leu Val Leu Gly Tyr
260 265 270

Gly Ile Phe His Cys Tyr Met Glu Tyr Ser Arg Leu Arg Gly Glu Ala
275 280 285

Gly Ser Asp Val Ser Leu Val Asp Leu Gly Phe Gln Thr Asp Phe Arg
290 295 300

Val Tyr Leu His Leu Arg Gln Thr Trp Leu Ala Phe Met Ile Ile Leu
305 310 315 320

Ser Ile Leu Glu Val Ile Ile Ile Leu Leu Leu Ile Phe Leu Arg Lys

```
                325                 330                 335

Arg Ile Leu Ile Ala Ile Ala Leu Ile Lys Glu Ala Ser Arg Ala Val
            340                 345                 350

Gly Tyr Val Met Cys Ser Leu Leu Tyr Pro Leu Val Thr Phe Phe Leu
        355                 360                 365

Leu Cys Leu Cys Ile Ala Tyr Trp Ala Ser Thr Ala Val Phe Leu Ser
    370                 375                 380

Thr Ser Asn Glu Ala Val Tyr Lys Ile Phe Asp Asp Ser Pro Cys Pro
385                 390                 395                 400

Phe Thr Ala Lys Thr Cys Asn Pro Glu Thr Phe Pro Ser Ser His Glu
                405                 410                 415

Ser Arg Gln Cys Pro Asn Ala Arg Cys Gln Phe Val Phe Tyr Gly Gly
            420                 425                 430

Glu Ser Gly Tyr His Arg Ala Leu Leu Gly Leu Gln Ile Phe Asn Ala
        435                 440                 445

Phe Met Phe Phe Trp Leu Ala Asn Phe Val Leu Ala Leu Gly Gln Val
    450                 455                 460

Thr Leu Ala Gly Ala Phe Ala Ser Tyr Tyr Trp Ala Leu Arg Lys Pro
465                 470                 475                 480

Asp Asp Leu Pro Ala Phe Pro Leu Phe Ser Ala Phe Gly Arg Ala Leu
                485                 490                 495

Arg Tyr His Thr Gly Ser Leu Ala Phe Gly Ala Leu Ile Leu Ala Ile
            500                 505                 510

Val Gln Ile Ile Arg Val Ile Leu Glu Tyr Leu Asp Gln Arg Leu Lys
        515                 520                 525

Ala Ala Glu Asn Lys Phe Ala Lys Cys Leu Met Thr Cys Leu Lys Cys
    530                 535                 540

Cys Phe Trp Cys Leu Glu Lys Phe Ile Lys Phe Leu Asn Arg Asn Ala
545                 550                 555                 560

Tyr Ile Met Ile Ala Ile Tyr Gly Thr Asn Phe Cys Thr Ser Ala Arg
                565                 570                 575

Asn Ala Phe Phe Leu Leu Met Arg Asn Ile Ile Arg Val Ala Val Leu
            580                 585                 590

Asp Lys Val Thr Asp Phe Leu Phe Leu Leu Gly Lys Leu Leu Ile Val
        595                 600                 605

Gly Ser Val Gly Ile Leu Ala Phe Phe Phe Phe Thr His Arg Ile Arg
    610                 615                 620

Ile Val Gln Asp Thr Ala Pro Pro Leu Asn Tyr Tyr Trp Val Pro Ile
625                 630                 635                 640

Leu Thr Val Ile Val Gly Ser Tyr Leu Ile Ala His Gly Phe Phe Ser
                645                 650                 655

Val Tyr Gly Met Cys Val Asp Thr Leu Phe Leu Cys Phe Leu Glu Asp
            660                 665                 670

Leu Glu Arg Asn Asp Gly Ser Ala Glu Arg Pro Tyr Phe Met Ser Ser
        675                 680                 685

Thr Leu Lys Lys Leu Leu Asn Lys Thr Asn Lys Lys Ala Ala Glu Ser
    690                 695                 700
```

```
<210> SEQ ID NO 8
<211> LENGTH: 4
<212> TYPE: PRT
<213> ORGANISM: Homo sapiens

<400> SEQUENCE: 8
```

Asn Arg Ser Cys
 1

<210> SEQ ID NO 9
<211> LENGTH: 4
<212> TYPE: PRT
<213> ORGANISM: Homo sapiens

<400> SEQUENCE: 9

Asn Ser Thr Gly
 1

<210> SEQ ID NO 10
<211> LENGTH: 4
<212> TYPE: PRT
<213> ORGANISM: Homo sapiens

<400> SEQUENCE: 10

Asn Met Thr Val
 1

<210> SEQ ID NO 11
<211> LENGTH: 4
<212> TYPE: PRT
<213> ORGANISM: Homo sapiens

<400> SEQUENCE: 11

Asn Asp Thr Thr
 1

<210> SEQ ID NO 12
<211> LENGTH: 4
<212> TYPE: PRT
<213> ORGANISM: Homo sapiens

<400> SEQUENCE: 12

Asn Leu Ser Ala
 1

<210> SEQ ID NO 13
<211> LENGTH: 4
<212> TYPE: PRT
<213> ORGANISM: Homo sapiens

<400> SEQUENCE: 13

Asn Ile Ser Ser
 1

<210> SEQ ID NO 14
<211> LENGTH: 4
<212> TYPE: PRT
<213> ORGANISM: Homo sapiens

<400> SEQUENCE: 14

Asn Thr Ser Cys
 1

<210> SEQ ID NO 15
<211> LENGTH: 4
<212> TYPE: PRT
<213> ORGANISM: Homo sapiens

<400> SEQUENCE: 15

Asn Ser Ser Cys
 1

<210> SEQ ID NO 16
<211> LENGTH: 4
<212> TYPE: PRT
<213> ORGANISM: Homo sapiens

<400> SEQUENCE: 16

Asn Gly Ser Leu
 1

<210> SEQ ID NO 17
<211> LENGTH: 4
<212> TYPE: PRT
<213> ORGANISM: Homo sapiens

<400> SEQUENCE: 17

Ser Cys Thr Asp
 1

<210> SEQ ID NO 18
<211> LENGTH: 4
<212> TYPE: PRT
<213> ORGANISM: Homo sapiens

<400> SEQUENCE: 18

Ser Val Ala Glu
 1

<210> SEQ ID NO 19
<211> LENGTH: 4
<212> TYPE: PRT
<213> ORGANISM: Homo sapiens

<400> SEQUENCE: 19

Ser Cys Pro Glu
 1

<210> SEQ ID NO 20
<211> LENGTH: 4
<212> TYPE: PRT
<213> ORGANISM: Homo sapiens

<400> SEQUENCE: 20

Thr Val Gly Glu
 1

<210> SEQ ID NO 21
<211> LENGTH: 4
<212> TYPE: PRT
<213> ORGANISM: Homo sapiens

<400> SEQUENCE: 21

Ser Val Gln Glu
 1

<210> SEQ ID NO 22
<211> LENGTH: 8
<212> TYPE: PRT
<213> ORGANISM: Homo sapiens

<400> SEQUENCE: 22

Arg Asp Glu Asp Asp Glu Ala Tyr
 1               5

<210> SEQ ID NO 23
<211> LENGTH: 6
<212> TYPE: PRT
<213> ORGANISM: Homo sapiens

<400> SEQUENCE: 23

Gly Ala Tyr Cys Gly Met
1 5

<210> SEQ ID NO 24
<211> LENGTH: 6
<212> TYPE: PRT
<213> ORGANISM: Homo sapiens

<400> SEQUENCE: 24

Gly Met Gly Glu Asn Lys
1 5

<210> SEQ ID NO 25
<211> LENGTH: 6
<212> TYPE: PRT
<213> ORGANISM: Homo sapiens

<400> SEQUENCE: 25

Gly Val Pro Trp Asn Met
1 5

<210> SEQ ID NO 26
<211> LENGTH: 6
<212> TYPE: PRT
<213> ORGANISM: Homo sapiens

<400> SEQUENCE: 26

Gly Leu Ile Asp Ser Leu
1 5

<210> SEQ ID NO 27
<211> LENGTH: 6
<212> TYPE: PRT
<213> ORGANISM: Homo sapiens

<400> SEQUENCE: 27

Gly Ile Tyr Tyr Cys Trp
1 5

<210> SEQ ID NO 28
<211> LENGTH: 6
<212> TYPE: PRT
<213> ORGANISM: Homo sapiens

<400> SEQUENCE: 28

Gly Ala Ser Ile Ser Gln
1 5

<210> SEQ ID NO 29
<211> LENGTH: 6
<212> TYPE: PRT
<213> ORGANISM: Homo sapiens

<400> SEQUENCE: 29

Gly Gln Met Met Ser Thr
1 5

<210> SEQ ID NO 30
<211> LENGTH: 6

-continued

<212> TYPE: PRT
<213> ORGANISM: Homo sapiens

<400> SEQUENCE: 30

Gly Leu Phe Trp Thr Leu
 1 5

<210> SEQ ID NO 31
<211> LENGTH: 6
<212> TYPE: PRT
<213> ORGANISM: Homo sapiens

<400> SEQUENCE: 31

Gly Ala Phe Ala Ser Phe
 1 5

<210> SEQ ID NO 32
<211> LENGTH: 4
<212> TYPE: PRT
<213> ORGANISM: Homo sapiens

<400> SEQUENCE: 32

Leu Gly Lys Lys
 1

<210> SEQ ID NO 33
<211> LENGTH: 21
<212> TYPE: PRT
<213> ORGANISM: Homo sapiens

<400> SEQUENCE: 33

Leu Phe Ile Leu Leu Leu Arg Leu Val Ala Gly Pro Leu Val Leu Val
 1 5 10 15

Ile Leu Gly Val Leu
 20

<210> SEQ ID NO 34
<211> LENGTH: 14
<212> TYPE: DNA
<213> ORGANISM: Artificial sequence
<220> FEATURE:
<223> OTHER INFORMATION: cDNA synthesis primer

<400> SEQUENCE: 34
ttttgatcaa gctt 14

<210> SEQ ID NO 35
<211> LENGTH: 42
<212> TYPE: DNA
<213> ORGANISM: Artificial sequence
<220> FEATURE:
<223> OTHER INFORMATION: Adaptor 1

<400> SEQUENCE: 35
ctaatacgac tcactatagg gctcgagcgg ccgcccgggc ag 42

<210> SEQ ID NO 36
<211> LENGTH: 12
<212> TYPE: DNA
<213> ORGANISM: Artificial sequence
<220> FEATURE:
<223> OTHER INFORMATION: Adaptor 1

<400> SEQUENCE: 36
gatcctgccc gg 12

<210> SEQ ID NO 37
<211> LENGTH: 40
<212> TYPE: DNA
<213> ORGANISM: Artificial sequence
<220> FEATURE:
<223> OTHER INFORMATION: Adaptor 2

<400> SEQUENCE: 37
gtaatacgac tcactatagg gcagcgtggt cgcggccgag 40

<210> SEQ ID NO 38
<211> LENGTH: 10
<212> TYPE: DNA
<213> ORGANISM: Artificial sequence
<220> FEATURE:
<223> OTHER INFORMATION: Adaptor 2

<400> SEQUENCE: 38
gatcctcggc 10

<210> SEQ ID NO 39
<211> LENGTH: 22
<212> TYPE: DNA
<213> ORGANISM: Artificial sequence
<220> FEATURE:
<223> OTHER INFORMATION: PCR primer 1

<400> SEQUENCE: 39
ctaatacgac tcactatagg gc 22

<210> SEQ ID NO 40
<211> LENGTH: 22
<212> TYPE: DNA
<213> ORGANISM: Artificial sequence
<220> FEATURE:
<223> OTHER INFORMATION: Nested primer 1

<400> SEQUENCE: 40
tcgagcggcc gcccgggcag ga 22

<210> SEQ ID NO 41
<211> LENGTH: 20
<212> TYPE: DNA
<213> ORGANISM: Artificial sequence
<220> FEATURE:
<223> OTHER INFORMATION: Nested primer 2

<400> SEQUENCE: 41
agcgtggtcg cggccgagga 20

<210> SEQ ID NO 42
<211> LENGTH: 25
<212> TYPE: DNA
<213> ORGANISM: Homo sapiens

<400> SEQUENCE: 42
atatcgccgc gctcgtcgtc gacaa 25

<210> SEQ ID NO 43
<211> LENGTH: 26
<212> TYPE: DNA
<213> ORGANISM: Artificial sequence
<220> FEATURE:
<223> OTHER INFORMATION: Primer

<400> SEQUENCE: 43
agccacacgc agctcattgt agaagg 26

<210> SEQ ID NO 44
<211> LENGTH: 23
<212> TYPE: DNA
<213> ORGANISM: Artificial sequence
<220> FEATURE:
<223> OTHER INFORMATION: Primer

<400> SEQUENCE: 44
agatgaggag gaggacaaag gtg 23

<210> SEQ ID NO 45
<211> LENGTH: 23
<212> TYPE: DNA
<213> ORGANISM: Artificial sequence
<220> FEATURE:
<223> OTHER INFORMATION: Primer

<400> SEQUENCE: 45
actgctggga ggagtaccga gtg 23

<210> SEQ ID NO 46
<211> LENGTH: 4
<212> TYPE: PRT
<213> ORGANISM: Homo sapiens

<400> SEQUENCE: 46

Asn Glu Thr Thr
1

<210> SEQ ID NO 47
<211> LENGTH: 4
<212> TYPE: PRT
<213> ORGANISM: Homo sapiens

<400> SEQUENCE: 47

Asn Ile Thr Asp
1

<210> SEQ ID NO 48
<211> LENGTH: 4
<212> TYPE: PRT
<213> ORGANISM: Homo sapiens

<400> SEQUENCE: 48

Asn Lys Thr Asn
1

<210> SEQ ID NO 49
<211> LENGTH: 4
<212> TYPE: PRT
<213> ORGANISM: Homo sapiens

<400> SEQUENCE: 49

Thr His Gly Asp
1

<210> SEQ ID NO 50
<211> LENGTH: 4
<212> TYPE: PRT
<213> ORGANISM: Homo sapiens

<400> SEQUENCE: 50

Ser Arg Gly Glu
1

<210> SEQ ID NO 51
<211> LENGTH: 4
<212> TYPE: PRT
<213> ORGANISM: Homo sapiens

<400> SEQUENCE: 51

Thr Lys Asn Glu
1

<210> SEQ ID NO 52
<211> LENGTH: 4
<212> TYPE: PRT
<213> ORGANISM: Homo sapiens

<400> SEQUENCE: 52

Ser Ser Arg Asp
1

<210> SEQ ID NO 53
<211> LENGTH: 4
<212> TYPE: PRT
<213> ORGANISM: Homo sapiens

<400> SEQUENCE: 53

Thr Thr Tyr Glu
1

<210> SEQ ID NO 54
<211> LENGTH: 4
<212> TYPE: PRT
<213> ORGANISM: Homo sapiens

<400> SEQUENCE: 54

Thr Tyr Glu Asp
1

<210> SEQ ID NO 55
<211> LENGTH: 4
<212> TYPE: PRT
<213> ORGANISM: Homo sapiens

<400> SEQUENCE: 55

Ser Leu Val Asp
1

<210> SEQ ID NO 56
<211> LENGTH: 4
<212> TYPE: PRT
<213> ORGANISM: Homo sapiens

<400> SEQUENCE: 56

Ser Ile Leu Glu
1

<210> SEQ ID NO 57
<211> LENGTH: 4
<212> TYPE: PRT
<213> ORGANISM: Homo sapiens

<400> SEQUENCE: 57

Thr Ser Asn Glu

1

<210> SEQ ID NO 58
<211> LENGTH: 4
<212> TYPE: PRT
<213> ORGANISM: Homo sapiens

<400> SEQUENCE: 58

Ser Ser His Glu
1

<210> SEQ ID NO 59
<211> LENGTH: 9
<212> TYPE: PRT
<213> ORGANISM: Homo sapiens

<400> SEQUENCE: 59

Arg Ser Ser Arg Asp Phe Glu Tyr Tyr
1 5

<210> SEQ ID NO 60
<211> LENGTH: 6
<212> TYPE: PRT
<213> ORGANISM: Homo sapiens

<400> SEQUENCE: 60

Gly Gln Lys Gly Thr Lys
1 5

<210> SEQ ID NO 61
<211> LENGTH: 6
<212> TYPE: PRT
<213> ORGANISM: Homo sapiens

<400> SEQUENCE: 61

Gly Asn Glu Thr Thr Tyr
1 5

<210> SEQ ID NO 62
<211> LENGTH: 6
<212> TYPE: PRT
<213> ORGANISM: Homo sapiens

<400> SEQUENCE: 62

Gly Ser Arg Lys Asn Ile
1 5

<210> SEQ ID NO 63
<211> LENGTH: 6
<212> TYPE: PRT
<213> ORGANISM: Homo sapiens

<400> SEQUENCE: 63

Gly Ala Lys Lys Ala Asn
1 5

<210> SEQ ID NO 64
<211> LENGTH: 6
<212> TYPE: PRT
<213> ORGANISM: Homo sapiens

<400> SEQUENCE: 64

Gly Val Leu Glu Ala Arg
1 5

<210> SEQ ID NO 65
<211> LENGTH: 6
<212> TYPE: PRT
<213> ORGANISM: Homo sapiens

<400> SEQUENCE: 65

Gly Leu Val Ile Ala Met
 1               5

<210> SEQ ID NO 66
<211> LENGTH: 6
<212> TYPE: PRT
<213> ORGANISM: Homo sapiens

<400> SEQUENCE: 66

Gly Ile Phe His Cys Tyr
 1               5

<210> SEQ ID NO 67
<211> LENGTH: 6
<212> TYPE: PRT
<213> ORGANISM: Homo sapiens

<400> SEQUENCE: 67

Gly Ser Asp Val Ser Leu
 1               5

<210> SEQ ID NO 68
<211> LENGTH: 6
<212> TYPE: PRT
<213> ORGANISM: Homo sapiens

<400> SEQUENCE: 68

Gly Gly Glu Ser Gly Tyr
 1               5

<210> SEQ ID NO 69
<211> LENGTH: 6
<212> TYPE: PRT
<213> ORGANISM: Homo sapiens

<400> SEQUENCE: 69

Gly Ala Phe Ala Ser Tyr
 1               5

<210> SEQ ID NO 70
<211> LENGTH: 6
<212> TYPE: PRT
<213> ORGANISM: Homo sapiens

<400> SEQUENCE: 70

Gly Thr Asn Phe Cys Thr
 1               5

<210> SEQ ID NO 71
<211> LENGTH: 14
<212> TYPE: PRT
<213> ORGANISM: Homo sapiens

<400> SEQUENCE: 71

Met Gly Gly Lys Gln Arg Asp Glu Asp Asp Glu Ala Tyr Gly
 1               5                   10